(12) United States Patent
Rodefeld et al.

(10) Patent No.: US 8,449,443 B2
(45) Date of Patent: May 28, 2013

(54) ACTIVE OR PASSIVE ASSISTANCE IN THE CIRCULATORY SYSTEM

(75) Inventors: Mark D. Rodefeld, Zionsville, IN (US); Steven H. Frankel, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 152 days.

(21) Appl. No.: 13/122,797

(22) PCT Filed: Oct. 6, 2009

(86) PCT No.: PCT/US2009/059733
§ 371 (c)(1), (2), (4) Date: Jul. 5, 2011

(87) PCT Pub. No.: WO2010/042546
PCT Pub. Date: Apr. 15, 2010

(65) Prior Publication Data
US 2011/0257462 A1    Oct. 20, 2011

Related U.S. Application Data

(60) Provisional application No. 61/103,110, filed on Oct. 6, 2008, provisional application No. 61/173,029, filed on Apr. 27, 2009.

(51) Int. Cl.
*A61N 1/362*    (2006.01)

(52) U.S. Cl.
USPC .......................................................... 600/16

(58) Field of Classification Search
USPC ............................... 600/16, 37, 509; 604/6.11
See application file for complete search history.

(56) References Cited

U.S. PATENT DOCUMENTS

| | | |
|---|---|---|
| 3,158,258 A | 11/1964 | Kelday |
| 4,327,112 A | 4/1982 | Wurtman |
| 4,753,221 A | 6/1988 | Kensey et al. |
| 4,846,152 A | 7/1989 | Wampler et al. |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 5,112,292 A | 5/1992 | Hwang et al. |
| 5,169,378 A | 12/1992 | Figuera |
| 5,300,112 A | 4/1994 | Barr |
| 5,326,374 A | 7/1994 | Ilbawi et al. |
| 5,348,528 A | 9/1994 | Vince |
| 5,501,574 A | 3/1996 | Raible |
| 5,749,855 A | 5/1998 | Reitan |
| 5,851,174 A | 12/1998 | Jarvik et al. |

(Continued)

FOREIGN PATENT DOCUMENTS

| | | |
|---|---|---|
| WO | 0019097 | 4/2000 |
| WO | 0032256 | 6/2000 |

(Continued)

*Primary Examiner* — George Manuel
*Assistant Examiner* — Robert N Wieland
(74) *Attorney, Agent, or Firm* — John V. Daniluck; Bingham Greenebaum Doll LLP

(57) ABSTRACT

Apparatus and methods for assisting flow of a fluid in a conduit. In some embodiments, a viscous impeller rotating within a protective cage provides a boost and total pressure to blood within the circulatory system of an animal.

38 Claims, 43 Drawing Sheets

A. Norwood

B. Hemi-Fontan

U.S. PATENT DOCUMENTS

| | | | |
|---|---|---|---|
| 5,895,404 A | 4/1999 | Ruiz |
| 5,911,685 A | 6/1999 | Siess et al. |
| 5,921,913 A | 7/1999 | Siess |
| 5,951,263 A | 9/1999 | Taylor et al. |
| 5,964,694 A | 10/1999 | Siess et al. |
| 6,007,478 A | 12/1999 | Siess et al. |
| 6,024,096 A | 2/2000 | Buckberg |
| 6,042,347 A | 3/2000 | Scholl et al. |
| 6,058,593 A | 5/2000 | Siess |
| 6,086,570 A | 7/2000 | Aboul Hosn et al. |
| 6,116,862 A | 9/2000 | Rau et al. |
| 6,123,725 A | 9/2000 | Aboul Hosn |
| 6,135,729 A | 10/2000 | Aber |
| 6,136,025 A | 10/2000 | Barbut et al. |
| 6,139,487 A | 10/2000 | Siess |
| 6,152,704 A | 11/2000 | Aboul Hosn et al. |
| 6,171,295 B1 | 1/2001 | Garabedian et al. |
| 6,176,822 B1 | 1/2001 | Nix et al. |
| 6,176,848 B1 | 1/2001 | Rau et al. |
| 6,210,133 B1 | 4/2001 | Aboul Hosn et al. |
| 6,210,397 B1 | 4/2001 | Aboul Hosn et al. |
| 6,217,541 B1 | 4/2001 | Yu |
| 6,221,104 B1 | 4/2001 | Buckberg et al. |
| 6,228,063 B1 | 5/2001 | Aboul Hosn |
| 6,245,007 B1 | 6/2001 | Bedingham et al. |
| 6,283,988 B1 | 9/2001 | Laufer et al. |
| 6,295,877 B1 | 10/2001 | Aboul Hosn et al. |
| 6,395,026 B1 | 5/2002 | Aboul Hosn et al. |
| 6,439,237 B1 | 8/2002 | Buckberg et al. |
| 6,450,171 B1 | 9/2002 | Buckberg et al. |
| 6,503,224 B1 | 1/2003 | Forman et al. |
| 6,508,787 B2 | 1/2003 | Erbel et al. |
| 6,532,964 B2 | 3/2003 | Aboul Hosn et al. |
| 6,533,716 B1 | 3/2003 | Schmitz et al. |
| 6,544,216 B1 | 4/2003 | Sammler et al. |
| 6,610,004 B2 | 8/2003 | Viole et al. |
| 6,613,008 B2 | 9/2003 | Aboul Hosn et al. |
| 6,623,475 B1 | 9/2003 | Siess |
| 6,627,602 B2 | 9/2003 | Stamler et al. |
| 6,641,558 B1 | 11/2003 | Aboul-Hosn et al. |
| 6,685,621 B2 | 2/2004 | Bolling et al. |
| 6,685,627 B2 | 2/2004 | Jayaraman |
| 6,709,418 B1 | 3/2004 | Aboul-Hosn et al. |
| 6,716,189 B1 | 4/2004 | Jarvik et al. |
| 6,719,720 B1 | 4/2004 | Voelker et al. |
| 6,719,791 B1 | 4/2004 | Nusser et al. |
| 6,752,602 B2 | 6/2004 | Schulte Eistrup et al. |
| 6,794,789 B2 | 9/2004 | Siess et al. |
| 6,808,508 B1 | 10/2004 | Zafirelis et al. |
| 6,814,713 B2 | 11/2004 | Aboul-Hosn et al. |
| 6,858,001 B1 | 2/2005 | Aboul-Hosn |
| 6,889,082 B2 | 5/2005 | Bolling et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,966,748 B2 | 11/2005 | Woodard et al. |
| 6,969,379 B1 | 11/2005 | Aboul-Hosn et al. |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,001,409 B2 | 2/2006 | Amplatz |
| 7,010,954 B2 | 3/2006 | Siess et al. |
| 7,011,620 B1 | 3/2006 | Siess |
| 7,022,100 B1 * | 4/2006 | Aboul-Hosn et al. ........ 604/6.11 |
| 7,027,875 B2 | 4/2006 | Siess et al. |
| 7,056,280 B2 | 6/2006 | Buckberg et al. |
| 7,070,398 B2 | 7/2006 | Olsen et al. |
| 7,070,555 B2 | 7/2006 | Siess |
| 7,090,659 B2 | 8/2006 | Aboul-Hosn et al. |
| 7,125,376 B2 | 10/2006 | Viole et al. |
| 7,144,365 B2 | 12/2006 | Bolling et al. |
| 7,182,727 B2 | 2/2007 | Aboul-Hosn |
| 7,275,546 B2 | 10/2007 | Buckberg et al. |
| 7,331,921 B2 | 2/2008 | Viole et al. |
| 7,374,574 B2 | 5/2008 | Nuesser et al. |
| 7,381,179 B2 | 6/2008 | Aboul-Hosn et al. |
| 7,390,293 B2 | 6/2008 | Jayaraman |
| 7,393,181 B2 | 7/2008 | McBride et al. |
| 7,568,896 B2 | 8/2009 | Dooley |
| 2002/0128587 A1 | 9/2002 | Aboul Hosn et al. |
| 2002/0198603 A1 | 12/2002 | Buckberg et al. |
| 2003/0002976 A1 | 1/2003 | Dial |
| 2003/0105456 A1 | 6/2003 | Lin |
| 2003/0157260 A1 | 8/2003 | Rubner et al. |
| 2003/0167068 A1 | 9/2003 | Amplatz |
| 2003/0171772 A1 | 9/2003 | Amplatz |
| 2003/0176760 A1 | 9/2003 | El Oakley et al. |
| 2003/0208097 A1 | 11/2003 | Aboul Hosn et al. |
| 2004/0015046 A1 | 1/2004 | Buckberg et al. |
| 2004/0116897 A1 | 6/2004 | Aboul Hosn |
| 2004/0181126 A1 | 9/2004 | Buckberg et al. |
| 2004/0181260 A1 | 9/2004 | Anderson et al. |
| 2005/0049696 A1 | 3/2005 | Siess et al. |
| 2005/0119599 A1 | 6/2005 | Kanz et al. |
| 2005/0165269 A9 | 7/2005 | Aboul Hosn et al. |
| 2005/0272741 A1 | 12/2005 | Rychik et al. |
| 2005/0279370 A1 | 12/2005 | Aboul Hosn et al. |
| 2006/0063965 A1 | 3/2006 | Aboul Hosn et al. |
| 2006/0155158 A1 | 7/2006 | Aboul Hosn |
| 2006/0211909 A1 | 9/2006 | Anstadt et al. |
| 2006/0230846 A1 | 10/2006 | Smith et al. |
| 2006/0258900 A1 | 11/2006 | Buckberg et al. |
| 2006/0271085 A1 | 11/2006 | Siess et al. |
| 2007/0129792 A1 | 6/2007 | Picart et al. |
| 2007/0161845 A1 | 7/2007 | Magovern et al. |
| 2007/0197855 A1 | 8/2007 | Richardson et al. |
| 2007/0197856 A1 | 8/2007 | Gellman et al. |
| 2008/0021368 A1 | 1/2008 | Dasi et al. |
| 2008/0086027 A1 | 4/2008 | Siess et al. |
| 2008/0103591 A1 | 5/2008 | Siess |
| 2008/0132748 A1 | 6/2008 | Shifflette |
| 2008/0171070 A1 | 7/2008 | Schaaf et al. |
| 2008/0281214 A1 | 11/2008 | Elle et al. |
| 2009/0024212 A1 | 1/2009 | Siess et al. |
| 2009/0054823 A1 | 2/2009 | Bridges et al. |
| 2009/0112312 A1 | 4/2009 | LaRose et al. |
| 2009/0118567 A1 | 5/2009 | Siess |
| 2009/0138080 A1 | 5/2009 | Siess et al. |
| 2009/0148458 A1 | 6/2009 | Russell et al. |
| 2009/0204205 A1 | 8/2009 | Larose et al. |

FOREIGN PATENT DOCUMENTS

| | | |
|---|---|---|
| WO | 0042919 | 7/2000 |
| WO | 0019097 | 9/2000 |
| WO | 02100475 | 12/2002 |
| WO | 03030964 | 4/2003 |
| WO | 03061455 | 7/2003 |
| WO | 03030964 | 9/2003 |
| WO | 03074119 | 9/2003 |
| WO | 03061455 | 12/2003 |
| WO | 03103745 | 12/2003 |
| WO | 2005016416 | 2/2005 |
| WO | 2005020848 | 3/2005 |
| WO | 2005094521 | 10/2005 |
| WO | 2005020848 | 4/2006 |
| WO | 2006051023 | 5/2006 |
| WO | 2005094521 | 6/2007 |
| WO | 2007112033 | 10/2007 |
| WO | 2007112033 | 5/2008 |
| WO | 2008116765 | 10/2008 |
| WO | 2008152425 | 12/2008 |
| WO | 2008116765 | 1/2009 |
| WO | 2009058726 | 5/2009 |
| WO | 2009073037 | 6/2009 |
| WO | 2010042546 | 4/2010 |
| WO | 2010042546 | 6/2010 |

* cited by examiner

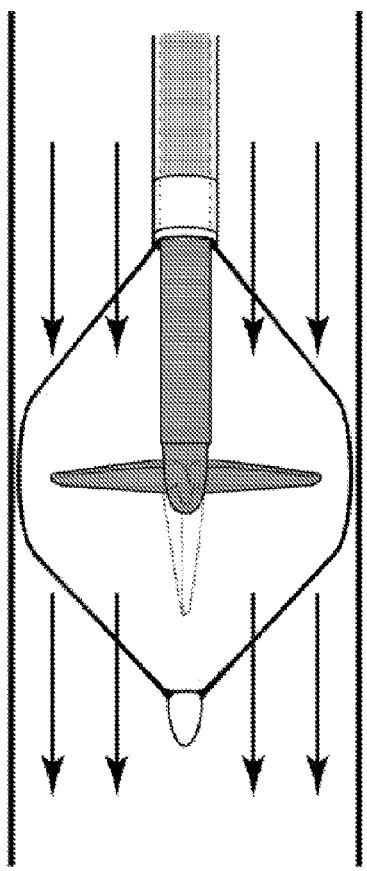
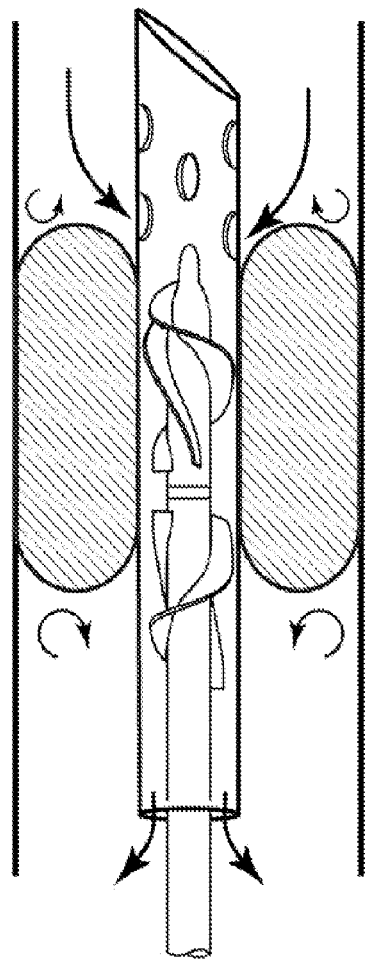
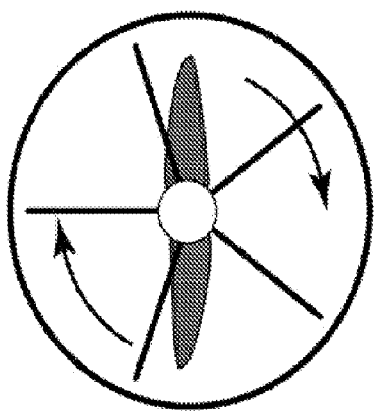
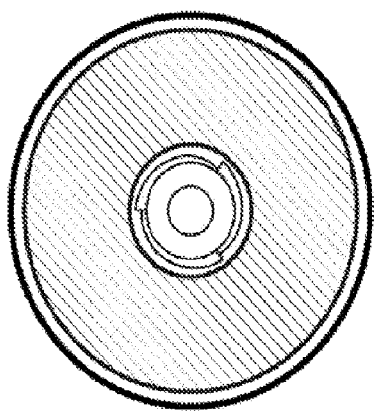
FIG. 3
FIG. 2

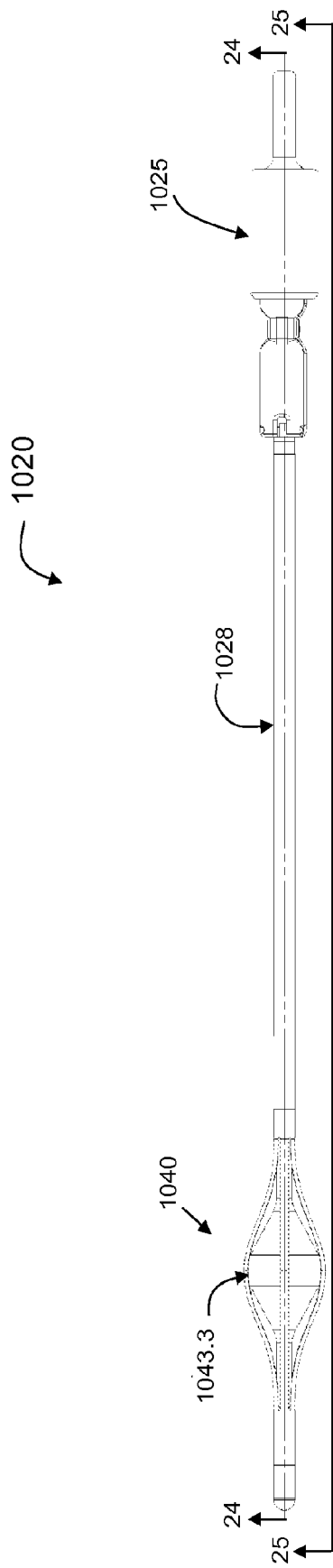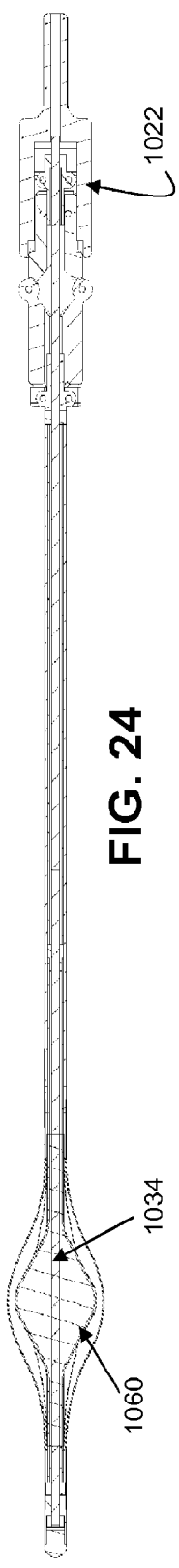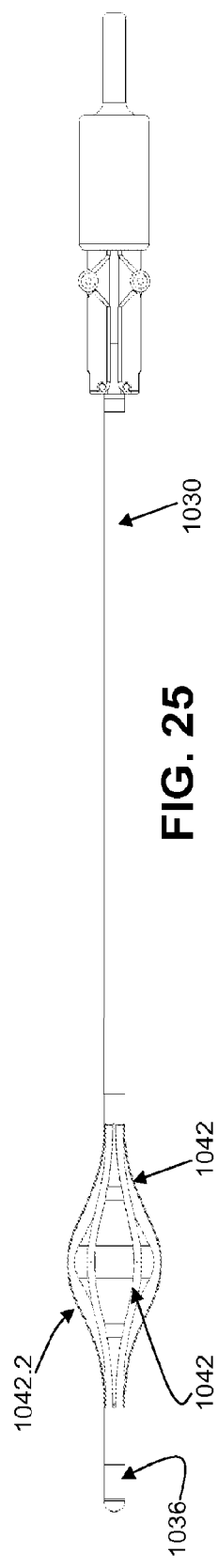
FIG. 23
FIG. 24
FIG. 25

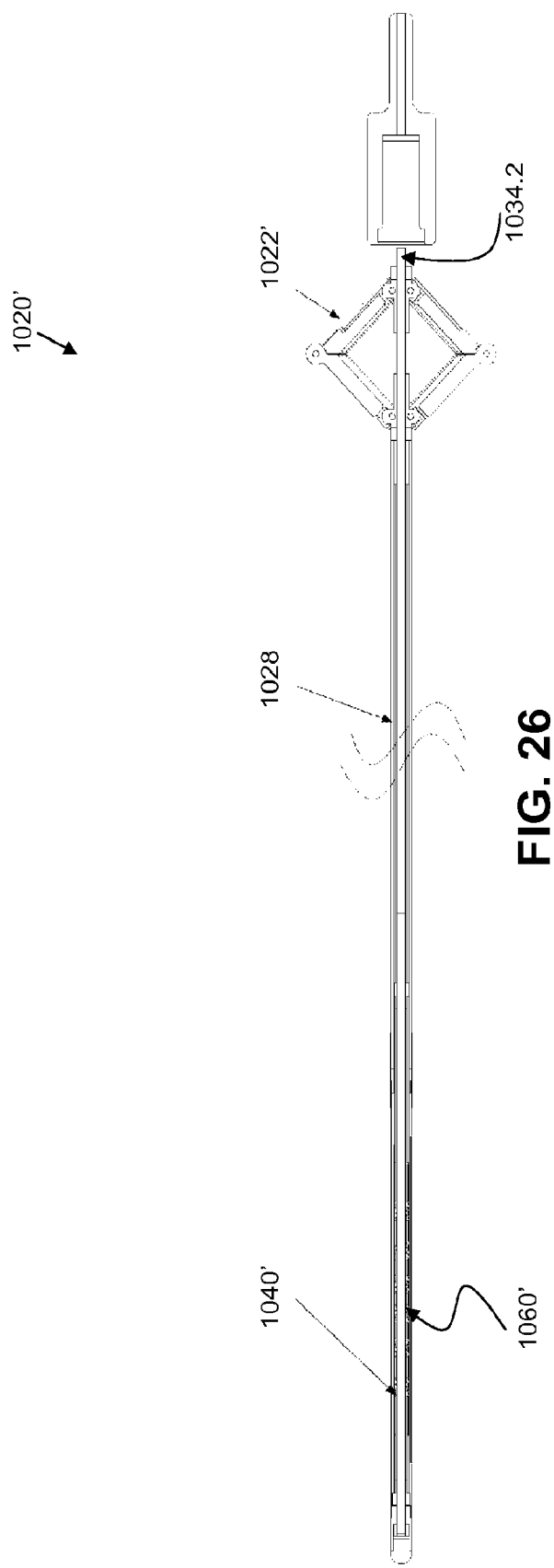

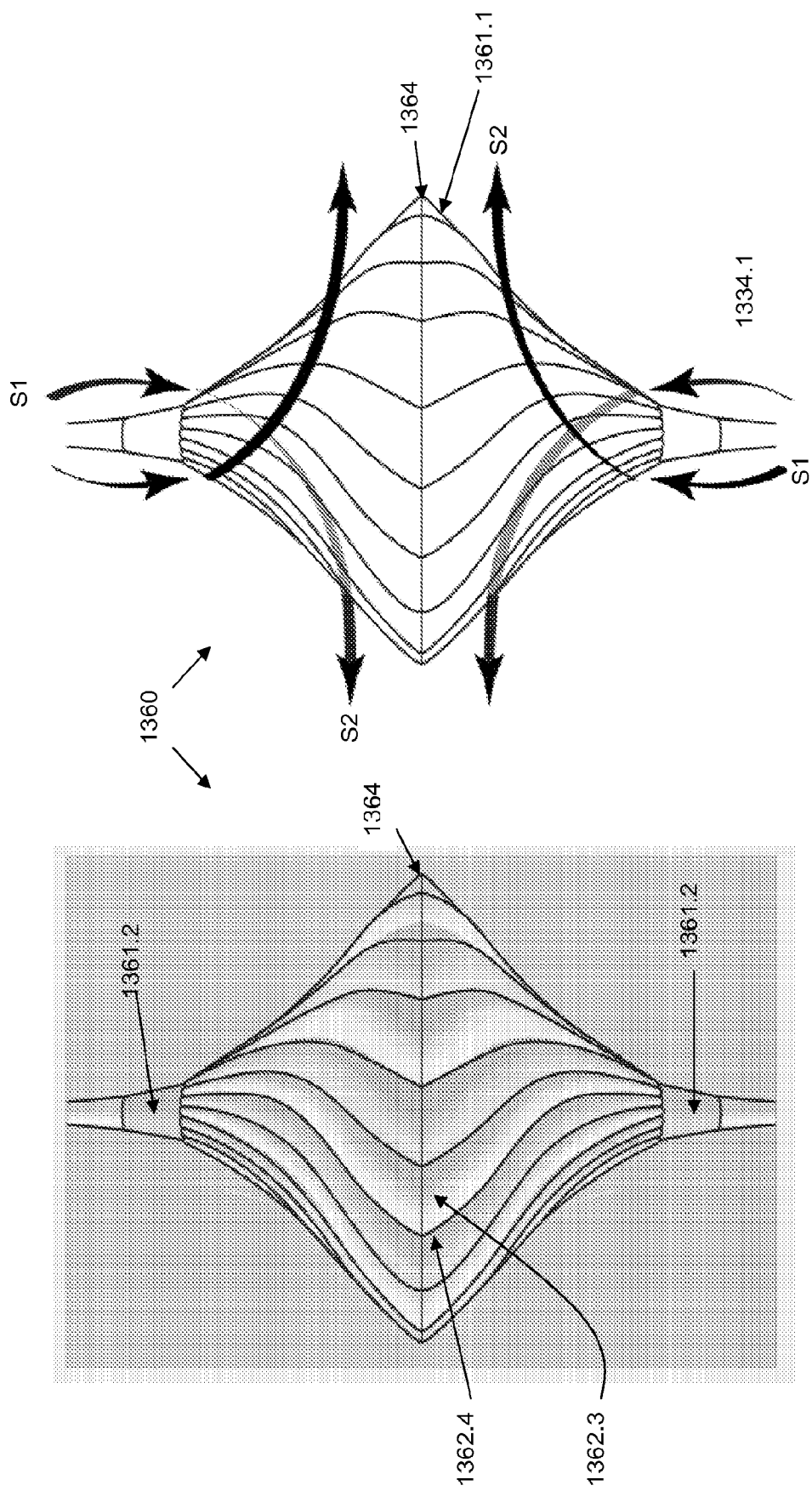

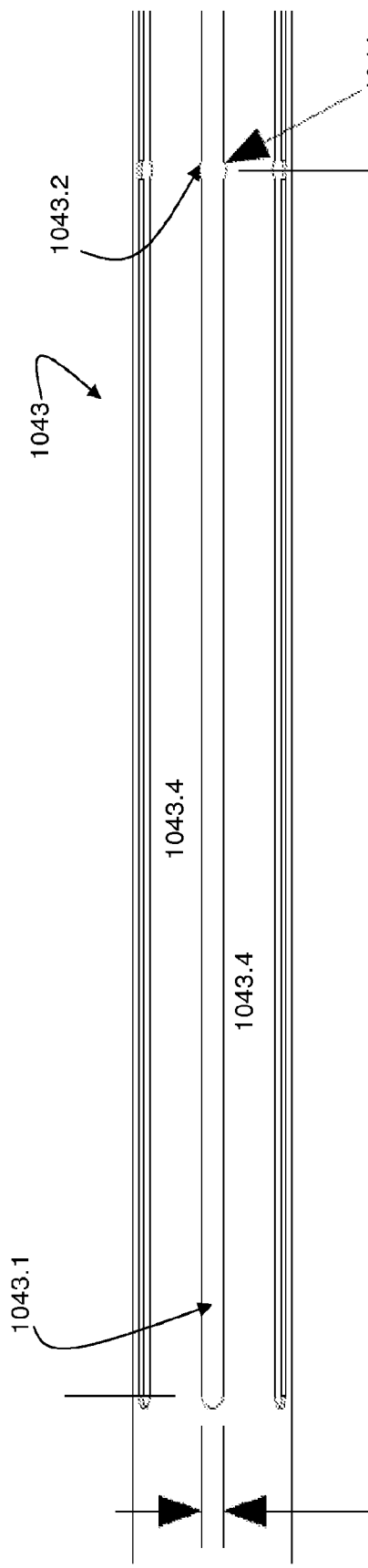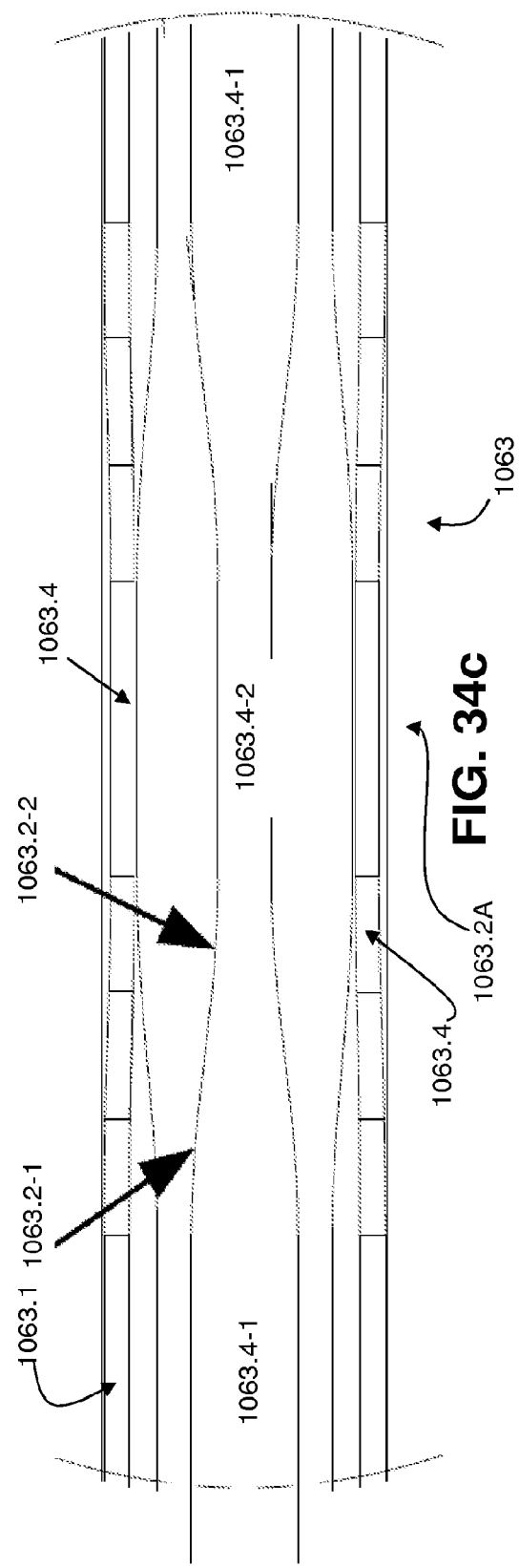
FIG. 35c
FIG. 34c

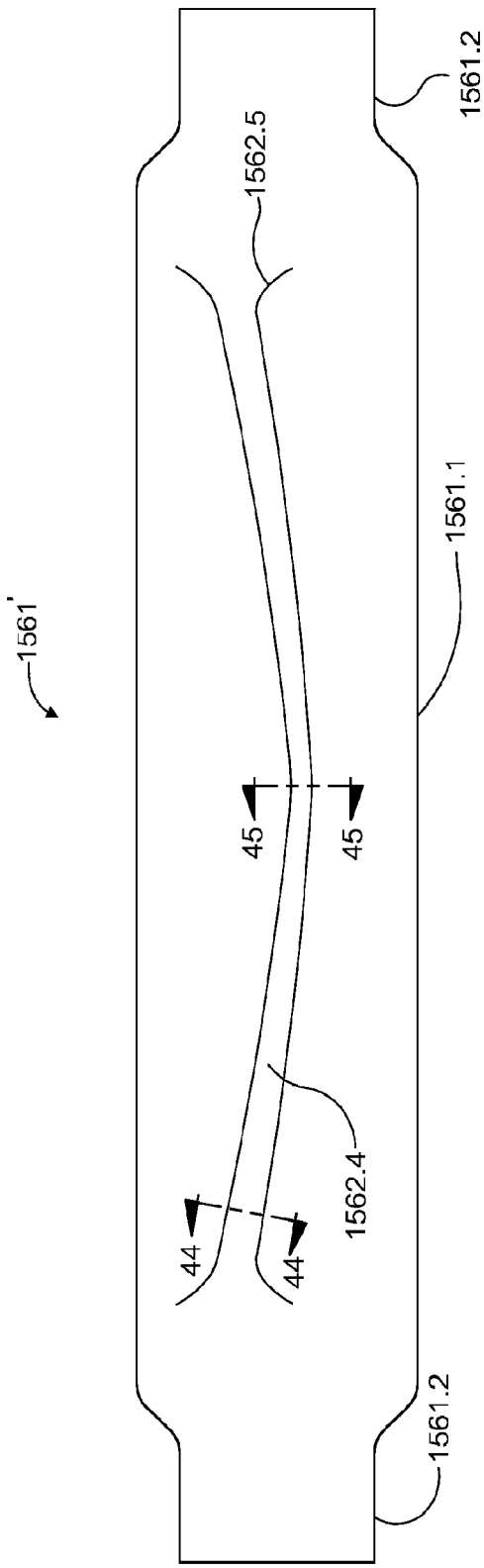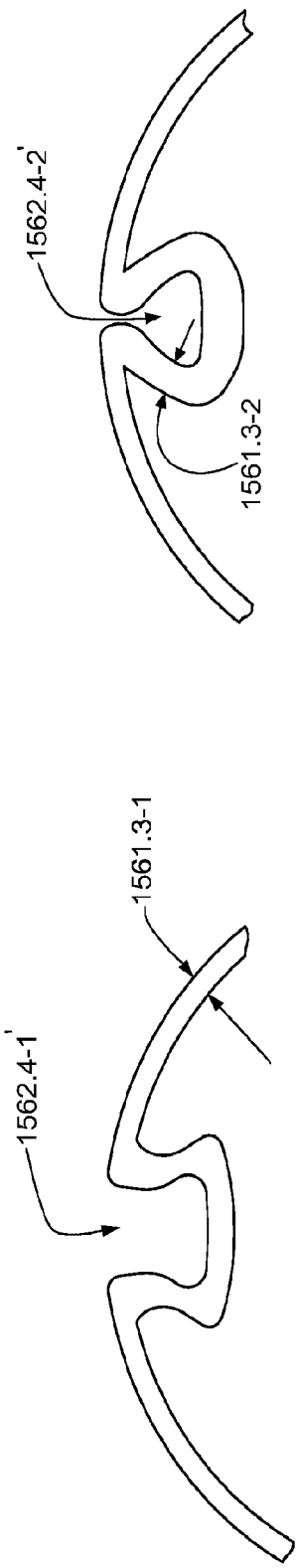

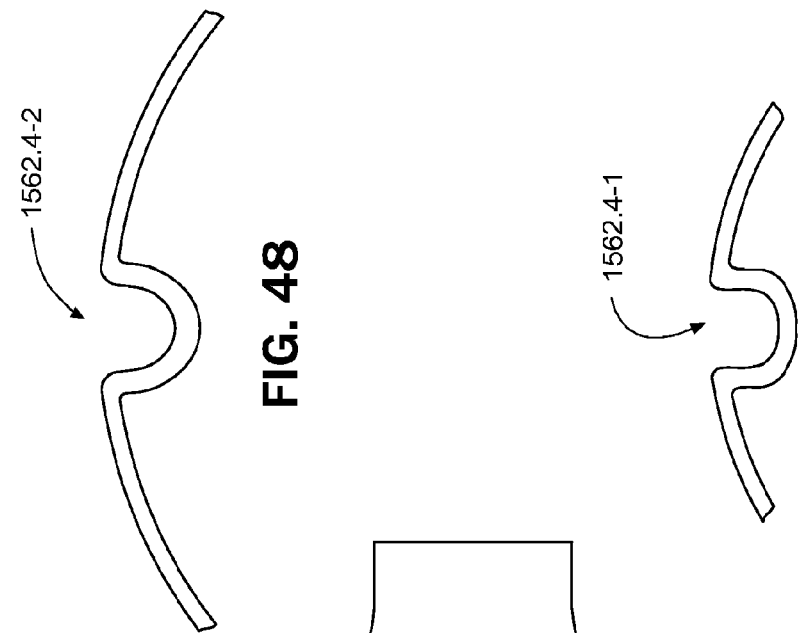
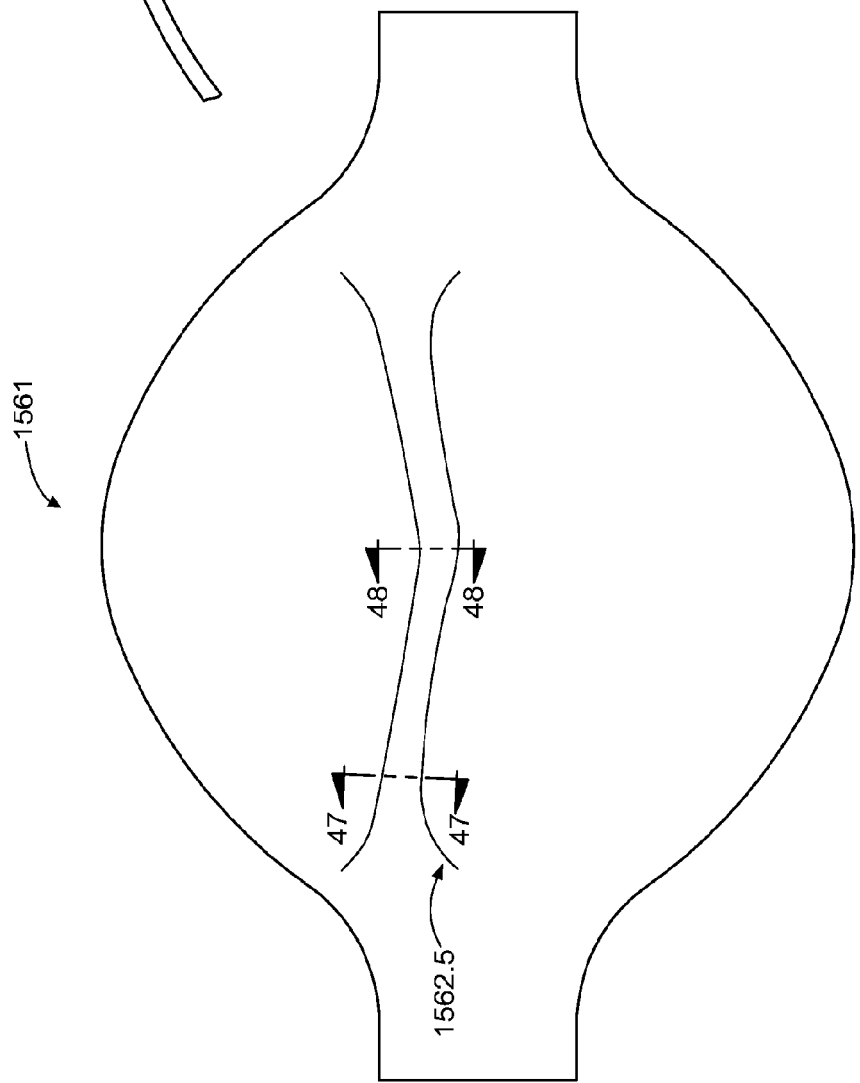

ACTIVE OR PASSIVE ASSISTANCE IN THE CIRCULATORY SYSTEM

CROSS REFERENCE TO RELATED APPLICATIONS

This application is a national stage filing of PCT Patent Application Serial No. PCT/US2009/059733, filed Oct. 6, 2009, and titled METHODS AND APPARATUS FOR ACTIVE OR PASSIVE ASSISTANCE IN THE CIRCULATORY SYSTEM, which claims the benefit of priority to U.S. Provisional Patent Application Ser. No. 61/103,110, filed Oct. 6, 2008, titled CAVOPULMONARY ASSIST METHOD AND DEVICE, and U.S. Provisional Patent Application Ser. No. 61/173,029, filed Apr. 27, 2009, titled METHODS AND APPARATUS FOR ACTIVE OR PASSIVE ASSISTANCE IN THE CIRCULATORY SYSTEM, all of which are incorporated herein by reference.

FIELD OF THE INVENTION

Various embodiments of the present invention pertain to methods and apparatus for improving the circulation of blood in animals, and in particular to methods and apparatus, both active and passive, for assisting cavopulmonary flow.

BACKGROUND OF THE INVENTION

Children born with a single functional ventricle face inordinate challenges over the entirety of their lives. A multiple staged operative treatment strategy offers hope for survival—at high physiologic, financial, and societal cost. Those who are fortunate to survive typically endure lengthy and complex hospital courses. Pathophysiology induced at each stage impacts not only the timing, course, and outcome of subsequent surgical stages, but also impacts long-term status. The staged surgical paradigm has evolved on a clinical basis, and is putatively the only reasonable approach. Because of this, alternative paths to achieve the same result have been neither evident nor sought. There may, in fact, be a safer and more sensible approach.

In a univentricular Fontan circulation, there is no subpulmonary ventricular power source to pump systemic venous blood through the lungs. Consequently, systemic venous pressure is significantly elevated and cardiac output is suboptimal. One way to address such problems includes a means to gently augment blood flow from the great veins through the lungs which would reduce venous pressure and improve ventricular filling, creating conditions comparable to a normal two-ventricle circulation. A gradual reduction in support would allow for a stable transition to elevated systemic venous pressure. Once the circulation has adapted to permit a systemic venous source to perfuse the lungs at normotensive pressures, support can be safely withdrawn.

The treatment of single ventricle heart disease is a highly complex and formidable challenge. It is the fifth most common heart defect, and is the leading cause of death from all structural birth defects in the first year of life. It is also the most costly to treat. Affected infants are typically otherwise normal. Only 50-70% survive through all 3 staged procedures. Fontan repair of single ventricle is considered long-term palliation, and represents a transition from acute to chronic disease. At best, children are left with the physiologic limitations inherent in a univentricular circulation. Despite medical and surgical advances, improved outcomes using the staged protocol have not been realized. Furthermore, for older patients with failing Fontan physiology, therapies are limited: medical therapy indirectly addresses secondary sequelae, and heart transplantation is an end-stage option. One million American adults are now alive with congenital heart disease; those with single ventricle physiology (SVP) represent a significant percentage and are the most problematic subgroup. They utilize resources disproportionate to their numbers, constituting an emerging public health concern. The NHLBI Working Group in Research in Adult Congenital Heart Disease has called for mechanistic and bioengineering research to improve the care of the growing number of children and adults surviving with SVP.

Patients with a univentricular Fontan circulation are at high risk of circulatory insufficiency not only at the time of repair, but also as they age. This is presumably due to the combined sequelae of elevated systemic venous pressure, reduced preload to the single ventricle, and increased afterload. A blood pump specifically designed to augment cavopulmonary flow would address these problems and improve circulatory status by producing conditions more similar to the normal two-ventricle circulation. This is supported by the clinical improvement observed in patients who undergo Fontan conversion from atriopulmonary to total cavopulmonary connections. Hydraulic efficiency in their cavopulmonary circulation is improved by a seemingly trivial, yet highly significant, 2-5 mmHg, which reduces systemic venous pressure, and improves transpulmonary flow and cardiac output.

Numerical modeling of the flow dynamics in a total cavopulmonary connection has been performed (NIH R01 grant #HL67622). It has been shown that a central diverting body at the TCPC intersection will effectively split incoming vena caval flow toward each of the outlets, reducing turbulent kinetic energy loss and maximizing hydraulic efficiency. However, incorporation of a fixed central diverting body into the venous walls as a permanent flow diversion is surgically impractical: In the low-pressure venous circulation, this may be thrombogenic, and would lack growth potential, precluding consideration in children.

Experimental reports of mechanically assisted neonatal Stage-2 Fontan procedures using a paracorporeal pump are also emerging (Reference a February 2009 publication: Honjo O, Merklinger S L, Poe J B, Guerguerian A M, Algamdhi A A, Takatani S, Van Arsdell G S. Mechanical cavopulmonary assist maintains pulmonary and cerebral blood flow in a piglet model of a bidirectional cavopulmonary shunt with high pulmonary vascular resistance. J Thoracic Cardiovasc Surg 2009; 137:355-61). There is growing awareness of the need for innovative paradigms to treat patients with SVP and this can be achieved by assisting cavopulmonary flow. Awareness is growing that this is a viable and improved approach to solve the problems associated with repair of functional single ventricle.

In addition to the problems faced by children born with a single functional ventricle, related problems are faced by patients with congestive heart failure that need temporary or permanent support of their right ventricular function. In patients with congestive heart failure, the most common cause of right heart failure is left heart failure. Furthermore, right heart failure is typically a recoverable event within a span of 2 weeks once the source of left heart failure is addressed. This short time period of recovery makes clinical decision making to commit the patient to surgically invasive right ventricular assist device (RVAD) support difficult. This is an invasive procedure which carries significant complications in patients who are critically ill at baseline.

The hydraulic needs for right ventricular support are approximately one-fifth of the needs for left ventricle support. Support for the right ventricle, particularly if used non-invasively percutaneously inserted, would be most beneficial in conjunction with traditional mechanical LVAD support in patients in whom biventricular dysfunction is present, and in whom the right ventricular dysfunction is felt to be transient secondary to left heart failure and recoverable. In such cases, an improvement in left heart performance via surgical LVAD support will ultimately result in secondarily improved right heart performance. Only temporary right heart support (estimated at $\frac{1}{5}^{th}$ the level of systemic or left heart support) may be necessary until right ventricular function has completely recovered, thus solving the current problem of the need to place a highly invasive and permanent device. Reasonably percutaneous temporary RVAD support devices do not currently exist.

In most cases, right heart support is needed only temporarily until the right ventricle regains function. If an invasive procedure can be avoided, the patient will benefit from having a percutaneous device that can be easily removed when no longer needed. Some available percutaneous devices require trans-septal atrial puncture to deliver assisted flow to the left heart, which has several disadvantages: 1) it is technically challenging to puncture the atrial septum and position the large cannulae, and 2) the blood which is delivered to the systemic circulation via the left atrium is deoxygenated, resulting in systemic oxygen desaturation.

The estimated clinical need related to the heart failure market is substantial:
  Heart failure affects 10 million people globally (5 million in US), with 1 million new cases diagnosed every year
  1 million patients in NYHA Class IV (end-stage) disease
  Of these, an estimated 100,000 per year would benefit from the implantation of a heart pump.
  In the US, heart failure remains Medicare's greatest area of healthcare-related spending
  Long-term device treatment is reimbursed in the US at a minimum USD136,000. Of this, typically USD75,000 is for the device.
  A temporary, disposable, right-heart support device would cost less than that for an implantable device, with reduced morbidity and mortality, resulting in a substantial health care cost reduction and societal benefit.

In addition to the requirements for active assistance of cavopulmonary flow (i.e. components that add energy to the flowing medium), there are also requirements for passive devices (i.e. components that do not add energy, but rather optimize existing flow). As examples, consider the low pressure 3-way "T" (by directional Glenn) and 4-way "+" (total cavopulmonary connection (TCPC)) conditions. In both of these conditions it is possible that flow at the intersection of two flow paths or at the bifurcation of a flow path is excessively turbulent, with a commensurate loss in total kinetic energy for fluid passing through the intersection. In such conditions the insertion of a static device could result in a more stable flow pattern, such that fluid exiting the intersection does so with higher kinetic energy.

A recent NIH Initiative (NHLBI-HV-04-01 Pediatric Circulatory Support) called for development of novel, innovative approaches to circulatory support for children with functional single ventricle using technology that is easy to use, rapidly deployed, with minimal prime volumes, and minimal risk of infection, bleeding or thrombosis. A pump according to one embodiment of the present invention fulfills some or all of the approaches.

Various embodiments of the inventions described herein address some or all of the conditions described above, in both novel and unobvious ways.

SUMMARY OF THE INVENTION

A novel expandable rotary blood pump designed specifically to augment cavopulmonary blood flow in patients with a univentricular Fontan operation. The device would be percutaneously applied, and intended to provide temporary support up to 2 weeks duration. Longer support with this type of device is possible, either by periodic exchange of the device through its catheter sheath, or with bioengineering design which improves length of use to longer time periods (months), or permanently.

The pump disclosed in some embodiments herein is built upon a similar foundation of optimizing TCPC flow. However, this concept has advanced this knowledge further by applying rotational energy to a central stabilizing body which is expanded and freely suspended within the lumen of the TCPC, independent of the vessel walls in order to stabilize (static) or augment (rotational) existing cavopulmonary blood flow.

Another aspect of some inventions disclosed herein concerns the structure and use of a passive (static) flow stabilizing element. This element can be placed within the junctions of fluid flowpaths to decrease turbulence and the energy losses that result from the turbulence.

One aspect of the present invention pertains to a method for pumping blood in the circulatory system of an animal. Some embodiments include providing a pumping element defined as a body of revolution about an axis, the body having a maximum diameter relative to the axis. The pumping element is positioned at a junction of at least two pathways in the circulatory system, the axis being generally aligned with a first pathway. Rotation of the positioned pumping element induces flow of blood from the first pathway and centrifuges blood into the second pathway.

Another aspect of the present invention pertains to a method for assisting the heart of a patient. Some embodiments further include providing a rotatable pump percutaneously insertable into the patient. Yet other embodiments include connecting the superior vena cava of the patient to the pulmonary artery of the patient. Still further embodiments include placing the pump at the junction of the SVC and PA and rotating the pump to increase the energy of the blood in the PA.

Yet another aspect pertains to an apparatus for pumping blood in an animal. Some embodiments include an outer cage movable from a substantially cylindrical stowed position to a deployed position and having a midsection that is substantially open to flow of blood in the deployed position. Yet other embodiments include a pumping element rotatable within the outer cage, the pumping element including a circumferentially-continuous flexible outer member supported by an inner cage in the deployed position, the pumping element having a distal end, a proximal end, and a deployed midsection of greatest diameter intermediate of the distal and proximal ends.

Still another aspect of the present invention pertains to an apparatus for pumping blood in an animal. Other embodiments include an outer tube having a central axis, the outer tube having a first wall extending along a first length, the first wall including a plurality of first slots, each pair of slots defining a first filament therebetween, the first region capable of movement from a stowed position to a bulging shape in a deployed position upon application of an axial load. Yet other embodiments include an inner tube, the inner tube having a second wall and fitting within the outer tube, the second wall including a second region capable of movement from a stowed position to a bulging shape in a deployed position upon application of an axial load. Preferably, the bulging shape of the inner tube fits within the bulging shape of the outer tube.

Another aspect of the present invention pertains to an apparatus for pumping blood in the pathways of an animal. Some embodiments include means for centrifugally flowing blood toward a first pathway. Yet other embodiments include means for axially flowing blood within a second pathway and toward the centrifugal means and means for protectively containing the centrifugal means and the axial means within a junction of the first pathway and the second pathway.

Yet another aspect of some embodiments of the present invention pertains to apparatus and methods for imparting a predetermined axial displacement into a pumping device having both stowed and deployed positions. Various embodiments pertain to pumping devices that are normally biased to the stowed position, as well as those embodiments that are normally biased to the deployed position. The displacing apparatus is preferably moved in a direction orthogonal to a central rotational axis of the pumping device, and converts that motion to relative motion along the axial direction. In one embodiment, the displacing mechanism includes a pinned linkage which is moved from a first position to a second position. Each of the first and second positions are established by mechanical stops that prevent excessive movement toward the desired position.

It is appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is excessive and unnecessary.

BRIEF DESCRIPTION OF THE DRAWINGS

FIG. 2: Microaxial pumps of fixed radius and small diameter may require an occlusive mechanism to prevent recirculation around the pump (balloon illustrated). Combined with the pump, this is obstructive to flow in the event of device failure. Flow rate is inherently higher in the inflow and outflow regions to deliver an equivalent volume that the larger diameter vessel would normally carry. There is potential for flow stasis.

FIG. 3: A folding propeller pump occupies minimal vessel cross-sectional area and is less obstructive. Flow is non-compressive across the vessel lumen. The vessel wall serves as the "housing" for the pump.

FIG. 20 is a comparison of total pressure (Pa) within flow field between cases without the presence of any device [A], with the presence of a static device [B], and with the device rotating at 5,000 rpm [C]. Some of the numbers shown in this figure refer to total pressure contours.

FIG. 21 is a comparison of velocity magnitude (m/s) of flow field between cases without the presence of any device [A], with the presence of a static device [B], and with the device rotating at 5,000 rpm [C]. Some of the numbers shown in this figure refer to velocity contours.

FIG. 22 is a comparison of turbulent kinetic energy ($m^2/s^2$) within flow field between cases without the presence of any device [A], with the presence of a static device [B], and with the device rotating at 5,000 rpm [C]. Some of the numbers shown in this figure refer to kinetic energy contours.

FIG. 23 is a side elevational view of an apparatus according to another embodiment of the present invention and shown in the deployed position.

FIG. 24 is a cross sectional view of the apparatus of FIG. 23 as taken along line 24-24.

FIG. 25 is a view of the apparatus of FIG. 23 as viewed along line 25-25 of FIG. 23.

FIG. 26 is a cross sectional view of the apparatus of FIG. 25 and shown in the stowed position.

FIG. 31 is a top perspective view of the apparatus of FIG. 31a.

FIG. 33a is a side elevational view of a pumping apparatus according to another embodiment of the present invention.

FIG. 33b is a view of the apparatus of FIG. 33a showing flow streamlines

FIG. 34b is an enlargement of the mid portion of the apparatus of FIG. 34a.

FIG. 34c is a cross sectional enlarged view of a portion of the apparatus of FIG. 34a.

FIG. 35b is an enlargement of the mid portion of the apparatus of FIG. 35a.

FIG. 35c is a cross sectional enlarged view of a portion of the apparatus of FIG. 35a.

FIG. 41b is a partially transparent pictorial representation of a portion of a medical procedure subsequent to that of FIG. 41a.

FIG. 43 is a side elevational view of a membrane for a pumping element in the stowed position according to one embodiment of the present invention.

FIG. 44 is an enlarged cross sectional view of a portion of the apparatus of FIG. 43 as taken along line 44-44.

FIG. 45 is an enlarged cross sectional view of a portion of the apparatus of FIG. 43 as taken along line 45-45.

FIG. 46 is a side elevational view of a portion of the apparatus of FIG. 43, shown in the deployed position.

FIG. 47 is a cross sectional view of a portion of the apparatus of FIG. 46, as taken along line 47-47 of FIG. 46.

FIG. 48 is a cross sectional view of a portion of the apparatus of FIG. 46, as taken along line 48-48 of FIG. 46.

DESCRIPTION OF THE PREFERRED EMBODIMENT

Figure 1C:
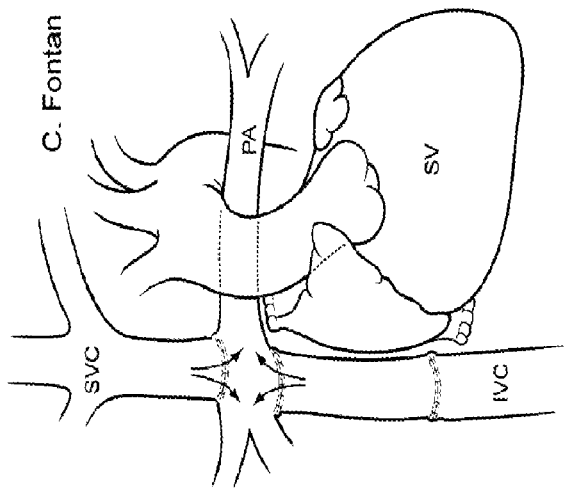
FIGS. 1*a-c*: Schematic representations of a known surgical method.

For the purposes of promoting an understanding of the principles of the invention, reference will now be made to the embodiments illustrated in the drawings and specific language is used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention is described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only. Further, with discussion pertaining to a specific composition of matter, that description is by example only, and does not limit the applicability of other species of that composition, nor does it limit the applicability of other compositions unrelated to the cited composition.

One embodiment of the present invention pertains to the use of a device that provides an increase in energy to fluid flowing within a conduit, and especially for fluid flowing within a T-shape or X-shaped fluid junction. In one embodiment, the device falls within the broad class of a von Karman viscous pump. In yet other embodiments, the device broadly resembles a centrifugal rotor (which can be one sided or two sided, and further can be symmetrical or asymmetrical about a plane perpendicular to the rotational axis). The device rotates within the fluid junction, and viscously induces flow along the inlet (the flowpath of the inlet preferably being generally parallel to or generally coaxial with the rotational axis of the device), and delivers fluid at a higher energy level to one or more outlets (which are preferably arranged perpendicular to the rotational axis). Energy is imparted to the fluid by viscous effects along the device pumping surfaces.

In one embodiment, the pumping device is circular, arranged in either a planar or conical shape. As used herein, the word "conical" includes both straight surfaces and curved surfaces (which can be curved either concave or convex). In yet another embodiment, the device includes back-to-back conically shaped surfaces. In some embodiments, the surfaces are mirror images about a central plane. In yet other embodiments, the shape of the pumping surface on one side of the plane is more acute than the conical angle on the other side of the plane. In yet other embodiments, the shape of the pumping device can be altered, such that for certain conditions, the relative flow contributions from two, facing inlets can be altered, and further the overall pumping capacity of the device can be increased or lowered.

In addition, a pumping element, especially a viscous pumping element, can be designed as a body of revolution. In such embodiments, a body describing the surface of the pumping element is defined by a line (of any type, including straight, curved, and combinations of both) that is revolved around an axis. Preferably the radial distance of the line from the axis increases monotonically from a hub toward a section of maximum diameter, which can be a midsection, or which can be proximate to the other hub. As the pumping element rotates, flow is centrifuged from the region of maximum diameter. This centrifuged flow will induce flow along the pumping surface from the nearby regions of lesser radius.

Various embodiments described herein pertain to a pumping element positioned at a junction of pathways. Preferably, the pumping element is positioned such that its axis of rotation is generally aligned with a first pathway from which flow is to be induced. It is understood that this alignment need not be perfect, and in those embodiments in which the pathways are within the circulatory system of an animal, it is recognized that the pathways are of a generally irregular shape, with little or no symmetry (in contrast to those embodiments which are positioned within hydraulic lines of mechanical devices). Further, it is preferable that the fluid being centrifuged away from the midsection region of maximum diameter (which can range anywhere from a sharply pointed vertex to a substantially rounded waist), such that fluid is centrifuged into a second pathway. Preferably, a streamline of flow exiting from the section of greatest diameter will point toward an inlet of the second pathway. In this manner, a particle of fluid leaving the pumping element is directed into the second pathway. In yet other embodiments, the pumping element is aligned such that a normal vector emanating from the region of greatest diameter points toward the inlet of the second fluid pathway. It is preferably, but not required, that a particle of fluid, or the pumping surface at the greatest diameter, have a "quote of sight" into the second pathway. With any of the alignments previously discussed, fluid flowing from the pumping element should efficiently be directed into the second pathway. However, yet other embodiments of the present invention recognize that the alignment with the second pathway may centrifuge fluid particles at the walls of the junction, and further recognize that the inlet of the second pathway, especially in animals, is irregular in shape.

As used herein, junctions of fluid pathways are sometimes described in terms of their general resemblance to letters, such as the letters "Y," "T," and "X." In such cases, it is recognized that such shorthand descriptions describe physiological junctions within an animal body that include irregularity. As one example, a "Y" junction is any type in which one pathway bifurcates into two primary (in terms of diameter) pathways, regardless of the angle between the first pathway and either of the bifurcated pathways, or of the angle between the bifurcated pathways. In some cases, the "Y" shape can describe a relatively small angle from the one pathway to the bifurcated pathways, therein resembling two "V" shapes sharing a common central path. As yet another example, a "T" shape generally describes one pathway that buts into a second pathway, regardless of the angle of intersection. As yet another example, an "X" shaped junction includes four pathways coming together, which can include one pathway supplying the other three pathways, or two pathways supplying the other two pathways or three pathways supplying a single pathway.

Although what is shown and described herein are various embodiments of pumping devices implantable in an animal body, the invention is not so limited, and also contemplates pumping devices provided generally within fluid systems. Further, it is understood that the term "animal" includes human beings.

In patients with a univentricular Fontan operation, there is no subpulmonary ventricle to pump systemic venous blood through the lungs. A pump designed to serve in this role would beneficially function to lower systemic venous pressure into a more physiologic range, while at the same time improve transpulmonary blood flow and ventricular filling of the single ventricle, thus improving cardiac output. No such device currently exists. The pressure range which would be helpful to augment cavopulmonary blood flow is on the order of 2-20 mmHg, a range which is one order of magnitude less than the pressure generated by existing commercially available blood pumps designed to provide systemic circulatory support (50-100 mmHg). One consideration is the use of an actuator disk working along the lines of a Von Karman Viscous Pump principle: a rotating disk that moves fluid in axially, and moves it out in a radial direction. Such pumps are sometimes described as having mixed flow, such that a streamline exiting the greatest diameter of the pumping element has flow components in both the radial and axial directions.

One embodiment of the present invention pertains to novel pump design. Other embodiments pertain to a pump that applies to a novel anatomic region (partial or total cavopulmonary connection). In one embodiment, the pump has a single impeller which can induce inflow from 2 opposing ends (inferior and superior vena cava), and provide outflow in perpendicular opposing ends (right and left branch pulmonary arteries). The pump is non-occlusive and facilitates flow under any circumstance. In some embodiments, the pump is shaped such that when not rotating, it has a stabilizing effect on flow in the intersection of the cavopulmonary connection. The pump does not require a barrier to recirculation, can be placed percutaneously, is non-invasive, has low preload and afterload dependence, and provide pressure augmentation in a useful range. The pump is an example of an "expandable catheter-based rotary blood pump" which does not currently exist commercially.

Figure 1B:
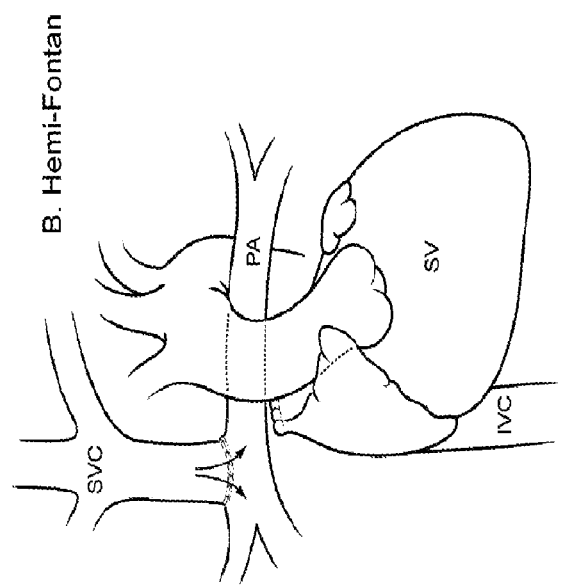
Figure 1A:
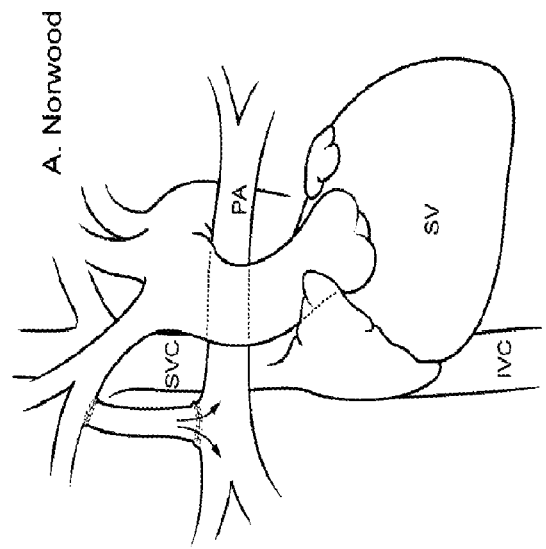

With regards to FIGS. 1a, 1b, and 1c there are shown several stages of repair to a heart having a univentricular congenital defect. In the most common form, Hypoplastic Left Heart Syndrome, the left ventricle fails to form in a way that is ever functional. In the first procedure, which must be performed in the first weeks of life, the right ventricle is converted to pump blood to the body rather than to the lungs (FIG. 1a). Blood flow to the lungs must be secondarily derived from a high-pressure systemic arterial source via a systemic-to-pulmonary arterial shunt to overcome the potential for elevated pulmonary vascular resistance (PVR) in newborns. Unfortunately, the use of a shunt results in severe hypoxemia and creates an inherently unstable parallel arrangement of the systemic and pulmonary circulations which must be delicately balanced. Consequently, this procedure is notorious for instability and mortality of 20 to 30%. Inter-stage mortality (between $1^{st}$- and $2^{nd}$-stages) is also exceedingly high (4-24%). This high risk of death is a manifestation of an inherently unstable circulation, for which the shunt is the common denominator. Decompensation is characteristically sudden, unpredicted, and without discernible cause. In contrast, stability and survival after the second- and third-stage operations is much better, which coincides with takedown of the shunt.

At the expense of providing a reliable source of pulmonary blood flow, the shunt creates 4 potentially lethal physiologic consequences: the single ventricle must (1) support both pulmonary and systemic circulations in an unstable parallel arrangement by (2) pumping twice normal volume, and perform this doubled workload under the harsh conditions of (3) severe hypoxemia ($PaO_2$ 30-40 mmHg) and (4) impaired myocardial coronary perfusion due to (a) decreased diastolic blood pressure from shunt run-off and (b) increased myocardial wall tension due to ventricular volume overload. Synthetic shunts also have risk of lethal thrombosis. Any change affecting the balance of the parallel circulations requires compensation elsewhere to restore equilibrium. Dangerous positive physiologic feedback loops escalate instability: Hypoxemia leads to lung hypoperfusion, and thus worsening hypoxemia; conversely, "high" $PaO_2$ (>40 mmHg) dilates the pulmonary circulation, leading to lung overperfusion and further elevation of $PaO_2$—at the expense of systemic perfusion. Life-saving management may require counterintuitive and harmful intervention, including further reduction of inspired oxygen (at times below 0.21) and hypoventilation. Not surprisingly, neurocognitive impairment subsequent to Stage-1 repair is common. Paradoxically, the shunt induces and exacerbates the conditions that mandate its use in the first place: hypoxic pulmonary vasoconstriction and pulmonary hypertension. These impair postnatal pulmonary vascular maturation, and elevate early and late basal PVR which impair subsequent Fontan status. Ironically, shunt physiology may make the timing for Stage-2 conversion later than it might be otherwise, and may worsen candidacy for stage-2 and -3 Fontan conversion.

The second and third operations (FIGS. 1b and 1c collectively) represent "staged Fontan conversion". The problematic shunt is disconnected, and blood flow to the lungs is converted to a low pressure systemic venous source by connecting the vena cavae directly to the pulmonary arteries (a cavopulmonary connection). Blood flow to the lungs and body is restored to a more stable series arrangement, as found in normal two-ventricle physiology. However, the sole energy source for pulmonary blood flow is relegated to systemic venous pressure, which must be significantly elevated (10-15 mmHg) in order for flow to occur. This introduces two new problems which are responsible for the majority of Fontan-related health concerns: 1) systemic venous hypertension, and 2) suboptimal ventricular filling and cardiac output. In the second operation (FIG. 1b), the superior vena cava (SVC) is connected to the pulmonary artery as the sole source of pulmonary blood flow. This stage is typically performed beyond 4 months of age, when the risk of elevated pulmonary vascular resistance is low. Inferior vena caval (IVC) flow continues into the common atrium, leaving a significant right-to-left shunt and hypoxemia, which continues to exacerbate pulmonary hypertension. Pulmonary blood flow is transitioned to nonpulsatile, steady-flow perfusion, which increases pulmonary vascular impedance.

In the third operation (FIG. 1c), IVC (and thus total) venous return is diverted to the pulmonary arteries. The lower half of the body and the splanchnic circulation are exposed to elevated venous pressure. Marginal candidates, in whom IVC pressure exceeds 12-15 mmHg, may suffer from low cardiac output, impaired hepatic function, and develop ascites and effusions. The ideal age and timing for this stage is unknown and varies amongst institutions. However, the age at which Fontan completion is tolerated appears to be getting lower. This trend is interesting because it is unexpected based on clinical dogma, yet the equal or better outcomes are unexplained. It is plausible that infants, including neonates, may be equally or better capable of adapting to and tolerating chronically elevated systemic venous pressure.

The second and third procedures cannot be performed in the newborn due to the unsolved problem of achieving passive blood flow through vasoreactive neonatal lungs. It is important to note, however, that neonatal complete Fontan repair has never been attempted. Because of the clinical evolution of Fontan repair, it is assumed that this physiology is not possible in very young infants. Advocates of staging cite the difficulties in performing Stage 2 procedures in infants less than 4 months of age; however, this occurs under conditions of continued hypoxemia and continued stimulus for elevated PVR due to IVC flow into the systemic circulation, and therefore is not a reasonable comparison to total Fontan conversion in which there is no right to left shunt.

The second and third-stage procedures generally cannot be safely performed as a single conversion for two reasons. First, an acute elevation in total systemic venous pressure in the highly compliant systemic venous territory causes significant volume shift. Without support, the acute administration of volume required to sustain cardiac output leads to edema and untenable tissue malperfusion, especially when superimposed with capillary leak and third spacing after cardiopulmonary bypass. If bridge support were provided to allow neurohormonal, interstitial, and oncotic adaptation to this transition, it could occur safely in one stage. Second, an abrupt change from a volume-overloaded to a volume-normal heart with a non-compliant ventricle is not desirable. Staging allows for the ventricle to remodel more gradually to a volume "normal" state. This exemplifies a paradox of staging: the physiology has to adapt back to normal after it has previously maladapted to abnormal circumstances. Stage-1 pathophysiology (ventricular overload and hypertrophy) creates conditions that mandate staged conversion; without it, conversion may not necessarily need to be staged. Studies have shown that ventricular function improves after volume unloading, and that earlier volume unloading improves late Fontan outcome. A mathematical model predicts that small body surface area or lower age has minimal effect on a univentricular Fontan circulation. These findings support early staged Fontan conversion—or, no staging at all. Fontan physiology may be feasible much earlier than thought.

In a univentricular Fontan circulation, 4 segments of the circulation become critically interdependent: 1) systemic venous pressure, 2) cavopulmonary gradient (an anatomic issue), 3) transpulmonary gradient (a physiologic issue), and 4) ventricular filling pressure. The pressure differential across these 4 sites is relatively small (~12 mmHg), the majority of which occurs across the lungs. Seemingly trivial pressure loss (2-5 mmHg) in any of these sites has magnified impact on the remainder of the circulation. Similarly, a hydraulic energy gain of only 2-5 mmHg in this region will significantly improve circulatory status (for example, a 2-5 mmHg reduction in venous pressure and a commensurate increase in ventricular filling pressure). Presumably, some form of chronic physiologic adaptation occurs in response to Fontan conversion, including neurohormonal and interstitial/oncotic pressure change, but these mechanisms are unknown. Because timing for Stage-2 conversion has historically been dictated by PVR status, the nature of systemic adaptation, the time required for adaptation, or whether elevated central venous pressure is feasible in the neonate or young infant in response to Fontan conversion have never been relevant.

The Fontan circulation is characterized by coexisting systemic venous hypertension and relative pulmonary arterial hypotension due to absence of a subpulmonary ventricle. Therefore, it stands to reason that the addition of a subpulmonary power source would reverse these problems and re-create normal 2-ventricle physiology. Opposed to the current complex staged surgical approach with its multitude of risks and pathologies, this concept is sensibly based on the stability of two-ventricle physiology for which the body is teleologically programmed to function optimally.

The paradigm would shift to facilitate the transition from an assisted univentricular circulation (cavopulmonary pump+ single ventricle) to an unassisted univentricular circulation in which the lungs are perfused by venous pressure alone. Cavopulmonary assist can be applied at any point and in any combination in the palliative sequence, or late after Fontan completion. For cavopulmonary assist to be implemented, 2 things should occur: 1) a unique pump should be developed; 2) the transition to Fontan physiology should be characterized.

Although patients with failing Fontan physiology exhibit features typical of congestive heart failure (decreased tissue/organ perfusion, increased tissue/organ water), the causative factor is not necessarily a reflection of intrinsic myocardial dysfunction. Doppler myocardial echocardiographic studies in Fontan patients (with normal systolic function) demonstrate that diastolic dysfunction is a result of chronically reduced filling rather than primary myocardial dysfunction. 70% of Fontan patients have preserved ventricular systolic function at late follow up. Stated otherwise, it can be said that other segments of the circulation are actually failing the Fontan heart. The position of the "failing Fontan" heart on the Starling curve is one distinction because cavopulmonary assist is based upon the tenet that a modest (2-5 mmHg) increase in ventricular filling will improve myocardial performance and cardiac output. Cavopulmonary assist can be applied preferentially to support inferior vena caval flow for adult patients with failing Fontan physiology, because the majority of their morbidity arises from the IVC territory and IVC flow accounts for the majority of systemic venous return. A device according to one embodiment of the present invention overcomes limitations in existing one-way microaxial design in that it prevents backflow pressure elevation in the opposing vena cava. It can be applied as bidirectional support (both SVC and IVC territories) including the potential for combined-stage Fontan repair in younger patients in whom SVC pressure and flow are more critical.

Not only is active cavopulmonary assistance useful in patients with univentricular Fontan operation, it is also useful in patients with congestive heart failure. Such patients can benefit from active support of right ventricular function by a pump.

The hydraulic needs for right ventricle support are approximately $\frac{1}{5}^{th}$ of left ventricle support. A viscous impeller pump may be used to noninvasively support the right-sided circulation in patients with biventricular (normal anatomy) circulations. A percutaneously inserted viscous impeller pump according to one embodiment of the present invention positioned in the main pulmonary artery would reduce right ventricular afterload and promote myocardial recovery. It would also improve preload to the systemic ventricle and improve cardiac output. The pump can be deployed percutaneously in the catheterization lab or in the intensive care unit. The pump head would be positioned in the main pulmonary artery at the level of the pulmonary bifurcation using fluoroscopic guidance and hemodynamic indicators.

The viscous impeller pump could also be applied in the cardiac catheterization lab during interventional catheterization procedures in instances where acute right ventricular dysfunction occurs (for example during dissection of a right coronary artery) as a means of temporary percutaneous support. This could also be used adjunctively with intra-aortic balloon pump (IABP) support for support of the systemic circulation in the presence of left ventricular dysfunction. This would add to the cardiologist's armamentarium of therapeutic options to stabilize patients in the catheterization lab.

At least one aspect involving the use of a viscous impeller pump according to one embodiment of the present invention for temporary right heart support is that it would minimize or eliminate the need for surgical placement of a permanent RVAD, translating to a dramatic reduction in morbidity and mortality risk. Bi-VAD (LVAD+RVAD) support is associated with significantly more complications that LVAD support alone. Often, the clinical decision as to whether RVAD support may be necessary cannot be made until several days after LVAD support has been instituted; this time window is precarious in terms of patient health and ability to withstand another major open-heart surgical procedure. RVAD support may not be needed long-term, as the right ventricle will likely recover sufficient to function adequately, even if its contractility does not fully normalize. The time estimate for right heart function to recover is usually less than 1 week in a large clinical series.

Asymmetric viscous impeller geometry and/or asymmetric surface vane expression (height, curvature) can be used in the pulmonary artery bifurcation to augment pulmonary blood flow. Asymmetry favors axial inflow from one direction and still augments bidirectional outflow in the pulmonary artery bifurcation. An impeller and cage according to one embodiment of the present invention does not represent a source of obstruction when rotating, and obstruction is minimal when not rotating.

Cavopulmonary assist, both active (powered) and passive (static), is conceptually unique; a device temporarily supports the circulation in a location where no ventricle will recover to assume its function in the former case, and a static device that reduces turbulent losses in the latter case. For a pump to safely augment cavopulmonary blood flow, unique anatomic, physiologic, and bioengineering issues are to be considered. Relative to the systemic circulation, blood pressure within the cavopulmonary connection of a univentricular Fontan circulation is very low. Furthermore, a pressure boost of only 2-5 mmHg may be all that is necessary (or ideal) to augment cavopulmonary flow and significantly improve hemodynamic status. The upstream source of inflow is steady-flow systemic venous return; there is no volume reservoir for the pump inlet to draw from. Thus, there is higher than usual risk of vessel collapse and cavitation due to pump suction. Additionally, no natural occlusive mechanism (valve) is present within a cavopulmonary connection to prevent recirculation around the pump body. Finally, it is useful that the venous pathways remain unobstructed during pump deployment (rotating or stationary) and after withdrawal.

A microaxial pump has been successfully adapted to assist cavopulmonary flow in mature animals as proof of concept for cavopulmonary assist. These can be percutaneously placed, function in the intravascular space, do not utilize extracorporeal circuits or externalized cannulae, do not require a volume reservoir or atmospheric vent, provide continuous flow (as in a cavopulmonary connection), provide a wide range of flow rates, require minimal set-up time and no fluid/blood prime, and do not require valves. A recent NIH Initiative (NHLBI-HV-04-01 Pediatric Circulatory Support) called for development of novel, innovative approaches to circulatory support for children with functional single ventricle using technology that is easy to use, rapidly deployed, with minimal prime volumes, and minimal risk of infection, bleeding or thrombosis. A pump according to one embodiment of the present invention fulfills some or all of the requirements.

All clinically available devices produce pressures and flows far in excess of the desired range for cavopulmonary support. Experience with mechanical support of SVP is mostly limited to systemic support (the wrong target) using extracorporeal membrane oxygenation (ECMO) as salvage. Survival for SVP patients supported by ECMO is poor (40-50%), with hemorrhage, thrombosis, and stroke as causes of failure. There is no device suited to support cavopulmonary blood flow in patients with SVP and there is a clear need for more effective options.

One embodiment of the present invention pertains to an innovative pump. Factors to be considered to safely provide cavopulmonary assist include: 1) hydrostatic pressure is very low in the cavopulmonary circulation; 2) a pressure boost as small as 2-5 mmHg may be all that is required. This is supported by the clinical improvement observed in patients who undergo Fontan conversion to streamline their venous pathways by a seemingly trivial, yet useful 2-5 mmHg. 3) the upstream source of inflow is steady-flow systemic venous return; 4) there is no volume reservoir for the pump inlet to draw from; 5) there is higher than usual risk of vessel collapse and cavitation due to pump suction; 6) no natural occlusive mechanism is present in the venous pathway to prevent recirculation around the pump; 7) it is helpful that the caval pathways remain unobstructed during device deployment, and after the pump is withdrawn. These factors can be significant, and they are entirely new to the circulatory support field.

A percutaneous, expandable, folding propeller pump with protective cage may represent one solution (FIG. 3). It could be relatively easily applied in the catheterization lab or intensive care unit with femoral or jugular venous insertion and heparin anticoagulation, and managed similar to an intra-aortic balloon pump. As a bridge-to-recovery, it would reduce systemic venous pressure (2-5 mmHg) and improve ventricular filling (2-5 mmHg) which would, in turn, reduce capillary and interstitial hydrostatic pressure and improve end-organ perfusion. As a bridge-to-transplant, it would increase the likelihood of surviving the wait for a donor organ and improve physiologic status at the time transplant occurs.

A pump 20 according to one embodiment of the present invention includes some or all of the following features: (1) Simplicity: few moving parts, noninvasive placement, rapid deployment/removal, no blood or crystalloid prime, minimal preparatory time (<1 hr), transportable, employing a reliable propulsion method; (2) relatively flat pressure-flow hydraulic characteristics which provide a modest pressure rise and high-volume flow similar to normal right ventricular hemodynamics; (3) Low preload and afterload dependence; (4) minimal venous pathway obstruction; (5) An anatomic or complex artificial barrier to recirculation of blood around the pump is not necessary: the pumping surfaces provide a functional barrier to backflow spanning the vessel lumen; (6) Lower foreign surface area to blood volume ratio compared to other devices; (7) Reduced anticoagulation requirement due to lower foreign surface exposure and maximally exposed endothelial lined surfaces. 8) Rotor exchangeability, without need for surgery or anesthesia, may reduce risk of thrombogenicity and other complications. The rotor can also be exchanged to match variable physiologic demands.

Majority IVC support using an asymmetric impeller may be sufficient in the adult failing Fontan because the majority of their morbidity arises from the IVC territory. A pump according to one embodiment of the present invention is applied similar to a central venous catheter or intra-aortic balloon pump and can be percutaneously placed in the ICU setting or in a catheterization lab using Seldinger technique (needle over wire). For neonatal application, majority SVC, or bi-directional pump support (SVC+IVC) may be helpful.

A folding propeller blood pump can be used for circulatory support. As applied in the descending thoracic aorta, however, this device has limitations: 1) it is capable of maximally augmenting systemic arterial pressure at a limit of 20 mmHg, which is marginal for systemic support; 2) it reduces upstream pressure, thereby reducing cerebral and coronary perfusion pressure. For cavopulmonary assist, a pressure gradient in the 2-10 mmHg range is preferred under healthy conditions, but pressure capability in higher ranges may be necessary to overcome increased pressure head (pulmonary hypertension, 40+ mmHg). Furthermore, a reduction in upstream systemic venous pressure is desirable and has no deleterious consequences (with the exception of negative pressure).

Folding propellers may be less efficient from a hydraulic standpoint due to limited blade width and surface area. A degree of fluid slip is desirable, however, because it reduces preload and afterload dependence, thereby reducing risk of excessively negative upstream pressure (suction, vein collapse, cavitation) or excessively positive downstream pressure (perfusion lung injury). It also eliminates the critical problem of venous pathway obstruction. Furthermore, an artificial barrier to prevent recirculation is not required; the propeller blades provide a functional rather than physical barrier to backflow which spans the vessel lumen.

Figure 4A:
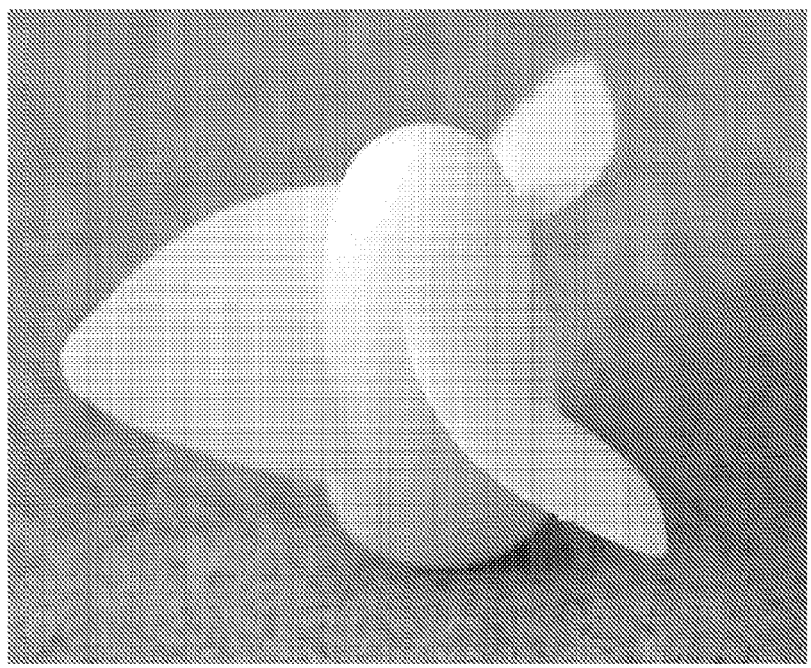
FIGS. 4*a* and 4*b*: Plastic propeller according to one embodiment of the present invention.
Figure 4B:
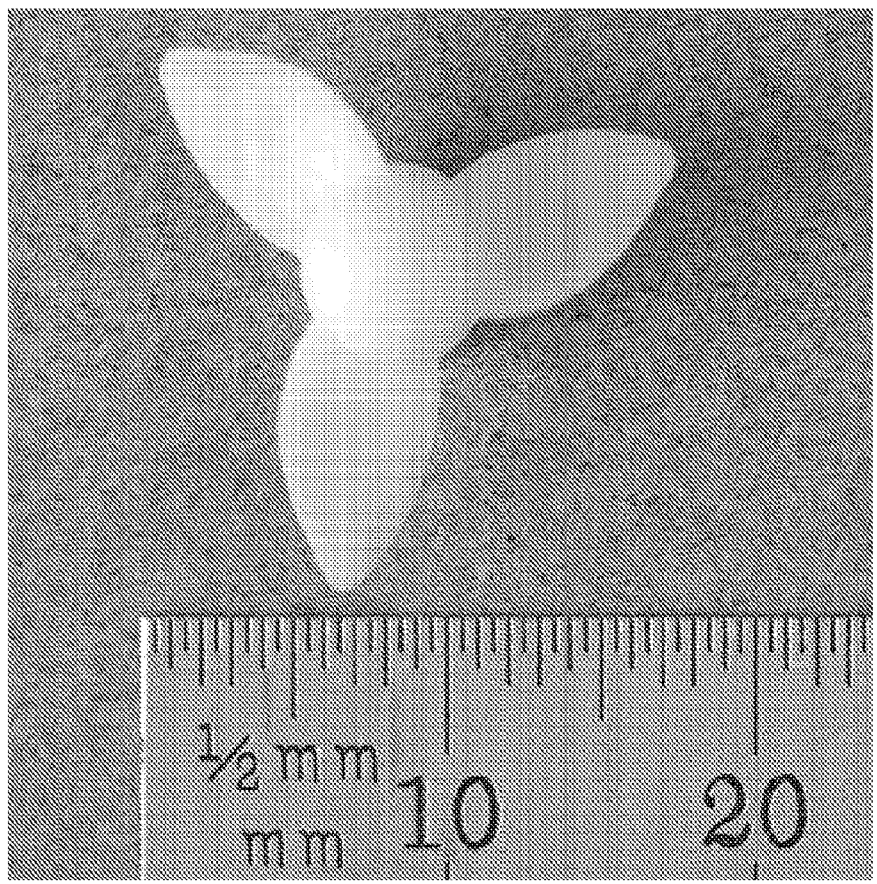

A pump with a non-folding blade design (as shown in FIGS. 4a and 4b) was tested. It was, however, otherwise similar in dimension to a folding blade design (narrow blade width, relatively wide hub). Pump performance was not characterized in the presence of the expandable protective cage. Folding propellers have relatively flat pressure-flow characteristics which can provide the modest pressure boost and high-volume flow necessary to gently augment cavopulmonary flow. It has previously been demonstrated that a relatively simple 2-bladed propeller will function within the desired pressure and flow range to provide this type of support. What follows is the hydraulic and hemolysis performance of a 3-bladed prototype.

Pump scale and operating range were specified to provide unidirectional cavopulmonary assist in adults with univentricular Fontan circulations (Table 1). Tip-to-tip diameter is 20 mm with maximal blade width of 6 mm and hub diameter of 6 mm (FIGS. 4a and 4b).

TABLE 1

Design specifications for the propeller pump.

| Specification | Adult |
|---|---|
| Flow (LPM) | 0.5-4 |
| Pressure rise (mmHg) | 5-20 |
| Rotational speed (RPM) | 3-9,000 |
| Design flow (LPM) | 1.5 |
| Vessel Diameter (mm) | 30 |

The prototype was mounted within a pipe conduit (30 mm internal diameter) of a hydraulic flow loop for pressure-flow performance measurement. A blood analog fluid (water/glycerin 60/40; viscosity 3.34±0.152 cP; specific gravity 1.08±0.002) was used to match the properties of blood. Flow rates were varied by increasing and decreasing resistance in the loop. The pressure differential was determined using a diaphragm pressure transducer. Pressure rise and flow rate were simultaneously measured under steady-flow conditions.

Hemolysis studies (n=2) were performed using the same hydraulic flow loop in accordance with American Society for Testing and Materials standards F1841-97 (Standard Practice for Assessment of Hemolysis in Continuous Flow Blood Pumps), F1830-97, and F756-00 under guidelines from International Workshops on Rotary Blood Pumps in 1988 and 1991. After baseline samples were collected, pump rotation was initiated and a flow rate of 2 LPM and rotational speed of 6000 RPM was maintained over 6 hours. Samples were collected hourly. Plasma free hemoglobin was calculated based on the weighted difference in absorbance. The normalized index of hemolysis (N.I.H) was calculated. Results of the testing are shown in FIGS. 5, 6a, 6b, 7, 8, and 9.

Figure 5:
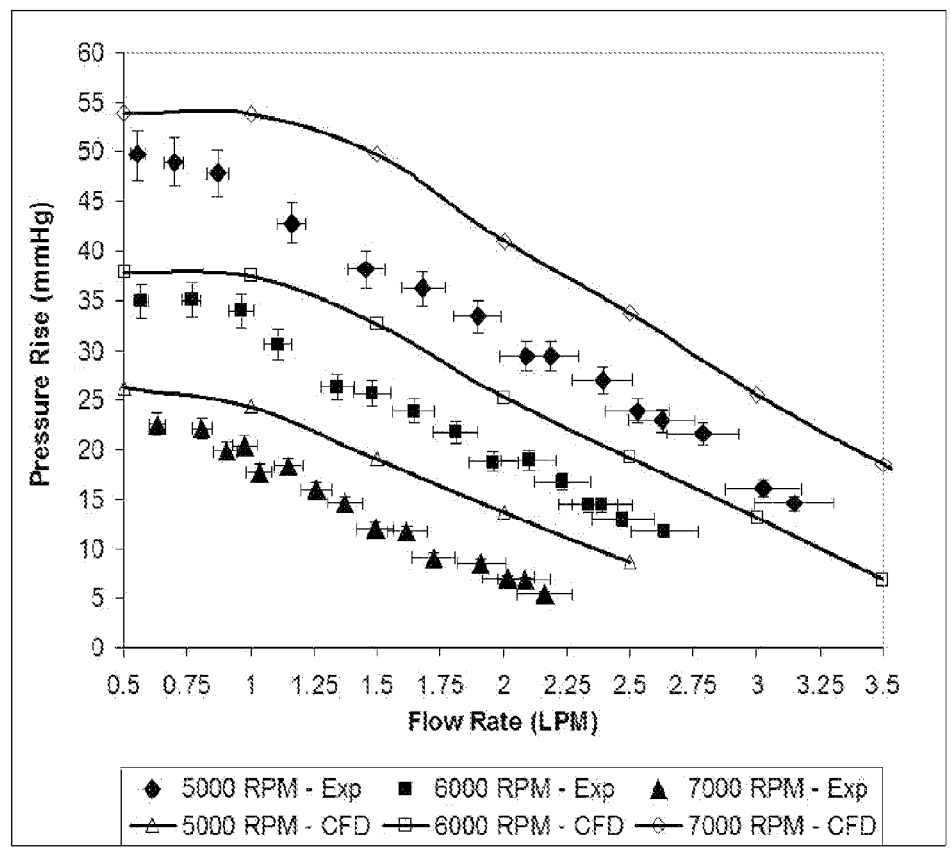
FIG. 5: Hydraulic performance of the pump of FIGS. 4*a* and 4*b*. Exp: experimental results. CFD: computational predictions.

Pressure rises were observed in the desired range of 5 to 50 mmHg and flow rates of 0.5 to 3.25 LPM at rotational speeds of 5000 to 7000 RPM (FIG. 5). Compared to numerical estimates, observed hydraulic performance was approximately 20% less than predicted, but closely correlated, especially at lower flow rates. This is explained by a difference in conditions between the numerical model and the experimental configuration: Blade tip clearance was 5 mm as tested, as opposed to 0.2 mm in the numerical model. Although the larger experimental gap clearance contributed to hydraulic energy loss, it may also reflect conditions that would be encountered in the clinical setting.

Figure 7:
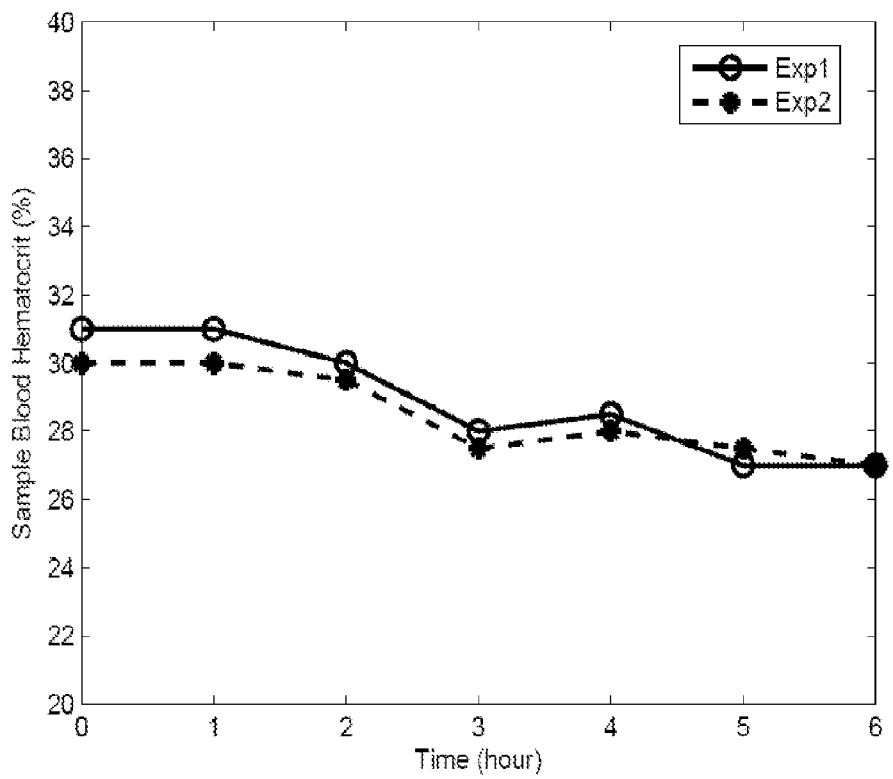
FIG. 7: Hematocrit during hemolysis experiments.
Figure 6A:
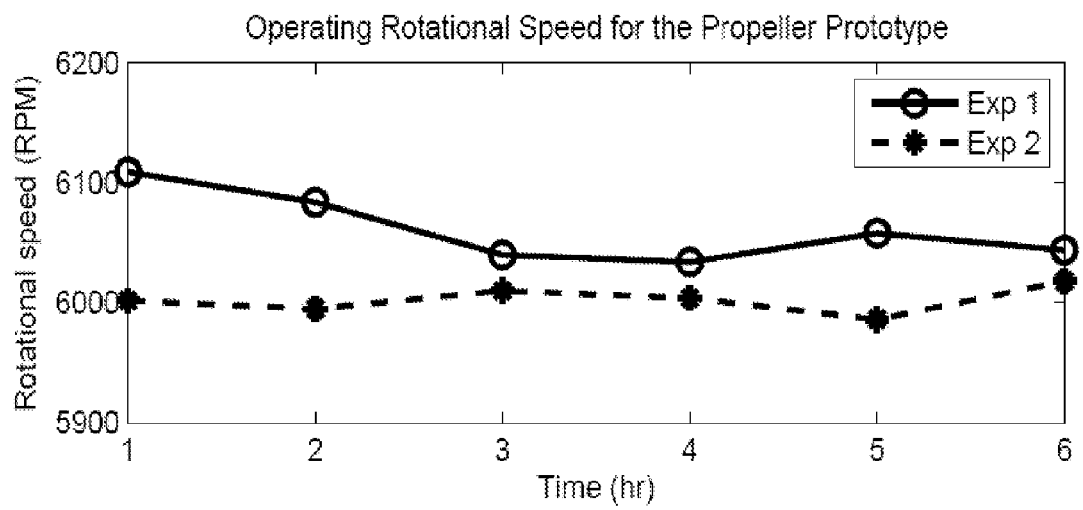
FIGS. 6*a* and 6*b*: Rotational speed, flow rate, and temperature data or the pump of FIGS. 4*a* and 4*b*.
Figure 6B:
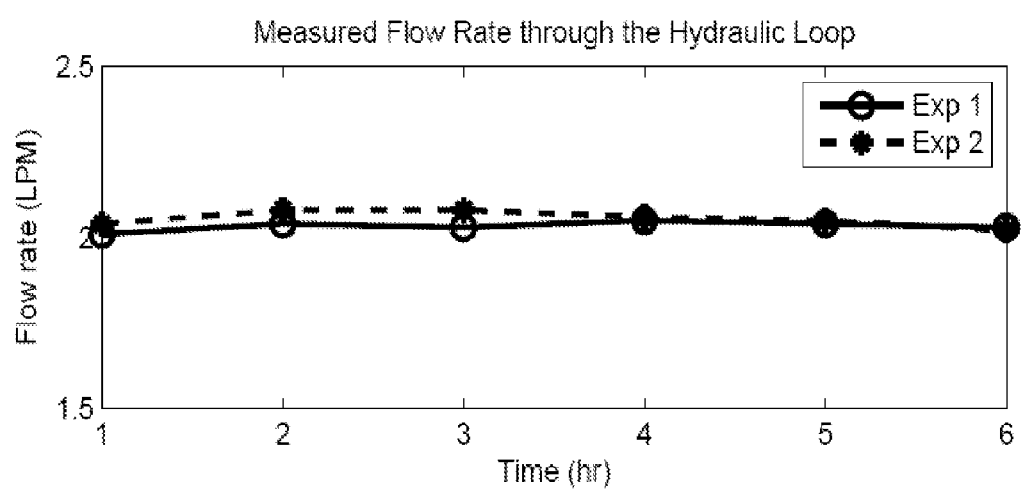
Figure 8:
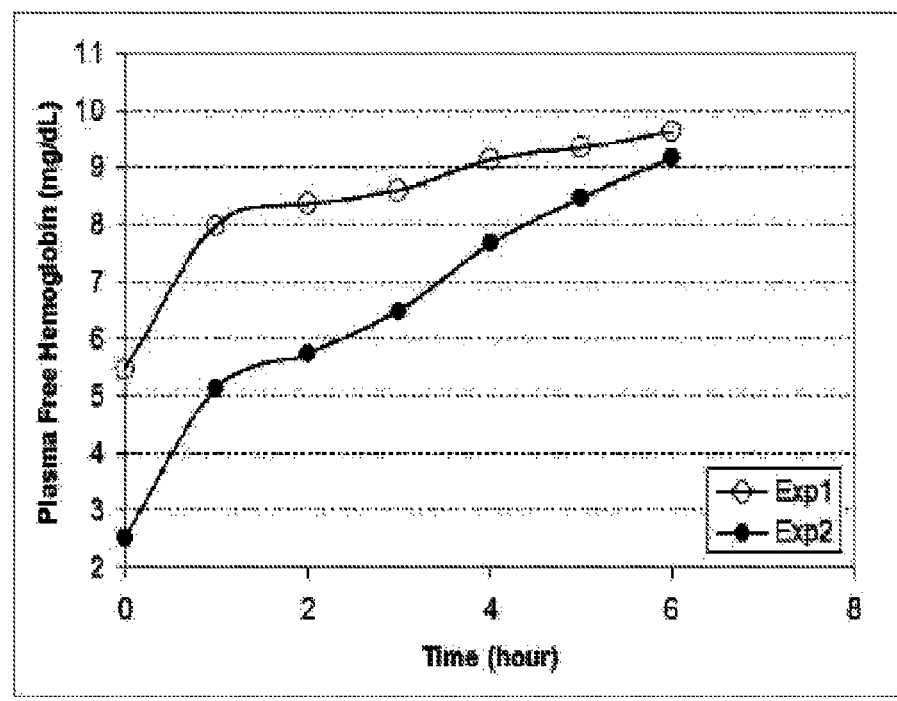
FIGS. 8 and 9: Plasma free hemoglobin (pfHb) and Normalized Index of Hemolysis (N.I.H) during hemolysis experiments.
Figure 9:
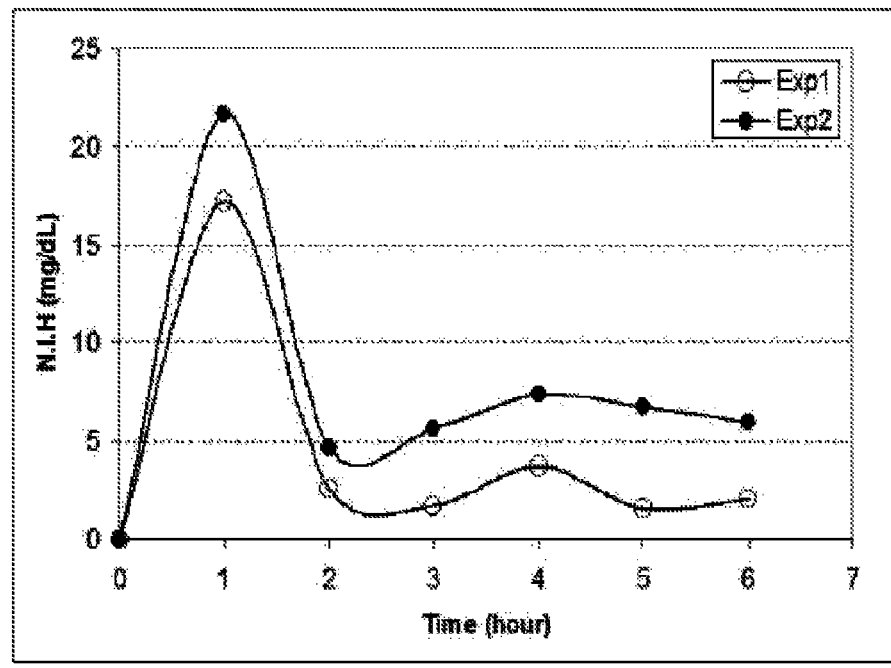

Rotational speed, flow rate, and hydraulic loop temperature over the duration of the experiments are shown in FIGS. 6a and 6b. Hematocrit remained between 27% and 30% with a slight decline over the 6 hour period (FIG. 7). Plasma free hemoglobin concentration rapidly increased in the first hour and then steadily, but much more slowly, increased hours 1-6 (FIGS. 8 and 9). Similarly, N.I.H. values spiked in the first hour and then remained consistently less than 10 mg/dL over hours 1-6. The increase in plasma free hemoglobin and N.I.H. values during the first hour are attributed to lysis of red blood cells due to rapid pump start-up secondary to instrumental limitations. Free hemoglobin levels less than 50 mg/dL are acceptable for device-related hemolysis, and levels less than 10 mg/dL are excellent.

Figure 10:
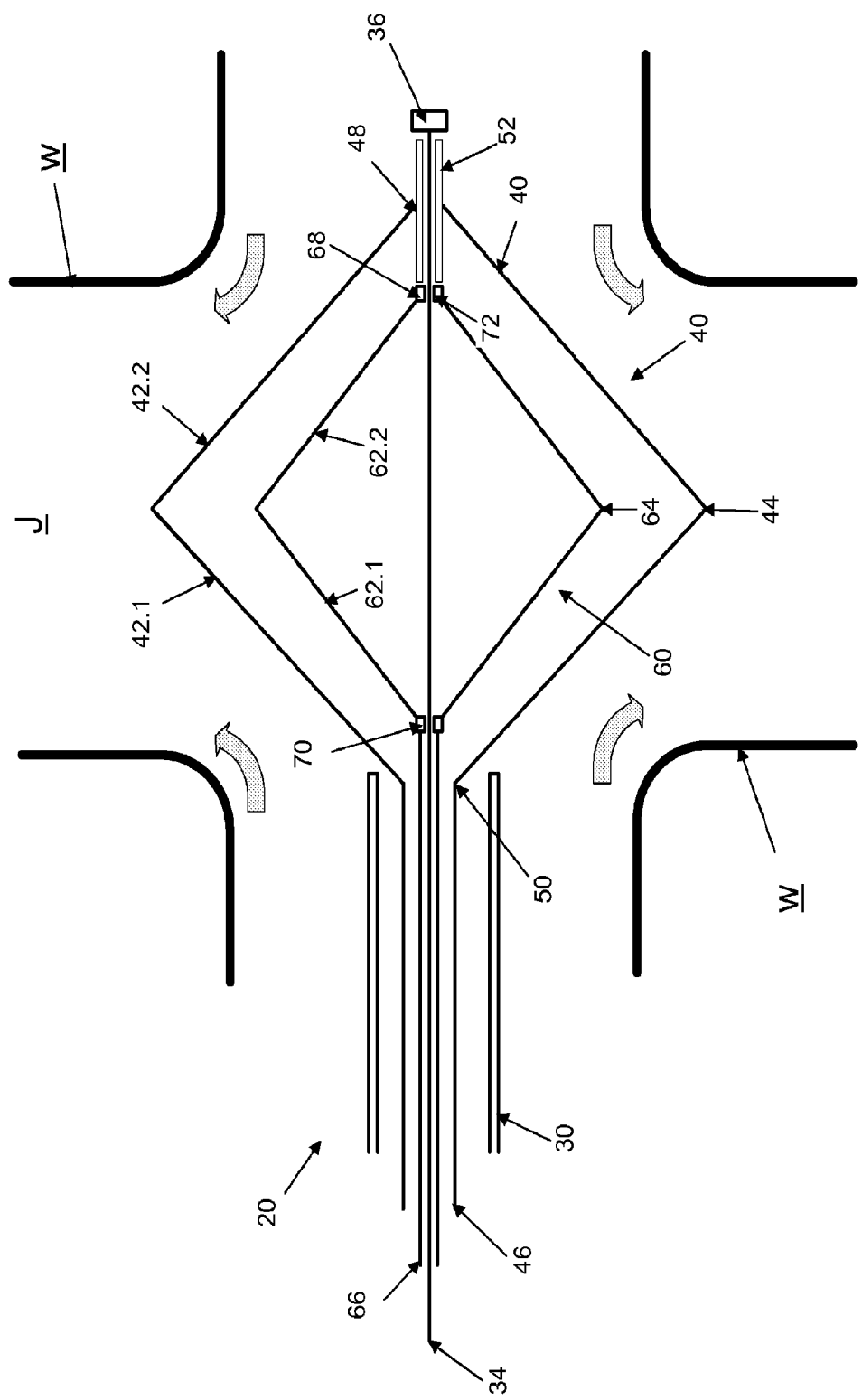
FIG. 10 is a schematic representation of a deployed pump assembly according to another embodiment of the present invention.
Figure 11:
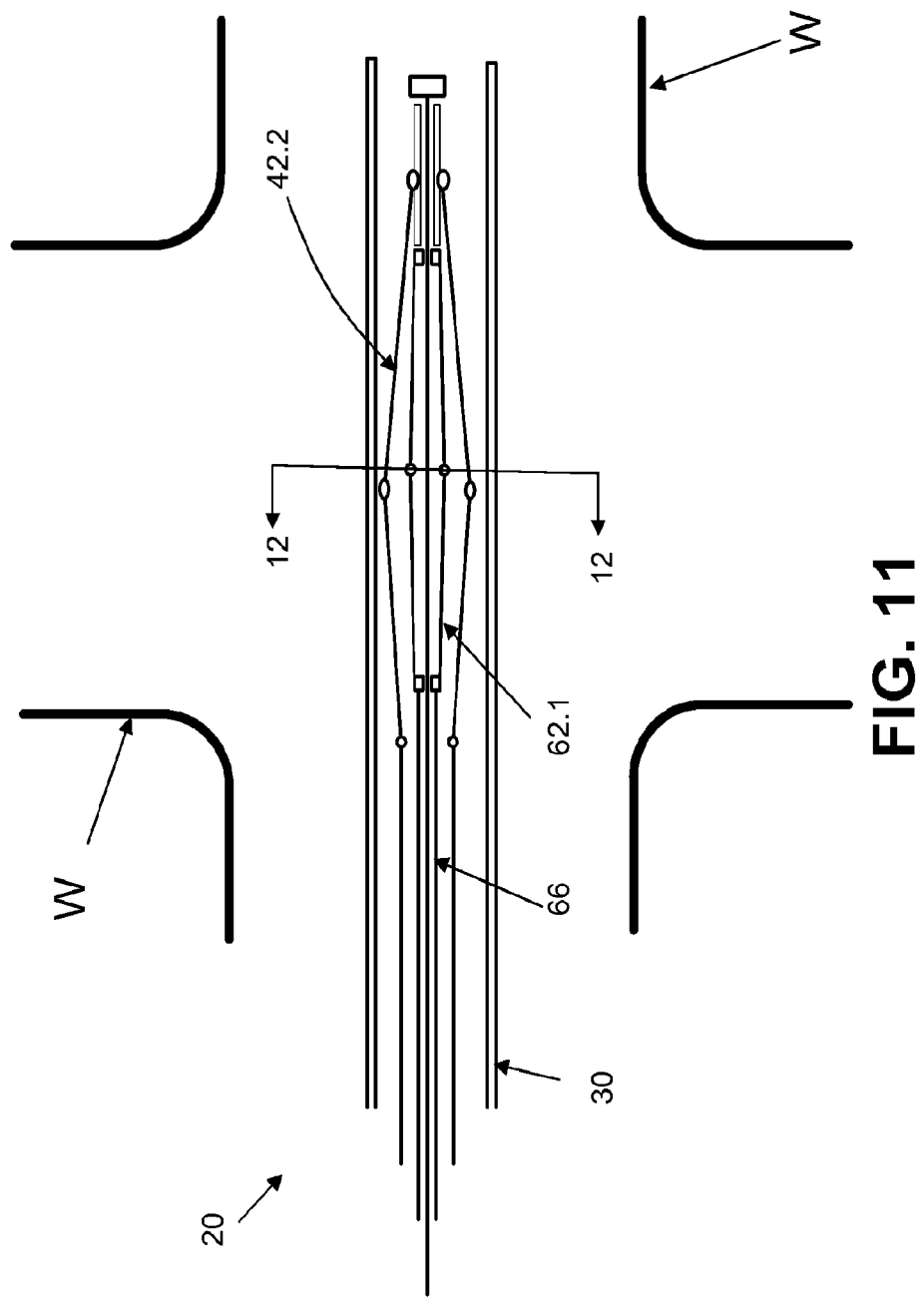
FIG. 11 is a schematic representation of the pump assembly of FIG. 10 in the stowed state.
Figure 12:
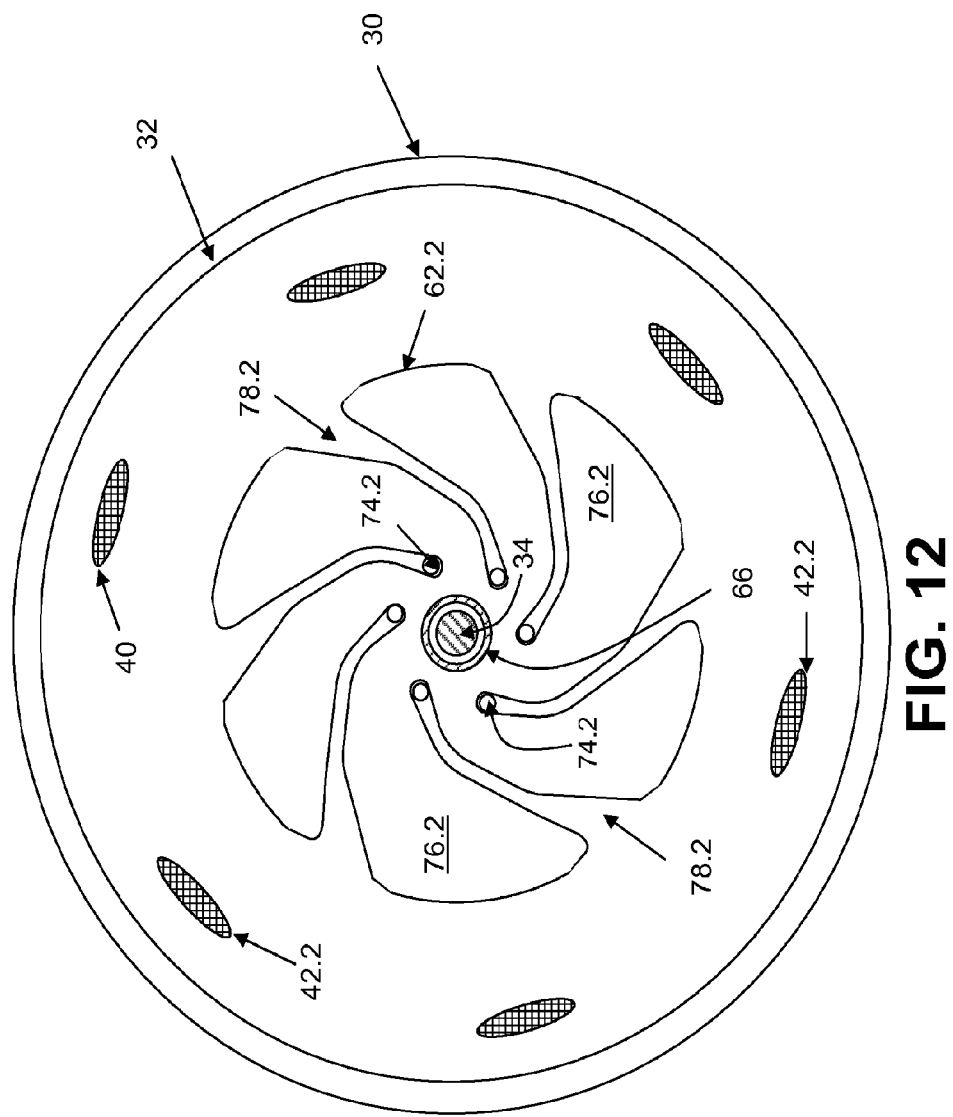
FIG. 12 is cross section representation of the apparatus of FIG. 11 as taken along line 12-12 of FIG. 11.

Yet another embodiment of the present invention pertains to a catheter-based rotary pump with a flexible drive wire contained within a catheter (see FIGS. 10, 11, and 12). The impeller 60 is manufactured of an injection molded biocompatible elastomer, such as silicone-based urethanes, or other pliable material so that it is flexible and has spines 74 (plastic or metal) that act 1) to reinforce the shape of the balloon and 2) as directional vanes to optimally channel fluid flow across the surface as the impeller 60 rotates. The impeller is able to change configuration from a generally collapsed low profile form (to allow percutaneous insertion and deployment) and can then expand in the proper location in a larger diameter central vessel near the heart through a shape ranging from small diameter spindle to bi-concave conical disk to relatively flat disk. Ridges or corrugations in the surface of the impeller/balloon are designed to optimize flow (minimize energy loss, minimize shear stress and hemolysis risk, maximize efficiency). The shape of the surface 62 would also be optimized for optimal flow (e.g. flat vs conical shape components).

The impeller/catheter assembly is surrounded by a protective sheath which would incorporate a protective expandable cage, which in some embodiments is constructed with memory retaining nitinol wire (similar in design to 2 back-to-back opposed vena caval filters). The protective cage centers the impeller in the cavopulmonary connection and protects the vessel wall from impeller touchdown and vessel wall damage. The external end (outside the body) of the catheter/sheath includes a sealed magnet which is bonded to the drive wire. The placement of an alternating electric field around the magnet would spin the magnet, thus spinning the drive wire, and thus spinning the impeller inside the body to induce movement of fluid. An internal motor powered by wire or transcutaneous source or other drive system (skeletal muscle assist via remotely linked reservoir) may apply. The catheter drive wire in some embodiments of the present invention includes a self-contained purge system to lubricate the drive wire and prevent entry of clotting elements into the bearing supporting the impeller. The device would be employed similar to an intra-aortic blood pump with percutaneous insertion and radiographic/echocardiographic placement/positioning.

FIGS. 10, 11, 12, and 14 schematically depict a cavopulmonary pump assembly 20 according to one embodiment of the present invention. Assembly 20 includes a catheter 30 that percutaneously delivers a cage assembly 40, pump 60 and central rod 34 to a pulmonary junction J within the body. As best seen in FIG. 10, pump assembly 20 is shown in its deployed state within the walls W of a pulmonary junction J. Flow approaches the junction from both the right and left, and exits from the top and bottom, as indicated by the curved directional arrows.

A central rod 34 with an endstop 36 extends distally from the end of the sheath of catheter 30. A stationary cage assembly 40 extends from the distal outlet of catheter 30, and generally spans the distance from catheter 30 to endstop 36. A plurality of diverging proximal protective members or filaments 42.1 extend radially outward from catheter 30 to respective vertices 44. A plurality of converging, distal protective members 42.2 converge from vertices 44 to flexible or hingable connections 48 on a cylindrical spacer 52. Cage 40 is adapted and configured for articulating joints, including joints fabricated from material that is readily and repeatedly elastically deformable (and for applications generally in the field of pumps, hinge joints, pin joints, and the like) or otherwise flexible connections 50 to an actuating cylinder 46 contained within sheath 30.

Pump assembly 20 further includes a pump 60 that is rotatably supported about central rod 34. Pump 60 includes a proximate pumping surface 62.1 that is connected by otherwise flexible connection 70 to a central rod 66. Proximal pumping surfaces 62.1 extend in a diverging pattern from connections 70 to a plurality of flexible vertices 64. A second, distal pumping surface 62.2 extends from vertices 64 to flexible connections 68 to a deployment stop 72.

FIG. 11 shows pump assembly 20 in the stowed position. Assembly 20 is adapted and configured such that cage 40 and pump 60 fit within the cannula of sheath 30. Protective members 42.1 and 42.2 collapse radially inward toward central rod 34. In one embodiment, protective members 42.1 and 42.2 pivot about vertices 44, connections 48, and attachment 50. In yet other embodiments, protective members 62.1 and 62.2 are sufficiently flexible to permit a radially inward collapse. Further, driving surfaces 62.1 and 62.2 of pump 60 likewise collapse radially inward toward central rod 34, by either pivotal connections 64, 68, and 70, by flexibility in the members themselves, or combinations of both.

Pump 20 transitions from the stowed condition of FIG. 11 to the deployed condition of FIG. 10 by pushing actuating cylinders 66 and 46 and central rod 34 from the distal end of catheter 30. Protective members 42.1 and 42.1 extend out of catheter 30, these protective members expand because of a residual memory in their material (such as by use of Nitinol®). Likewise, as pumping surfaces 62.1 and 62.2 extend outwardly from the distal end of sheath 30, these pumping surfaces likewise extend radially outward based on their material memory (such as by use of Nitinol®).

Actuating cylinder 46 can be pushed within sheath 30 until spacing member 52 contacts endstop 36 of central rod 34. Actuating cylinder 66 can be pushed within actuating cylinder 66 until actuating stop 72 contacts the other end of spacer 52. Spacer 52 establishes pump 60 within the inner volume of cage 40, with sufficient clearance from pumping surfaces 62.1 and 62.2 to protect the members 42.1 and 42.2, respectively.

FIG. 12 is a schematic representation of a cutaway of the stowed pump assembly 20. Both cage assembly 40 and pump 60 fit within the inner diameter of wall 32 of catheter 30. Protective members 42.2 of cage assembly 40 are located radially outward of pump 60. As shown in FIG. 2, one embodiment of cage 40 includes a plurality of six discrete protective members 42.2 arranged in a generally uniform circumferential pattern.

In one embodiment, pump 60 includes a plurality of support rods 74.2 that extend, when deployed, from vertices 44 to a hingable connection 68 at stop 72. Support rods 74.2 are attached to a flexible sheathing 76.2. The sheathing 76.2 provides most of the pumping surface 62.2. Support rods 74.2 can be configured with a circumferentially swirling pattern to act as discrete rotating pump vanes. In one embodiment, the flexible material 76.2 is fabricated from a biologically compatible elastomer. When stowed, the flexible sheath material 76.2 forms a plurality of fold spaces 78.2, similar in concept to folds of a stowed umbrella. Although FIG. 12 shows only a cutaway across the distal pumping surface 62.2, the proximal pumping surface 62.1 likewise includes a plurality of rods or filaments 74.1 that both support and fold a flexible material 76.1.

Figure 14:
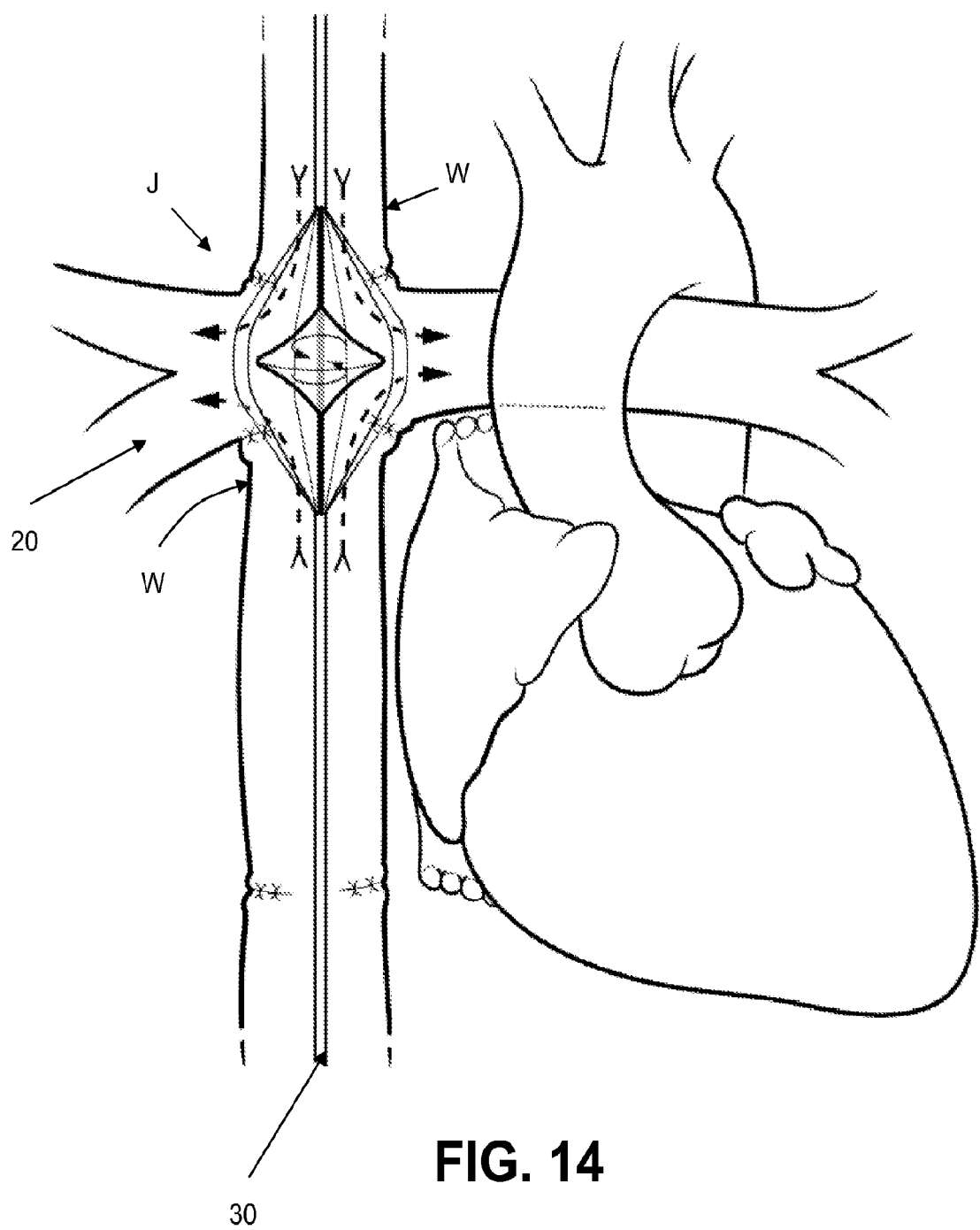
FIG. 14 is a schematic representation of a pumping assembly according to one embodiment of the present invention as deployed in a junction of an animal circulatory system.

FIG. 14 is a pictorial representation of a pumping assembly 20 installed within a junction J of circulatory pathways. Apparatus 20 has been percutaneously inserted into a patient and directed toward a junction J of pathways within the circulatory system. Although the pathways depicted pertain to a circulatory system having a Fontan repair, the present invention is not so limited and applies to junctions of any type within the circulatory system and further, for those embodiments not having medical application, pertains to the junction of two fluid pathways of any type. Cage 40 has been expanded to protect the walls W of the junction from the pumping element 60 rotating therein. Rotation of pumping element 60 induces axial flow in the vertical direction (as depicted in FIG. 14) toward the maximum diameter at the midsection of pumping element 60. Flow exits impeller 60 in a direction substantially orthogonal to the direction in which fluid is induced by the viscous pumping action of rotor 60.

Figure 13:
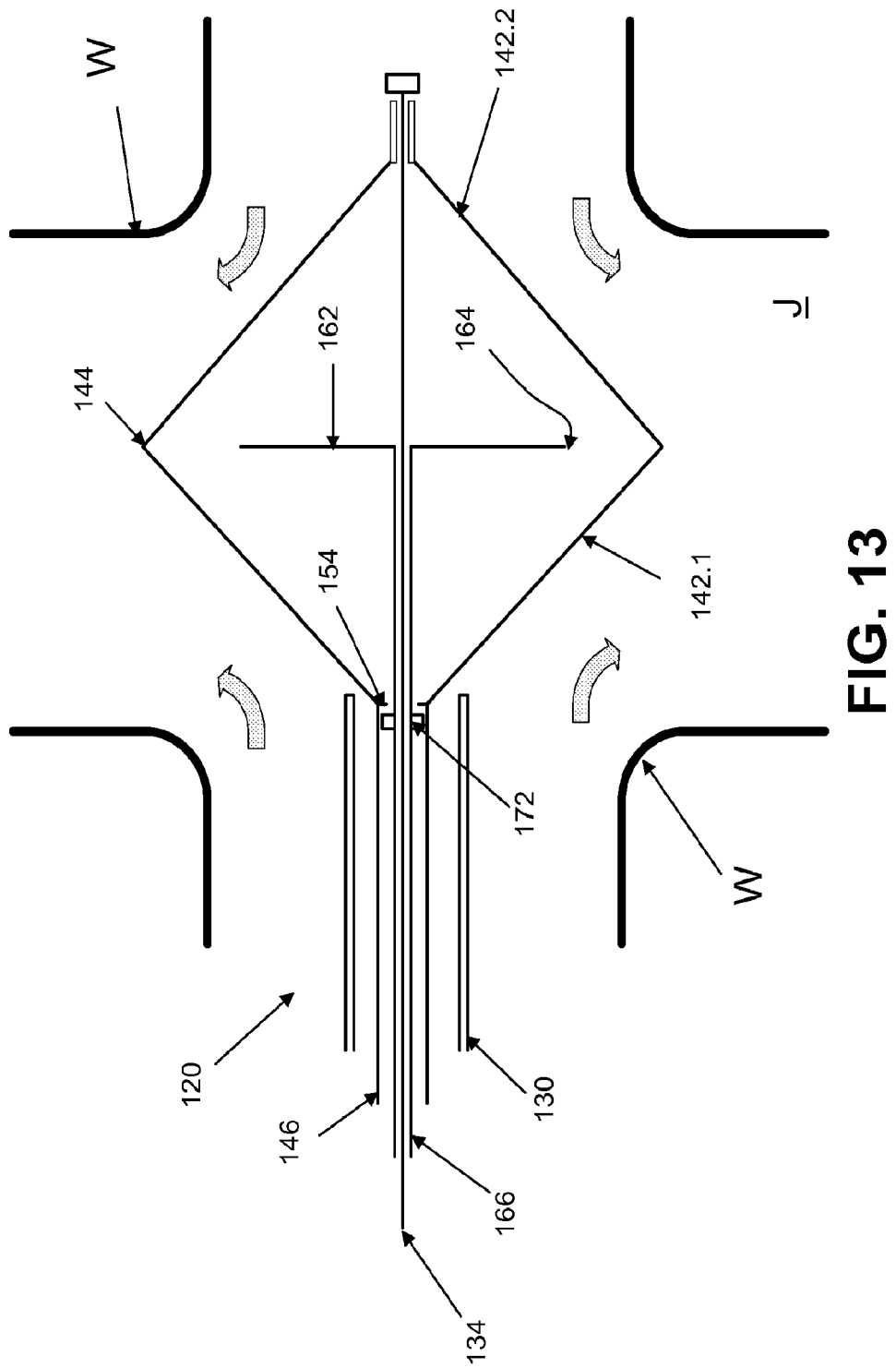
FIG. 13 is a schematic representation of a pump assembly according to another embodiment of the present invention.

FIG. 13 shows a cross sectional representation of a pump assembly 120 according to another embodiment of the present invention. Pump assembly 120 is the same as pump assembly 20 except that pump 40 includes a single pumping surface 162. As depicted in FIG. 13, pumping surface 162, when deployed, is shaped as a substantially flat cylindrical disk. Rotation of disk 162 induces upstream flow through protective members 142.2 toward the distal side of pumping element 162. Likewise, rotation of disk 162 about central rod 134 induces flow through static protective members 142.1 toward the proximal surface of disk 162. Viscous effects of circular plate 162 rotating within the flow field induce flow radially outward from edge 164 in the vicinity of vertices 144.

Pump 120 differs from pump 20 with regards to the apparatus for stopping deployment of pump 160 relative to cage 140. Actuating cylinder 166 of pump 160 has attached to it a stopping surface 172 that, during full deployment, abuts against a nonrotating surface 154 of cage 140.

Figure 15:
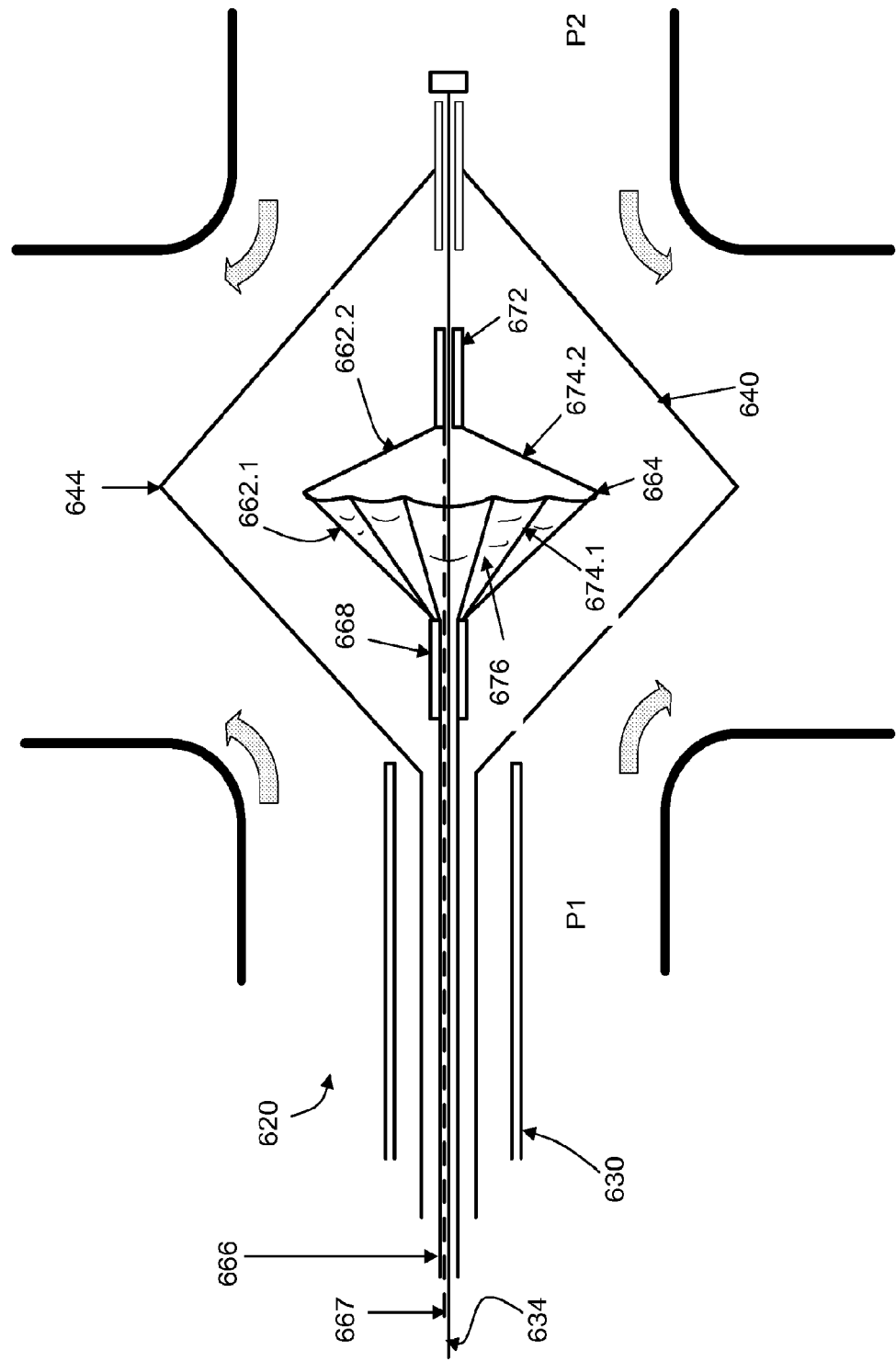
FIG. 15 is a partial cross sectional schematic representation of an apparatus according to one embodiment of the present invention.

FIG. 15 depicts an asymmetric, actuatable-shape pump assembly 620. Pump 660 of assembly 620 includes a proximal pumping surface 662.1 that comprises a plurality of support rods 674 extending from a central attachment plane 670 of actuating cylinder 666. A flexible material 676 is coupled to each of rods 674 in a manner similar to that of an umbrella.

A pair of support rods 674.2 are coupled at opposite points to pumping surface 662.1 at one end, and at the other end to respective attachment points 670 on collar 672. Further attached to collar 672 is an actuating cable 667. By preferential relative movement of rod 667 relative to cylinder 666, collar 672 can be made to move closer to or more distant from the proximal end of pumping surface 662.1. Thus, the shape of pumping surface 662.1 can be varied from that of a narrow angle conical shape to that of a flat plate, depending upon the relative lengths of rod 674.1 and 674.2. Further, since rods 674.2 are not coupled to a flexible surface 676, relatively little fluid is induced from inlet passage P2 as compared to the flow induced from inlet passage P1.

Although what has been shown and described in FIG. 15 is a pump 660 including a single pumping surface 662.1, the present invention also contemplates those embodiments in which there are a plurality of support rods 674.2 attached to an interconnecting flexible sheet 676. In such embodiments, depending upon the relative lengths of rods 674.1 and 674.2, a two-sided pump (similar to pump 20) is provided, with a pumping surface 662.2 that is actuatable over a range of positions.

The actuator disc impeller 62 can have composite flexible design features incorporated into its design so that its hydraulic performance may vary under different fluid preload and afterload conditions (to optimize performance and minimize cavitation risk).

Pumps 20 can provide "phasic" operation when the impeller speed is intentionally pulsed—so that the pump delivers flow in a physiologic pulsatile flow pattern (which also provides a reason for flexible composite design to limit cavitation risk and optimize performance under varying load conditions). The shape of the impeller may be intentionally modified during use (from spindle to cone to disk shape, and vice versa) to vary the degree of support that is desired or during weaning of pump support for withdrawal.

The drive system for the pump has been mostly described as a using a catheter and self-contained flexible drive wire system, but it could also be powered by alternative sources such as transcutaneous transmission of power to a fully implantable and retrievable system, or a magnetically driven system.

Figure 16:
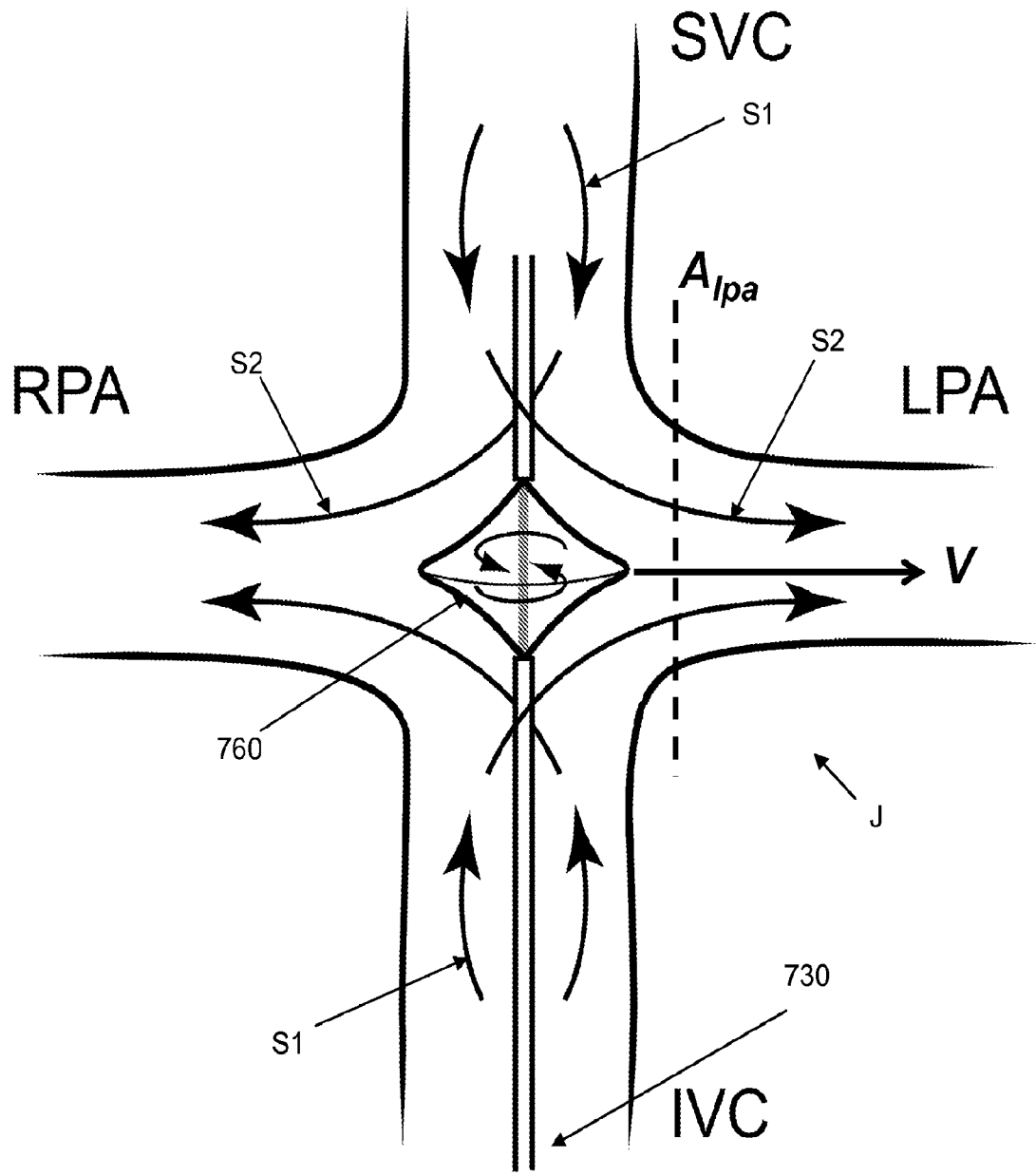
FIG. 16 a schematic representation of a pumping assembly according to one embodiment of the present invention as deployed in a junction of an animal circulatory system.
Figure 17:
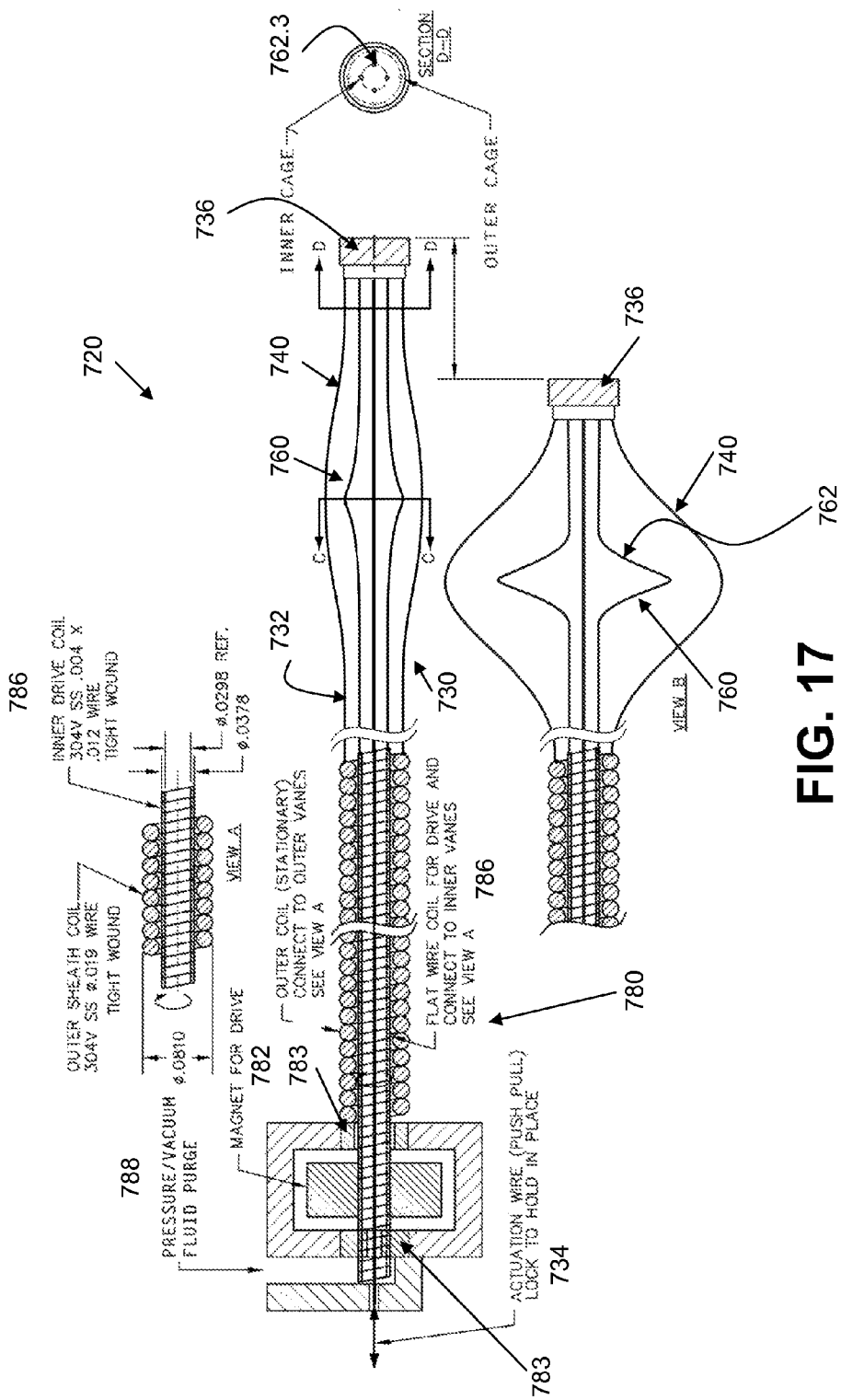
FIG. 17 is a schematic representation of an apparatus according to another embodiment of the present invention.

A pump assembly 720 according to another embodiment of the present invention is schematically depicted in FIGS. 16 and 17. The discussion that follows pertains to pump assembly 720. It is understood that the descriptions to follow are by way of example only, and are not intended to be limiting.

The rotary pump platform includes a sheath 732 and catheter mixed flow rotor 760, an external motor 782, drive wire system, fluid seal and purge system 788, and electronic control console. The rotor is affixed to a flexible drive wire 734.2, covered by a polyurethane sheet. A magnet, in closed continuity with the sheet, is bonded to the external end of the drive wire; when placed in an alternating electric field, magnet rotation spins the pump head internally. A purge system is connected to the sheet covering the drive wire to provide fluid seal integrity and lubricate the drive wire. An external motor source is preferable as it will allow a small diameter and provide uniformity of this catheter-based pump. Devices which utilize a self-contained motor (Impella) are limited by motor size, are non-uniform in diameter, and may not be able to achieve the small diameter range (9 F, 3 mm, or less) for adults, children, and neonates.

The pump head includes an inner rotating impeller 760 and an outer stationary cage 740 (FIG. 17). Each is preferably constructed from concentric tubes (metal or plastic) modified so that, upon axial compression, they expand in unison, with little or no interaction, to a predetermined configuration. The inner frame, covered with a membrane 61 (similar to a catheter balloon), assumes a bi-conical disk shape. This may be as simple as a longitudinally-ridged injection molded balloon, whose shape and surface is predetermined. The membrane elastomer is a primary blood contacting surface; the underlying frame has little or no blood contact. The outer cage 740 expands spherically as an open cell with little or no flow interference, to center the impeller for TCPC flow transfer and protect the vessel wall. The catheter 730 has 3 components: 1) an outer sheet 732 (catheter), an intermediate flexible drive coil 786, and a central actuator wire 734 to control opening and closing. Bearings 783 at 2 points provide coaxial position of the impeller relative to cage.

Two bearing/seals 783 are located between the rotating impeller hub and stationary catheter/cage. The self-contained purge system 788 preferably: 1) enhances seal integrity; 2) lubricates the drive coil and seals; and 3) prevents accumulation of blood elements between rotating and stationary components. Intrinsic leak rate (~3 cc/hr) of the purge system 788 may be utilized for local heparin delivery within the device, to increase concentrations at the bearings and reduce the systemic heparin requirement.

In yet other embodiments, purge system 788 also includes a pressurizing system that permits the imposition of a controlled internal pressure within the volume of rotor 740. In such embodiments, apparatus 720 includes an external source of pressure, one or more pressure transducers, and a pressure controller. The source of pressure can be a liquid or a gas (such as helium).

Pressure from the external source can be provided through a lumen within the drive cable 734. The drive cable includes an outlet aperture located anywhere along the expandable length of rotor 760. In such embodiments, rotor 760 is covered with a continuous membrane 761 preferably fabricated from an elastomeric material. The hub ends of the membrane 761 are preferably sealed to the outer diameter of a deployable inner tube 763 or an equivalent deployable cage assembly 762.

The collapsed:expanded ratio of this device allows a percutaneous size ($\geqq$9 French, 3 mm dia.) smaller than other blood pumps. One microaxial device proposed for infant (non-percutaneous) systemic support is 12 F (12 French, 4 mm dia., Impella 2.5™ by Abiomed™ which uses a barrier to recirculation (such as an aortic valve), and spins nominally at 25-50K rpm). In one embodiment, the adult device is 9 F/3 mm dia. closed, 18 mm impeller dia. open. Cage 740 diameter will be 20% greater than impeller, providing a safe clearance gap. Length of the pump head is ~4-5 cm closed and ~3 cm open. Impeller diameter is no greater than 80% vena caval diameter. Neonatal device dimension is neonatal device dimension is about 6 French or 2 mm outer diameter in the stowed position.

Insertion and removal of device 7230 is similar to a central venous catheter. A sheath is placed in the femoral or internal jugular vein using Seldinger technique. After fluid purge priming and systemic heparinization, the pump is advanced and positioned via fluoroscopy, echocardiography, or palpation (surgical implantation) in the TCPC. After connecting to a motor source, the impeller 760 and cage 740 are opened by a predetermined axial displacement within device 720, either in tension or in compression, and the pump 760 rotated. A locking mechanism visually indicates deployment status. Evidence of pump function includes reduction in venous pressure, and improved systemic perfusion (blood pressure, urine output, acid/base status, etc). In the event of malposition, the device would be collapsed and repositioned. For removal, the pump is shut off, impeller 760 and cage 740 closed, and catheter and sheath 732 removed.

In event of rotation failure, a reasonable time interval (hours) will exist to address the problem with percutaneous intervention, rather than requiring emergency surgical intervention as may be required with a larger diameter microaxial device. Hemodynamics can be temporarily supported by fluid administration and inotropic support.

This intervention time period is a result of the minimal blockage presented by the pump 760 and cage assembly 740, even in the deployed position (as shown in FIG. 17). As best seen in section DD of that figure (and also represented by the cage structure 740 shown in FIG. 10), the deployed protective cage assembly 740 does not substantially obstruct any portion of the junction of the flowpaths. In preferred embodiments of the present invention, a pump assembly 720 (as well as 20 and other X20 variants) includes means for protectively containing a rotating pumping element. This means for containing (including cages 40, 740, and other X40 variants) include expandable (deployable) structures comprising wires or filaments (42, 742, and X42 variants) that define a volume in which the pumping element can safely rotate without striking walls W of any pathway at the junction J. Further, these wires or filaments are spaced apart circumferentially such that fluid particles pass easily in the spaces in between adjacent wires or filaments. In some embodiments, the ratio of circumferential spacing between filaments to the circumferential extent of a single filament is greater than about three to one, and preferably greater than about six to one.

Therefore, even when means (40, 740, and X40) for protectively containing the impeller are deployed, there is relatively little blockage of the junction of the pathways. This is in contrast to some known pumping devices that require substantial or complete blockage of the pathway, except for the pump.

FIG. 16 is a pictorial representation of a pumping element 760 placed within an "X" junction of the superior vena cava, inferior vena cava, right pulmonary artery and left pulmonary artery. For sake of clarity, cage 740 and other elements of device 720 have been omitted.

A rotating pumping element 760 is shown within a junction J of circulatory pathways. Pumping element 760 is being rotated by driving means acting within catheter 730. As element 760 rotates, flow S1 is induced in a generally axial direction in the SVC and the IVC toward junction J. This flow S1 moves along the curved pumping surfaces of rotor 760 toward a midsection of greater diameter. A particle of fluid exits the rotating midsection in a direction generally parallel to that of normal vector V that is normal to the surface of the midsection. As shown schematically in FIG. 16, this normal vector is preferably aligned with the center of the entrance area $A_{lpa}$ of the left pulmonary artery. Those of ordinary skill in the art will recognize that the irregular geometry of an animal circulatory system can make it difficult to define the entrance area, as well as the midpoint. Nonetheless, the midsection of pumping device 760 is oriented such that flow exiting the pumping element is encouraged to flow within the pathway of the LPA. For example, in some embodiments the geometry of the junction J may be such that the normal vector V impinges on a wall of the pathway, or even a wall of the junction, but nonetheless establishes a pressure gradient that results in flow into the desired pathway.

Further, yet other embodiments of the present invention contemplate rotating pumping elements 60 that are asymmetrical about a plane normal to the axis of rotation. In such applications there can be a difference in the induced axial flow S1 from the SVC as compared to S1 from the IVC, with the pumping element inducing less flow in one leading pathway relative to the other leading pathway. Further, it is understood that the flow streamline S2 for a particle of fluid emanating from the rotating element may be skewed at an angle relative to normal vector V. This skewing can be created from the asymmetry of the flow inducing shapes, especially if there is greater flow approaching the maximum diameter from one side of the pumping element as compared to the flow approaching the maximum diameter from the other side.

In addition, various embodiments of the present invention include means (60, 760, and X60 variants) for pumping that, even when deployed, permit sufficient flow within the junction to provide a reasonable time interval (hours) to percutaneously intervene should there be problems with rotating a pumping element. Further, as will be shown in FIGS. 18-22 and 41, in some embodiments the deployed pumping element is shaped such that fluid turbulence at the junction is decreased by the presence of the non-rotating means for pumping.

This device 720 applies to neonates, children and adults with functional single ventricle who are undergoing, or have previously undergone, univentricular Fontan palliation. Proposed duration of use is 2 weeks. For neonates, pilot data indicate that support may not be necessary more than 2 weeks. In some circumstances, longer duration support may be necessary (e.g. bridge to transplant). Support exceeding 2 weeks could include a pump change. This is supported by other clinical scenarios in which device change occurs bi-weekly: ECMO circuits, to mitigate thrombus risk; and central venous lines, to reduce risk of infection.

Surface modification will increase H-Q performance considerably. This is provided by an expandable impeller 70 which folds (stows) to a low profile. In addition to its structural role, the underlying impeller frame can serve as the substrate for the expression of impeller surface vanes. Vanes X62.3 are adapted and configured to avoid cavitation, minimize flow separation and turbulence, in addition to providing structural integrity. Transitions at the shaft and outflow edge will gradually contact fluid to minimize tip and hub vortices.

In those embodiments in which rotor 760 can be internally pressurized, the resulting surface shape of rotor 760 is determined by a combination of membrane stiffness, the as-molded membrane shape, the geometry of the deployed wires 774 or filaments 763.4, centrifugal forces, and the pressure differential across membrane 761. The pressure differential is established by the difference between the pressure internal to membrane 761 and the pressure to the membrane (which ranges from systolic pressure to diastolic). By establishing a predetermined pressure differential, the shape of the troughs inbetween vanes (or simply the shape of the impeller, for those applications not having internal vanes) can be changed to provide the particular results.

In one embodiment, the pressurization system is gaseous. Since gas is compressible, the shape of the rotor can vary as the pressure differential changes. Higher circulatory pressure causes the troughs between vanes to deepen. As circulatory pressure decreases, the membrane surface expands outwardly more, such that the troughs are less deep and distinct. Thus the shape of the pumping surface can change in rhythm with the heart. In yet other embodiments, the stiffness of the membrane is higher than in other embodiments, such that the pressure differential across the membrane provides less variation in shape. In either of the two aforementioned embodiments, it is possible to adjust the internal pressure to achieve a shape (which may be a time-averaged shape or a substantially invariant shape) that provides optimum pumping characteristics. For example, in some embodiments it may desirable to expand the shape of the impelling surface such that there are few surface indications of a vane. In such a state the pumping characteristics would be dominated by von Karman viscous flow. However, the internal pressure could also be reduced to achieve a more distinct shape of the vane (such as shown in FIGS. 32 and 33), in which case the flow exiting the pump would be more strongly influenced by centrifugal forces. In various embodiments, such modifications to the rotor surface can result in improved hydraulic efficiency, altered flow characteristics, or reduced risk of cavitation.

With induced fluid rotation, the path of least resistance may be obtained by modifying the impeller surface vanes to optimize vortical flow. This creates homogenous flow based on a coherent vortex structure which aids the inertial stability of the resultant fluid field. As such, in those embodiments in which the surface of the pumping element includes vanes, the flow is produced not by the actual impeller per se, but rather by fluid rotation induced by the impeller. Once rotation is established, friction and energy losses are minimized because the impeller serves to support and sustain rotation of the inflow field, rather than drive flow itself. The rotational field organizes and self-propagates across the (2-sided) conical impeller; if rotation stops, fluid follow continues as angular momentum fades.

The cage 740 centers the rotating impeller 760 and prevents rotor contact with the vessel wall. One preferred aspect of cage 740 is resistance to external deformation. Preferably, cage 740 when deployed has a bulging shape that is larger than the bulging shape of rotor 760, such that there is sufficient clearance between the rotor and the cage to avoid contact there between. Cage 740 preferably has sufficient strength to not be deformed by contact with the walls of the circulatory pathways, especially in those situations in which the cage and rotor are not centered in the junction. Yet other aspects of some embodiments of cage 740 are: 1) safe and reliable opening and closure; 2) avoidance of thrombus; and 3) least possible disruption of flow and hydraulic performance. The cage in some embodiments of the present invention does not play an active role in flow modification, but it may be modified to minimize turbulence where incoming axial flow crosses through the cage hub, as dictated by CFD and flow studies. As one example, in some embodiments of the present invention the filaments of cage 740 that establish the bulging shape can include a degree of twist, such that any blood flowing over the filament shape is redirected at least in part by the twisted shape. In such embodiments the twisted shape can be useful in inducing or removing swirl from the blood entering or exiting the rotating impeller. This swirl can be expressed as being helical in shape relative to the central axis of the rotor 760 (similar to that as shown in FIG. 33). Further, the shape of the filaments may assume an axially twisted shape. Such helical or swirled shapes can be induced in some embodiments as the remembered shape of a tube fabricated from memory metal. Combined interaction of the impeller and cage will minimize residence time, recirculation, and disruption to flow. The transition from stationary to rotational shaft and where cage filaments arise from the hub have flow patterns that preferably minimize risk of clot.

In some embodiments, cage 740 is fabricated from tubing that has a region in which a plurality of lengthwise slots have been cut and material removed from the wall of the tubing. This region of the tube has a plurality of slots imposed on the wall of the tube, with each pair of slots defining a filament there between. When an axial compressive load is applied to the tube, the region of filaments and slots, being weakened, buckles and bulges outward to a first shape (as best seen in view B of FIG. 17.)

The impeller frame in some embodiments includes a plurality of vanes 762.3, the frame preferably being constructed from a base of tubing, using either metal (stainless steel, memory-shape alloy Nitinol®) or plastic. For metal, the tube has a longitudinally cut central region to form filaments which are approximately half the length those of the outer (cage) tube and which have curvature and thickness/width properties to yield a predetermined unfolded/open/deformed geometry. The filaments 762.3 are preferably flat and concentric when closed, and form a bi-conical disk upon axial compression. Filament length of the inner tube relative to filaments of the outer tube (stationary cage) can determines tip:cage clearance gap and is thus modifiable. Alternatively, yet other embodiments contemplate a plastic-based impeller frame (mandrel groove technique or injection molding), which is covered by a pliable or elastic membrane. Shape and surface variation may include folding or imbrications to provide redundant material for expansion, and also provide shape memory for folding back to an orderly and defined collapsed position. Modification of frame filaments (thickness, width, curve, etc) along their length can determine morphology of the deployed shape. Spars may have thickened or otherwise modified edges to determine surface vane fluid flow properties. The blood contacting membrane elastomer 762 may be permanently bonded to the underlying frame to enhance structural integrity, or it may drape over the underlying frame.

The impeller 760 is preferably covered with a thin, seamless, impermeable membrane with high elastic modulus (expandable in one embodiment from about 3 mm of diameter to 18 mm) to form a minimally thrombogenic, biocompatible, blood contacting surface. Materials capable of this mechanical performance range include silicone polyether urethanes which are known to be biostable and reasonably biocompatibile with acceptable ultimate elongation, acceptable tensile strength, acceptable flex life, and acceptable recovery. The impeller frame imparts directional surface vane properties to the membrane surface to optimize impeller streamlining and hydraulic function, in those embodiments in which the deployed shape of the impeller includes vanes, and yet other embodiments, the bulged outward shape of the impeller is relatively smooth, and such impellers induce mixed flow (i.e., both axial and centrifugal) by viscous drag between the blood and the surface of the impeller.

The volume within the impeller varies with opening and closing. In some embodiments, this can be either a positive or negative pressure space, which may impact the impeller surface. In some embodiments, negative pressure is used to maintain a conical impeller shape, and a scalloped contour of the membrane between frame struts. Pressure status may facilitate opening and/or closing; for example, positive pressure will assist opening, negative pressure will assist closing. Fluid access from the purge system is possible through fenestration(s) in the central impeller shaft. In various embodiments, the central space is fluid filled or a vacuum, and in yet other embodiments the central space is at positive or negative pressure. In yet other embodiments, the surface shape is further modified by centrifugal forces on the membrane.

The expandable impeller is mounted on a central shaft 734.2, which provides one or more of the following in various embodiments: 1) axial support for impeller and cage; 2) a sliding interface for impeller opening and closing; 3) detents to limit deployment and prevent overexpansion; 4) a passageway for purge fluid to distal bearing/seal; 5) fenestration for fluid filling of the central impeller space, if indicated by design; 6) a sliding interface for the axial rotating component which may impose spirality to the impeller when opened (for surface flow enhancement) or when closed (for orderly folding).

The cage is constructed from a larger diameter concentric metal (examples include stainless steel, Nitinol®) tubing with approximately 4-10 radially distributed longitudinally straight parallel filaments circumferentially separated by slots. The filaments expand to a bulged shape which upon axial compression to form a symmetric or asymmetric elliptical cage. Cage filaments are approximately twice the length of the impeller splines. The beam (tube curvature) in the splines naturally forms an atraumatic surface in the event of contact with the vessel wall. It is preferable, but not necessary, that the cage has no hinges, pins, recesses, cavities, or points of sharp angulation. Device closure and removal can be assured similar to vena caval filter extraction systems in which an end hook is incorporated for snaring and extraction using a snare and sheath.

Some embodiments of the present invention include differential filament stiffness to favor softness/deformability at maximal diameter regions, yet provide stiffness/non-deformability closer to the hub, where structure establishes to the spatial relationship between impeller and cage. Additional examples of filaments and slots adapted and configured for variable axial stiffness are shown and discussed relative to FIGS. 34 and 35. Yet other embodiments include bridging struts to link longitudinal struts (similar to vena caval filters and stents) to limit gaps for tissue breach of the cage, particularly at inflow ends. Maximal cage diameter is preferably 95% vena caval diameter.

An external linkage controls opening and closing of the pump by axial compression. Closure is accomplished when the linkage is released by the tensile properties of each frame and the elastic impeller covering. The load to deflect the outer cages can be counter-balanced using a coil microspring.

Figure 18:
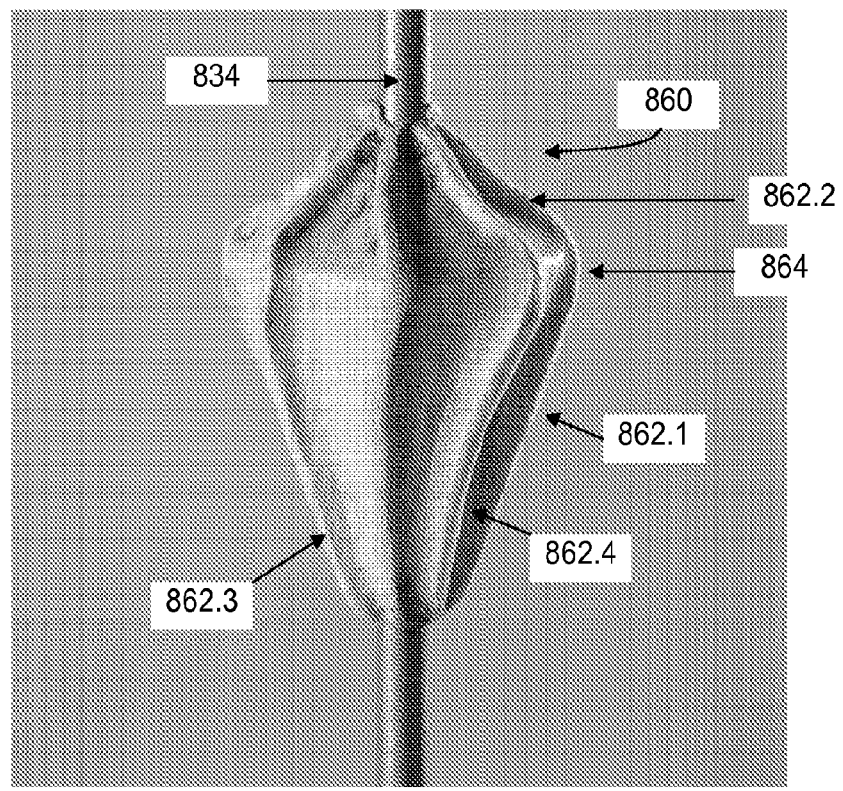
FIG. 18 is a side elevational photographic representation of an apparatus according to another embodiment of the present invention.
Figure 19:
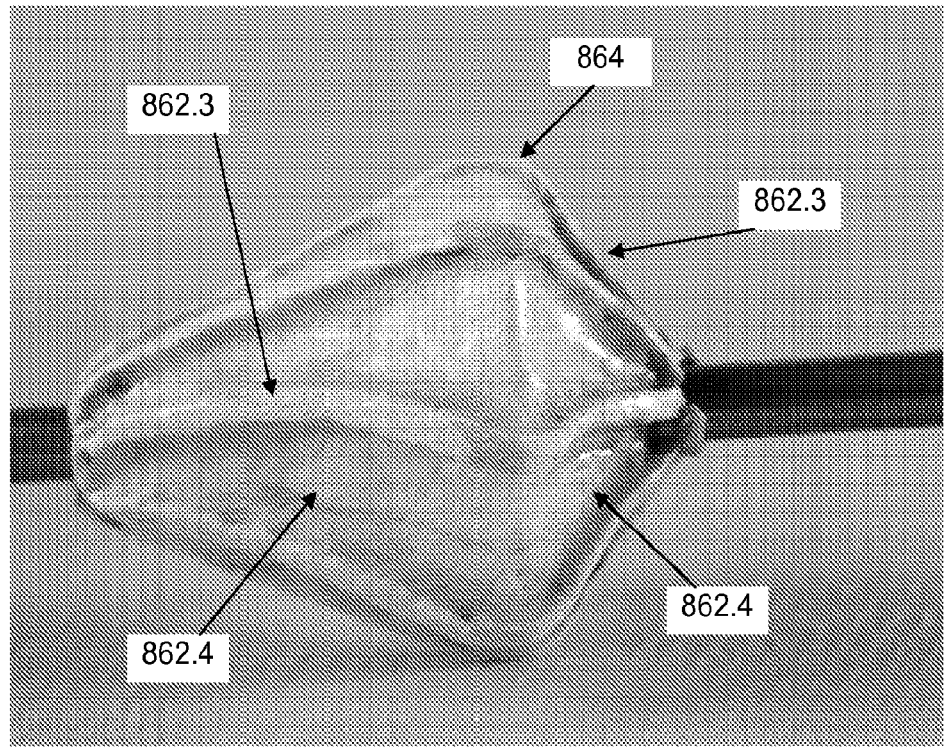
FIG. 19 is a photographic representation of the apparatus of FIG. 25.

FIGS. 18 and 19 pertain to a static flow stabilizer 860 that includes some mechanical concepts from the viscous impeller pumps discussed above. A viscous impeller pump (VIP) concept can be applied as a stationary device or static flow stabilizer 860 in the TCPC to stabilize flow patterns and reduce kinetic energy loss which occurs due to otherwise turbulent and colliding flows. In one embodiment, a flow stabilizer 860 can be inserted percutaneously into the intersection of fluid flowpaths and expanded into a flow stabilizing shape after placement. In some embodiments, the flow stabilizing shape is placed within a cage 840. In some embodiments, the cage is adapted and configured to contact the walls of the circulatory system at the junction. Further, the cage can include internal supports for positioning the flow stabilizing shape within the junction relative to the cage. An expandable central stabilizer based on the VIP concept can offer some or all of the following aspects:

Reduction in kinetic energy losses from colliding inflow paths in the TCPC

The device can be freely suspended in the TCPC, and not incorporated into the vessel walls, thereby reducing thrombogenicity risk and concern for growth potential;

An expandable and collapsible design permits placement and retrieval using percutaneous technique (similar to placement and retrieval of vena caval thromboembolism filters);

Once the stabilizer is removed, the flow pathways remain unobstructed;

The endothelial lining of the vessel walls is maximally exposed, as opposed to a device fixed or incorporated into the existing vessel wall, reducing thrombogenicity risk and tissue injury.

Potential clinical uses includes: (1) a static flow stabilizer could be noninvasively placed in patients with borderline Fontan function who need improvement in cavopulmonary blood flow; and (2) a static flow stabilizer could be used to improve hemodynamic status in patients who are listed for heart transplantation and may have a long wait for a donor cross match.

Referring to FIGS. 18 and 19, a static flow stabilizer 860 is shown having a generally conical flow inlet portion 862.1 that joins a downstream portion 862.2 at a rounded apex 864. In one embodiment, stabilizer 860 is asymmetric about a plane cutting through apex 864, with the inlet side 862.1 having a fairly gentle slope so as to gradually change the direction to flow (this direction being from bottom to top as viewed in FIG. 22, or from left to right as viewed in FIG. 23). The downstream portion 862.2 is conical at a steeper angle, this portion of stabilizer 860 serving to reduce the formation of eddy currents and recirculation of the flow as it comes off of apex 864. However, although flow stabilizer 860 is asymmetric about apex 864, other embodiments of the present invention contemplate symmetric stabilizer configurations. Further, it is noted that stabilizer 860 is axisymmetric about a central axis coincident with central rod 834. However, other embodiments of present invention are not so constrained, and can include flow stabilizers with little or no symmetry.

Flow stabilizer 860 includes a plurality of raised vanes 862.3, with corresponding adjacent troughs 862.4, arranged circumferentially about a central axis. As best seen in FIG. 23, the vanes 862.3 are turned in a consistent angular manner so as to impart swirl to fluid flowing over impeller 860. Further, this alternating arrangement of vanes and troughs can be seen to pass over apex 864 and continue onto downstream side 862.2. However, yet other embodiments of the present invention include an arrangement of vanes that are straight relative to the central axis, impellers that have vanes only on the upstream side of the device, and further includes impellers that have no vanes at all.

Figure 20:
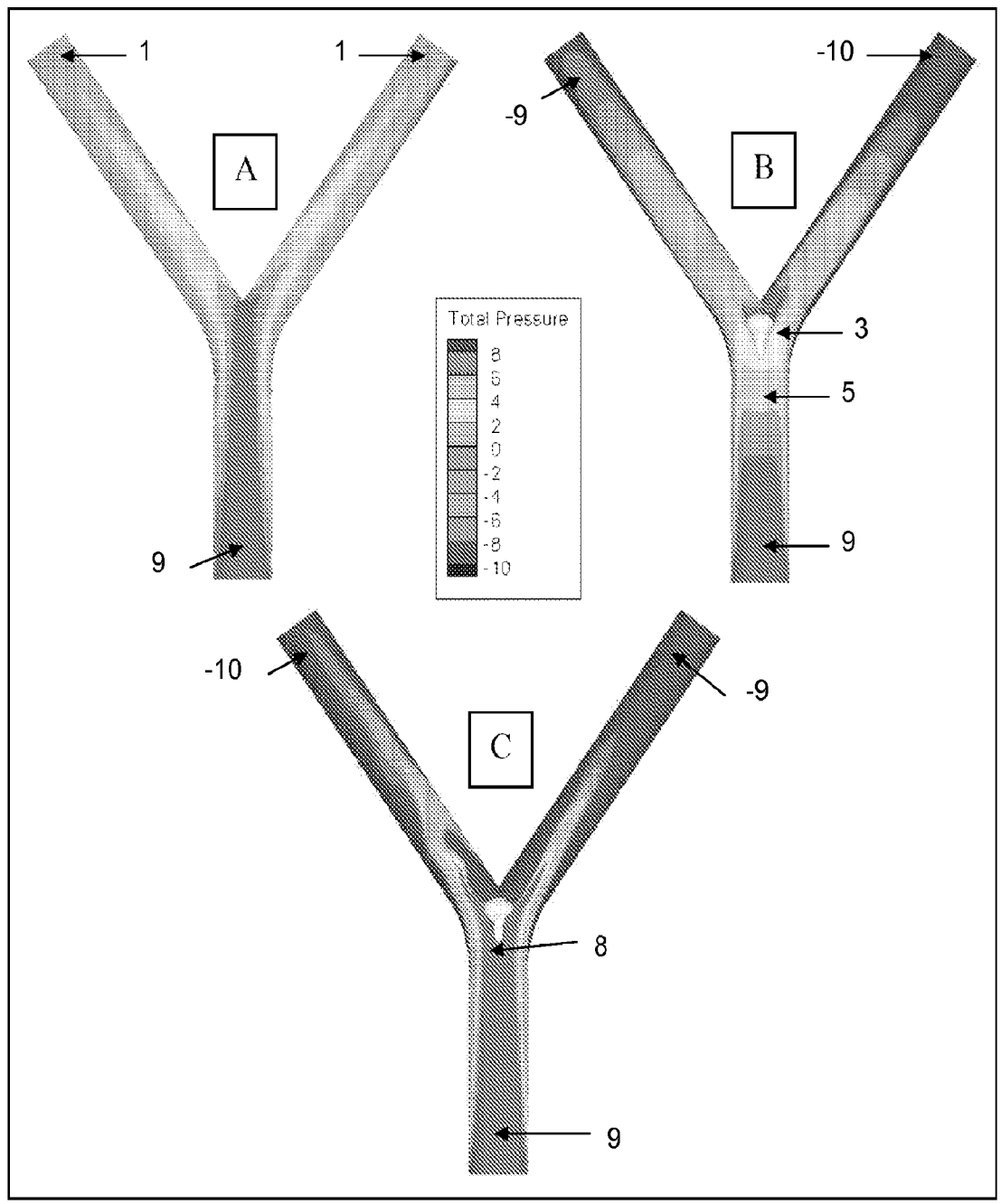
FIGS. 20, 21 and 22 show predicted flow field characteristics of one device according to one embodiment of the present invention [B] used as a static flow device; and according to another embodiment of the present invention [C] as a rotating impeller.
Figure 21:
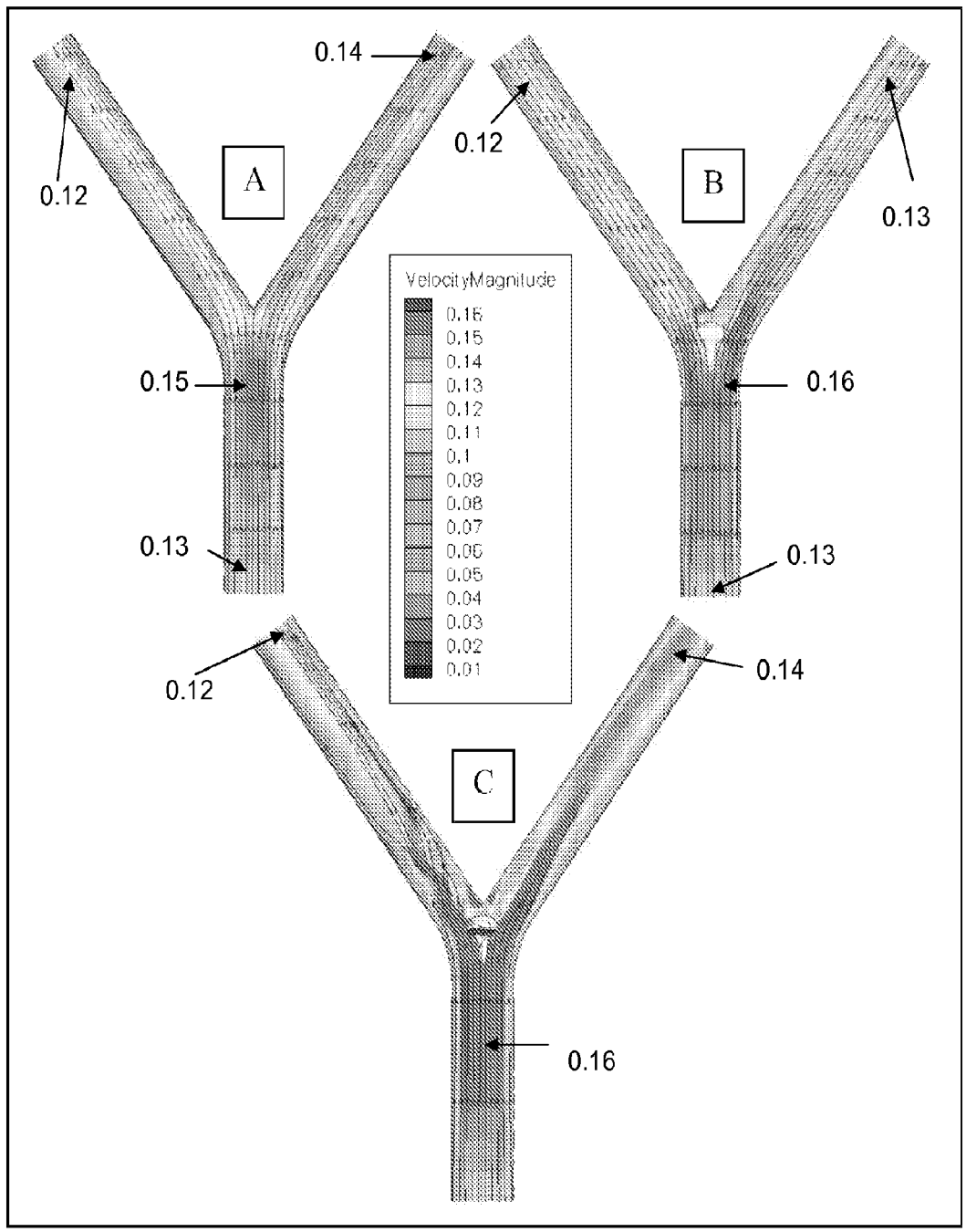
Figure 22:
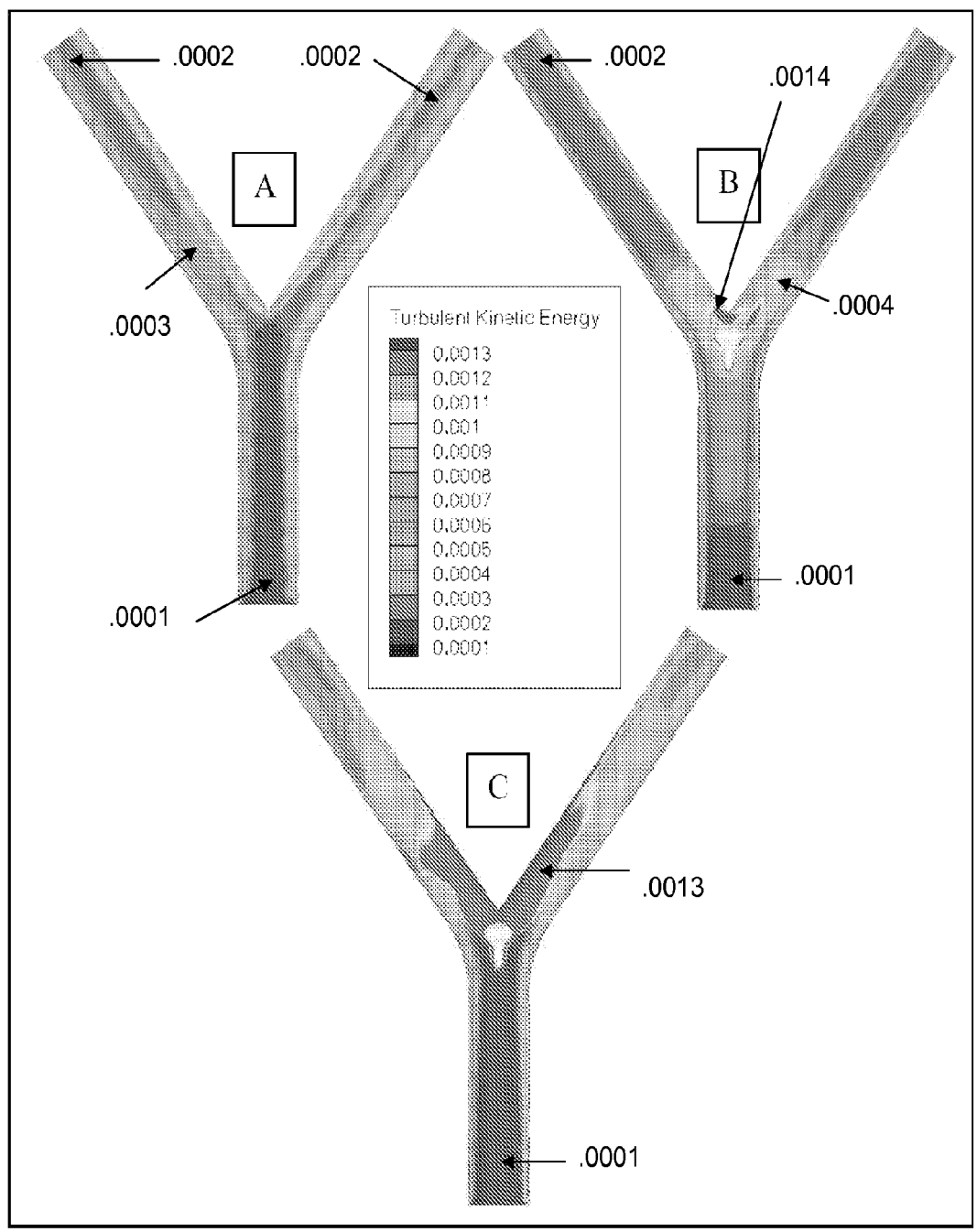

FIGS. 20, 21, and 22 present flowfield predictions for a bifurcated flowpath in three states: (A) a single, open passage bifurcating into two open passages; (B) the configuration of flowpath (A) with a static flow stabilizer 860 placed at the vertex of the flowpath; and (C) the flowpath of (A) with a rotating viscous impeller 860 at the vertex.

Using idealized split geometry a model of the pulmonary bifurcation between the main pulmonary artery (MPA) stemming from the heart to the subsequent left and right pulmonary arteries (LPA & RPA) was created. The model was idealized in effect to create a harder condition for which the pump to act. Physiologic geometry would have a broader angle at the Y which is more analogous to a T. Since the design of the pump is tailored to pumping fluid from the axial direction to the radial direction, as needed by the junction geometry, the model challenges the pump with a flow condition suited for an axial flow pump.

The analysis shows that even in the depicted geometry there is possibility to augment the flow field. To illustrate this, the model was used in three cases. The first serves as a baseline from which the pump's performance may be analyzed. This baseline simulates a passive and physiologic flow rate of 5 L/min and a 45% to 55% split of the outflow between the left and right pulmonary arteries, respectively.

The pump was modeled as a generic asymmetric smooth impeller sitting within the transition from the MPA to the LPA and RPA. The pump 860 was tested in two nominal cases. The first case shows the affect of a stationary, non-rotating pump on the surrounding flow field and the second shows the affect of rotation of a pump 860 at 5,000 rpm. The stationary case also demonstrates the small extent of obstruction to flow during pump placement and/or premature failure of the device.

The total pressure, velocity magnitude, and turbulent kinetic energy of each of the three cases is illustrated in FIGS. 20, 21 and 22, respectively. The stationary pump acts as an obstruction to baseline flow contrastingly to the flow within the TCPC. This obstruction is on account of the fact that the Y geometry is already well suited for splitting the flow (evolution has a way of doing this), but the extent of the obstruction is still much smaller than other pumps (approximately 30% for the inventive pumps shown herein vs. 80% for pumps of known design).

As observed from the streamlines in FIG. 21, the rotating pump causes the fluid entering the LPA an RPA to rotate about each artery's central axis and generally improves the flow within the pulmonary bifurcation. This can be noted by the increased velocity magnitude throughout the flow field of the rotating pump case.

FIGS. 23-40 depict various aspects of pumping assemblies according to various embodiments of the present invention. As previously explained, any element numbers from the tens locations to the right (XX.X) proceeded by a number Y (as examples, 62.3 and 1262.3) are variants of one another, and are different to the extent shown and described, as would be understood by one of ordinary skill in the art.

FIGS. 23, 24, and 25 show various views of a cavopulmonary pump assembly 1020 in a deployed configuration. FIG. 26 shows the same device in a stowed position, as indicated by the prime (') suffix. Assembly 1020 includes a proximal end (on the right side of the figures) including a drive and displacing mechanism 1022. The distal end of assembly 1020 includes a protective cage assembly 1040 and a pumping assembly 1060 located within. A central span 1028 of variable length and including a catheter 1030 housing a flexible drive rod 1034.2 couples the proximal and distal ends of assembly 1020.

Figure 27A:
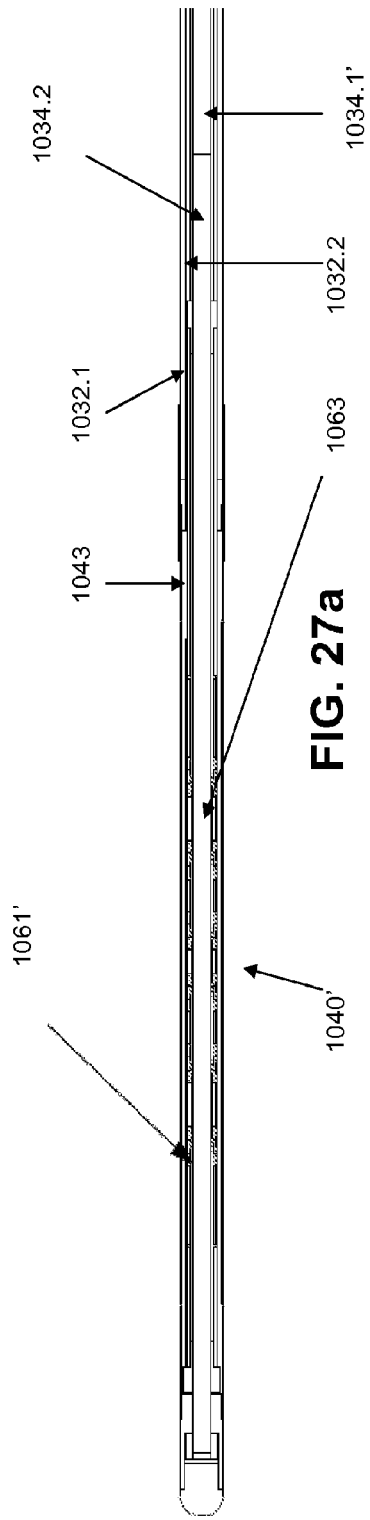
FIG. 27*a* is an enlargement of a portion of the apparatus of FIG. 26.
Figure 27B:
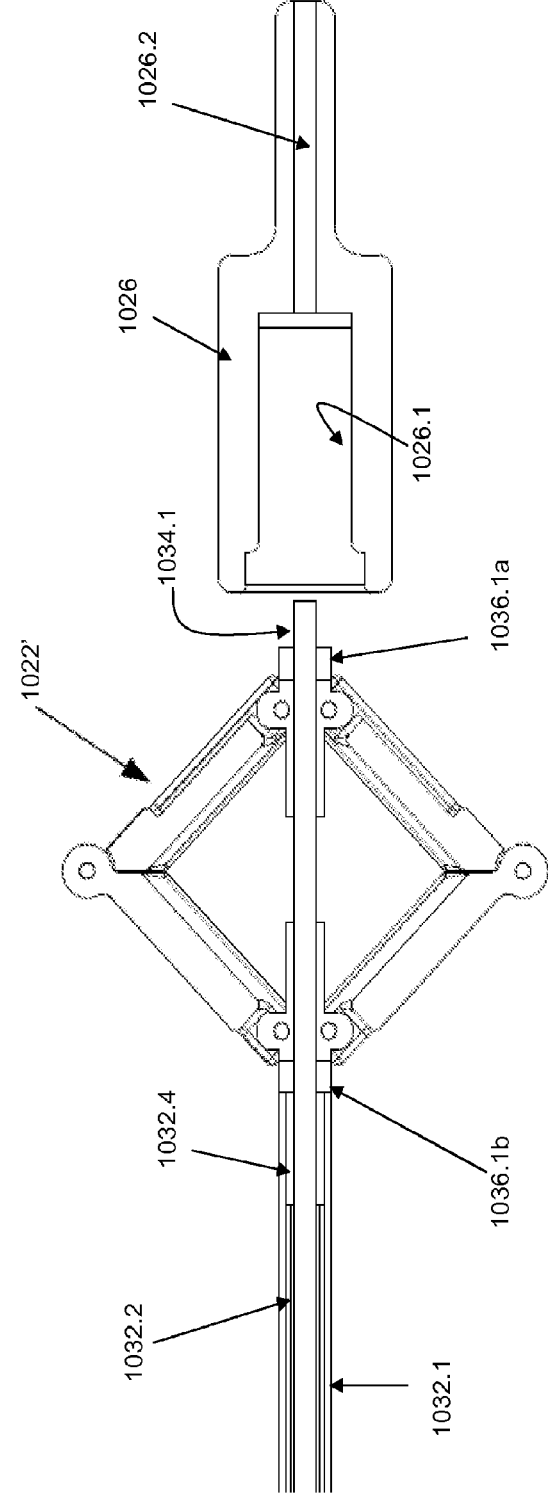
FIG. 27*b* is an enlargement of a portion of the apparatus of FIG. 26.

FIGS. 27*a* and 27*b* show enlarged views of the stowed apparatus 1020'. The proximal end of the apparatus includes a drive collar 1026 adapted and configured to both actuate and axial displacement mechanism 1022 (shown in the stowed position in FIG. 27*b*). In one embodiment, flexible central drive rod 1034.1 is pulled along a central axis of drive collar 1026, such that the end of rod 1034.1 is positioned within diameter 1026.2. In so doing, the diamond-shaped tensioners 1023 are forced into a linear arrangement, and in so doing, and as will be explained later, a predetermined displacement is imposed on the end of apparatus 1020. By rotation of collar 1026, tensioners 1023 are likewise rotated. Flexible drive shaft 1034.1 is originally coupled to the tensioners, and thereby imparts rotational motion into rigid central rod 1034.2, and thereby into a pumping element 1062.

Figure 28A:
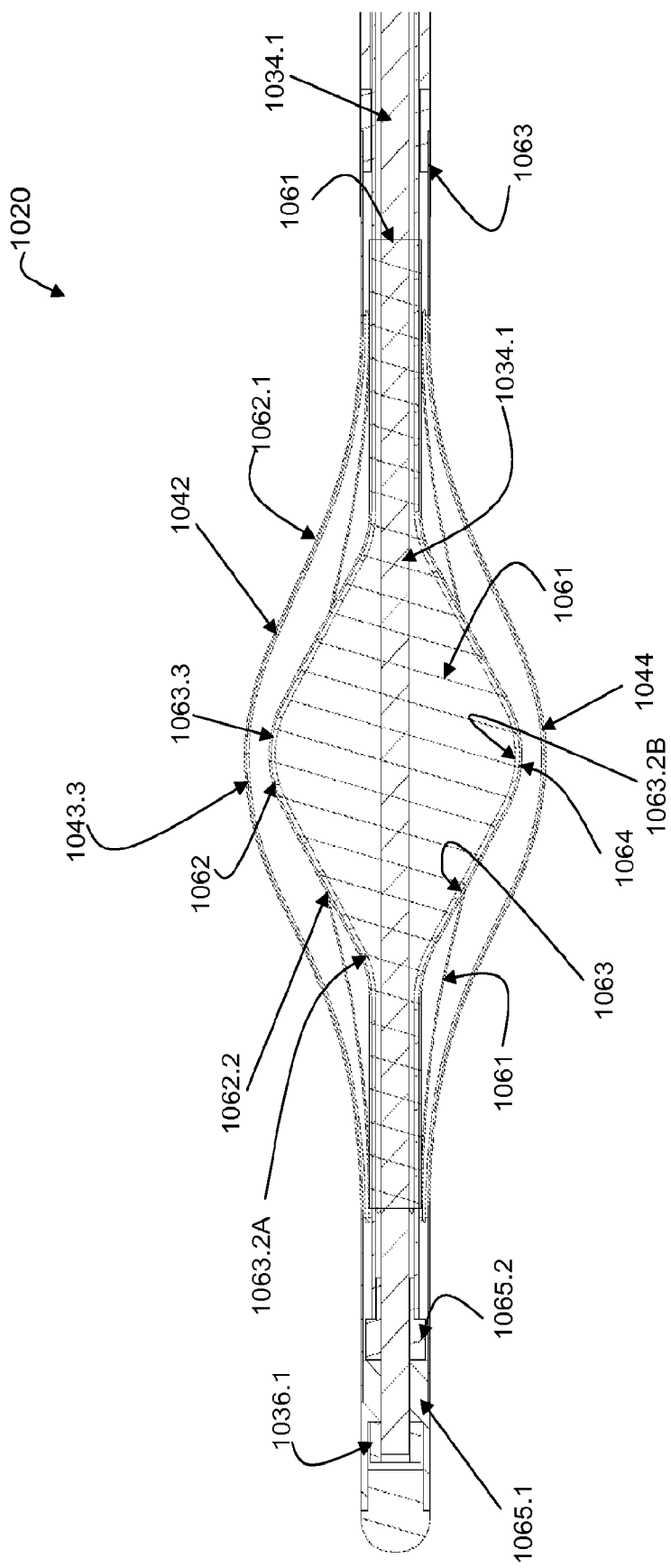
FIG. 28*a* is an enlargement of a portion of the apparatus of FIG. 24.
Figure 28B:
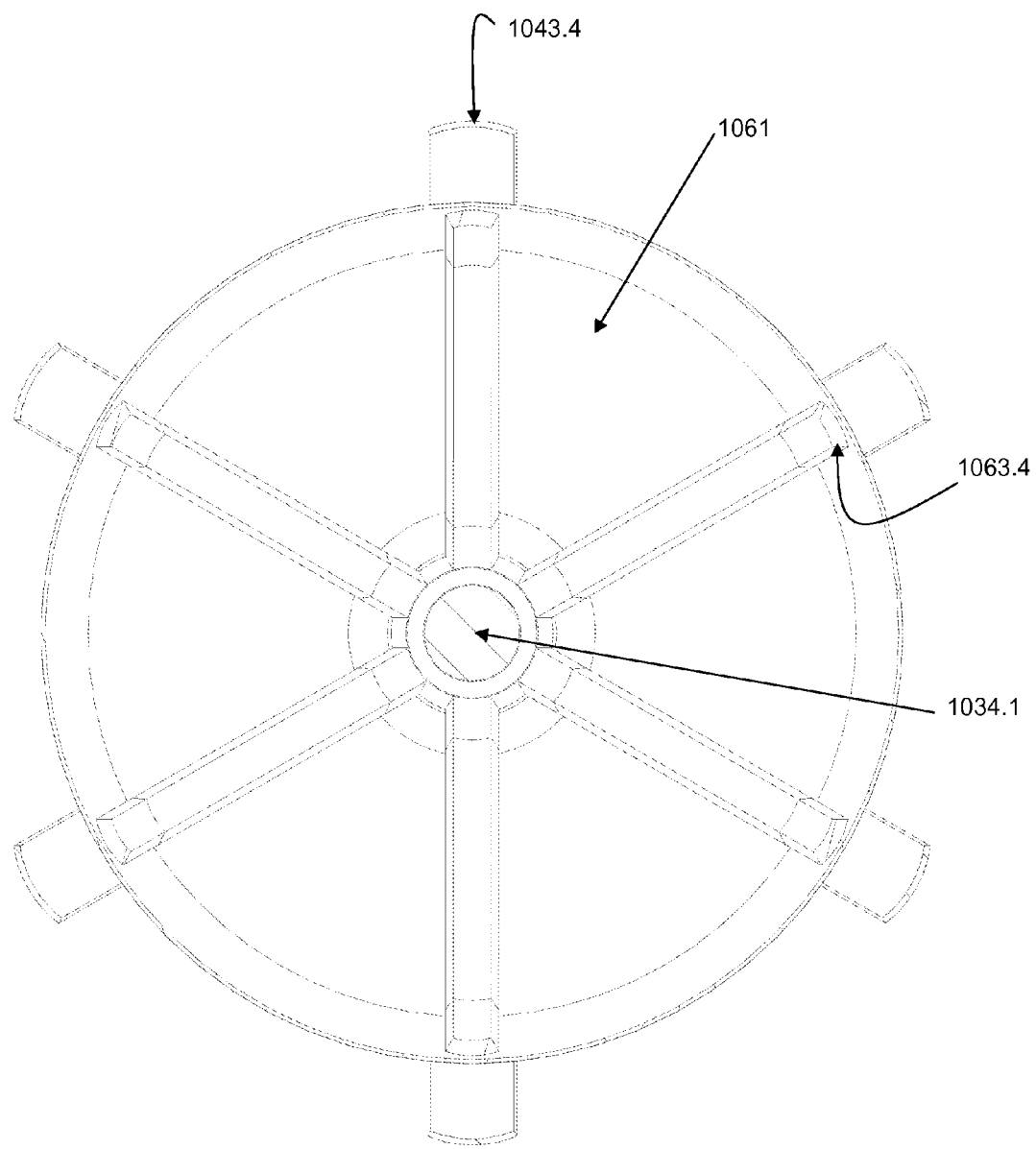
FIG. 28*b* is a cross sectional view of the apparatus of FIG. 28*a* as taken through the center of the midsection toward the left of FIG. 28*a*.

When this predetermined relative displacement (of an inner subassembly relative to an outer subassembly) a deployed configuration results as best seen in FIGS. 28*a* and 28*b*. FIG. 28*a* shows flexible drive rod extending to the distal tip of assembly 1020. The distal end of drive rod 1034.1 is bearingly supported in a radial direction by a front bearing 1065.1. On either side of bearing 1065.1, a thrust bearing 1036.1 and a second axially-locating bearing 1065.2 are coupled tightly to the outer diameter of rod 1034.1, thereby capturing rod 1034.1 within front bearing 1065.1.

Figure 29A:
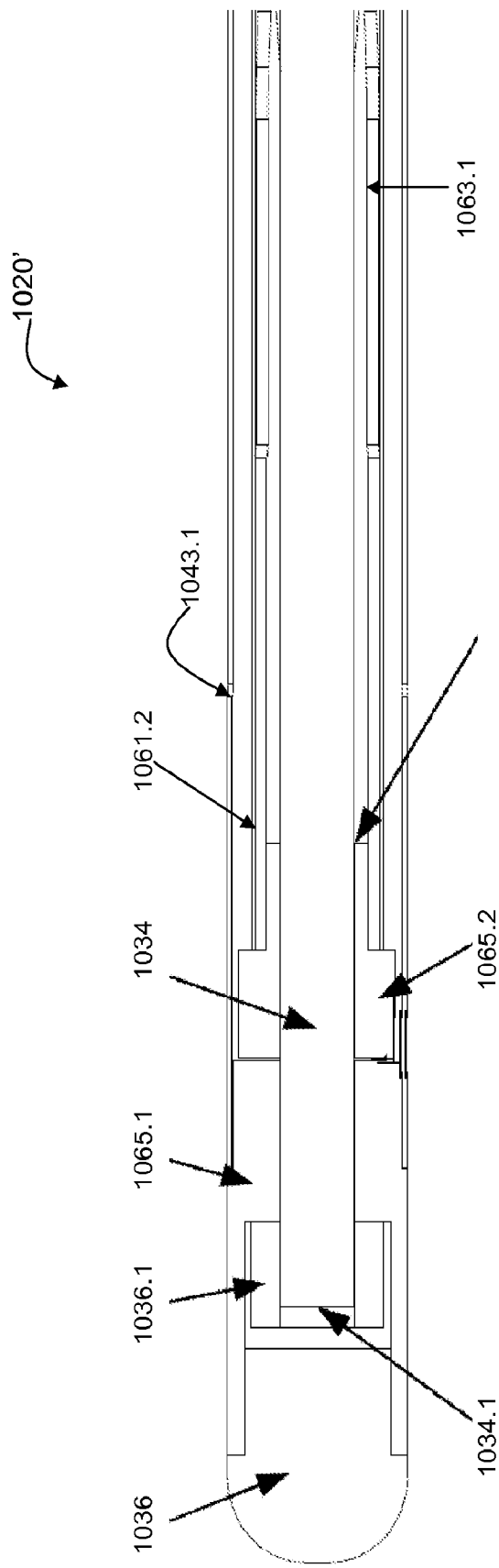
FIG. 29*a* is an enlargement of a portion of the apparatus of FIG. 27*a*.
Figure 29B:
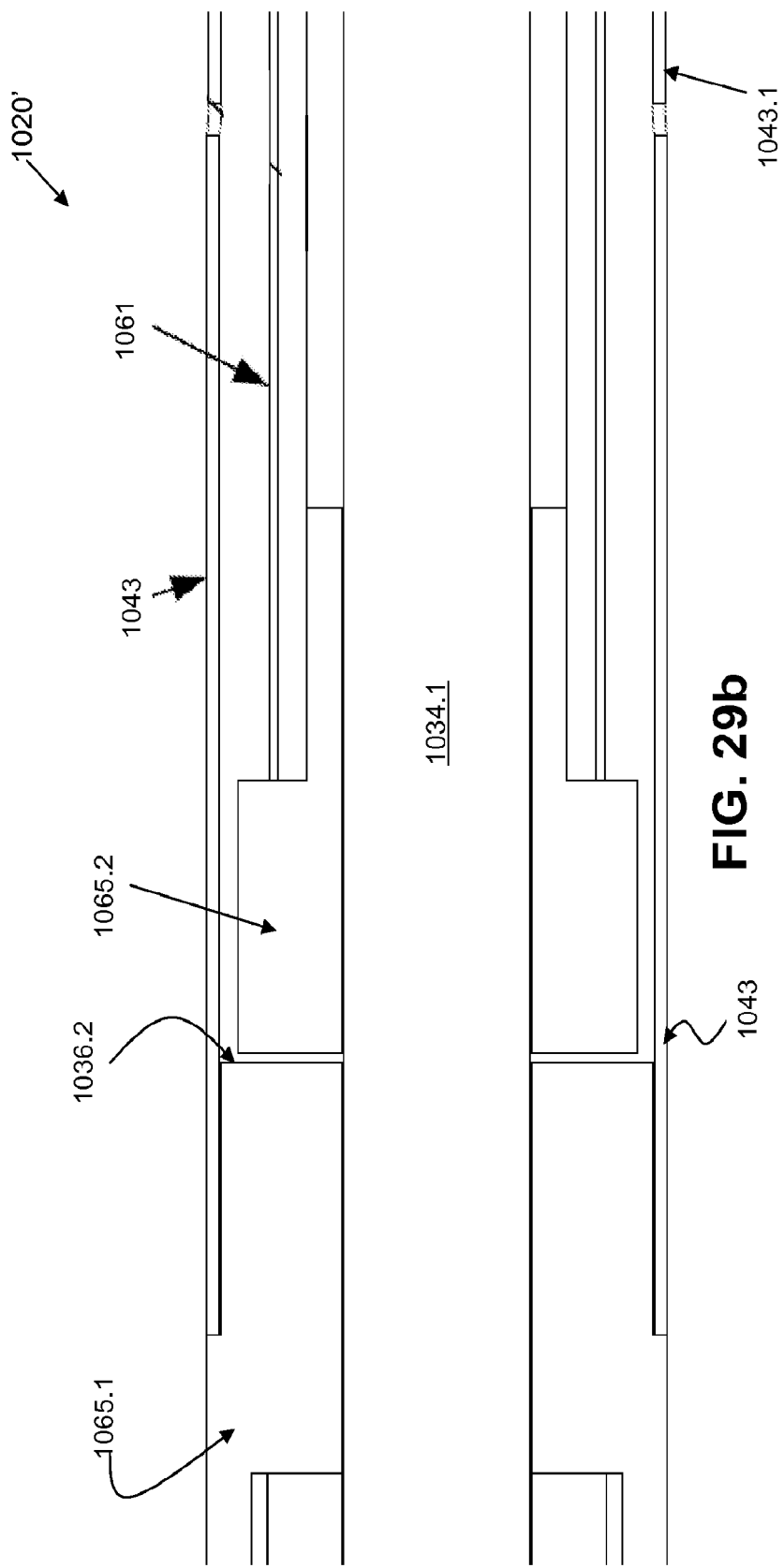
FIG. 29*b* is an enlargement of a portion of the apparatus of FIG. 29*a*.

A rounded nose 1036 is placed on the distal end of assembly 1020 to facilitate its entry and passage through the circulatory system. Referring to FIG. 29b, bearing 1062.2 is coupled at an axial location along the length of rigid rod 1034.1 such that in the stowed state there is an axial gap 1036.2 between opposing faces of bearings 1065.1 and bearing 1065.2. This gap represents a small amount of looseness that helps ensure that there is no residual compression in the stowed configuration, such that the cage 1040 and pump 1061 are able to return to their small diameters.

As the central drive rod rotates, rotating with it is an inner support tube 1063, and a pliable membrane 1061. Membrane 1061, providing a surface on the bulging shape of inner tube 1063, comprises a viscous impeller pump according to one embodiment of the present invention.

Figure 36A:
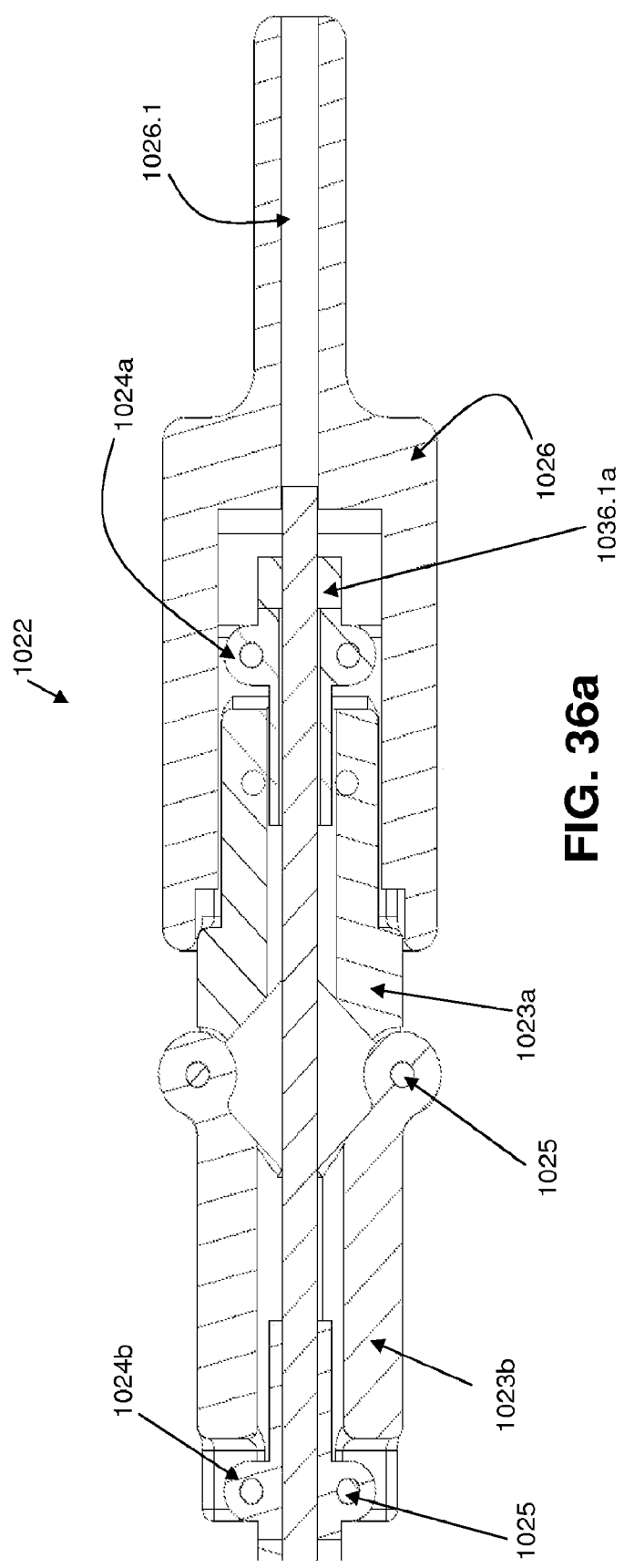
FIG. 36a is an enlargement of a portion of the apparatus of FIG. 24.
Figure 36B:
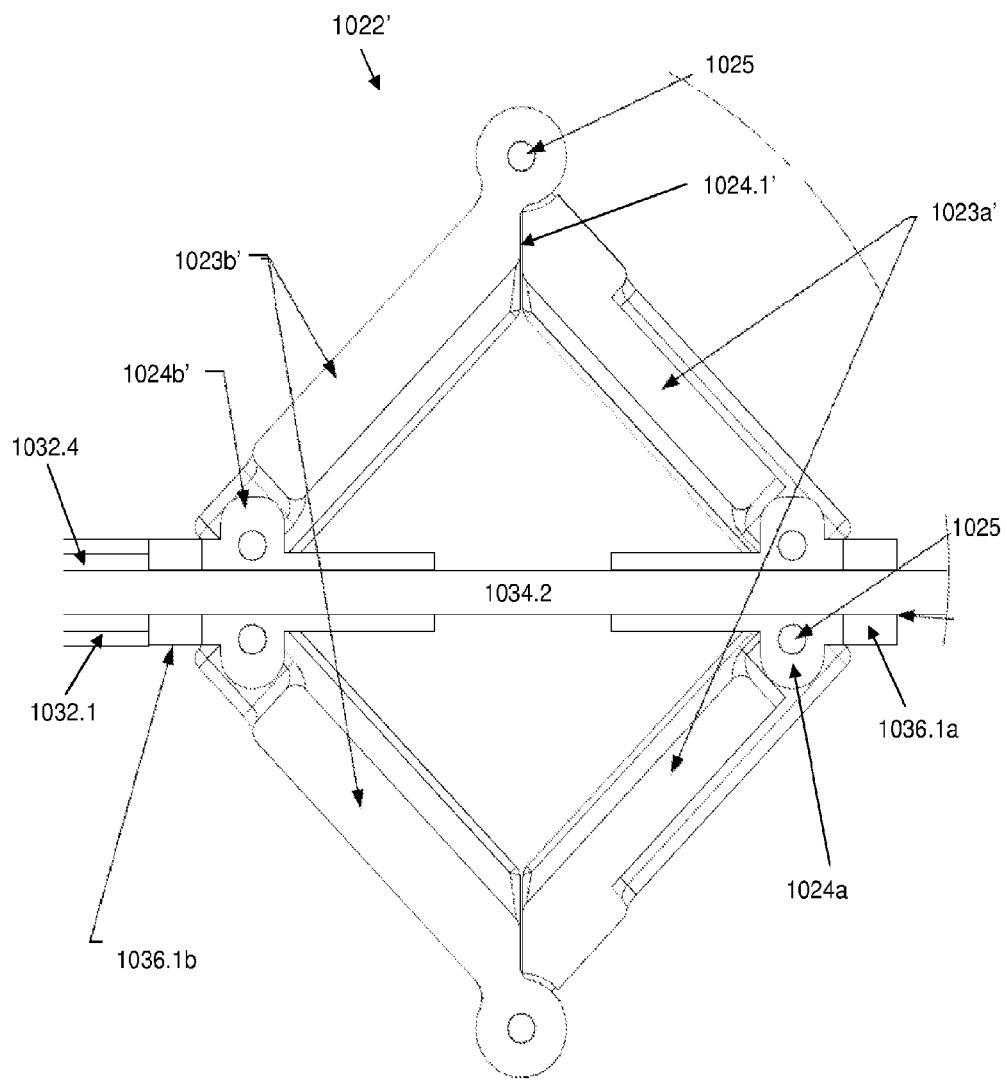
FIG. 36b is an enlargement of a portion of the apparatus of FIG. 26.
Figure 37:
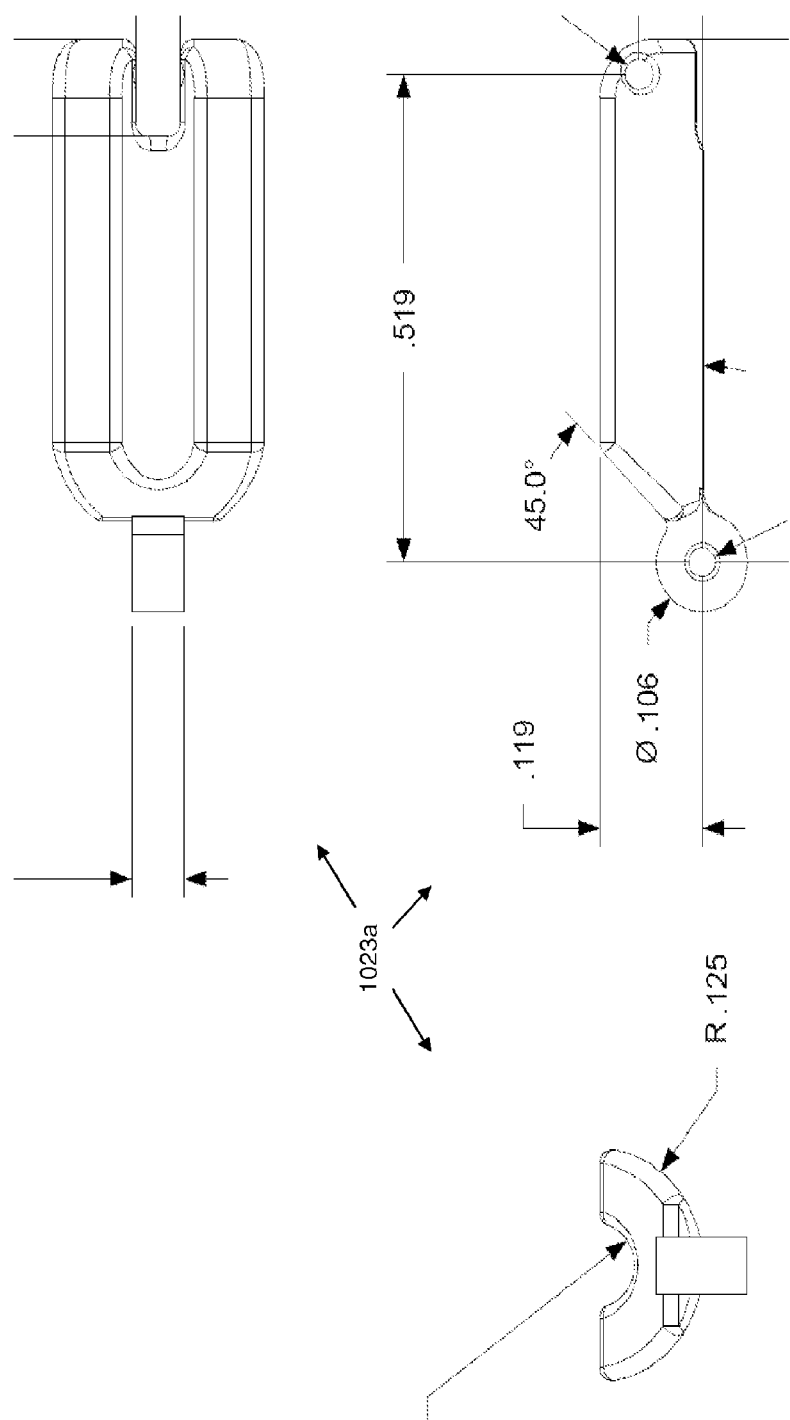
FIG. 37 shows three orthogonal views of a portion of the apparatus of FIGS. 36a and 36b.
Figure 38:
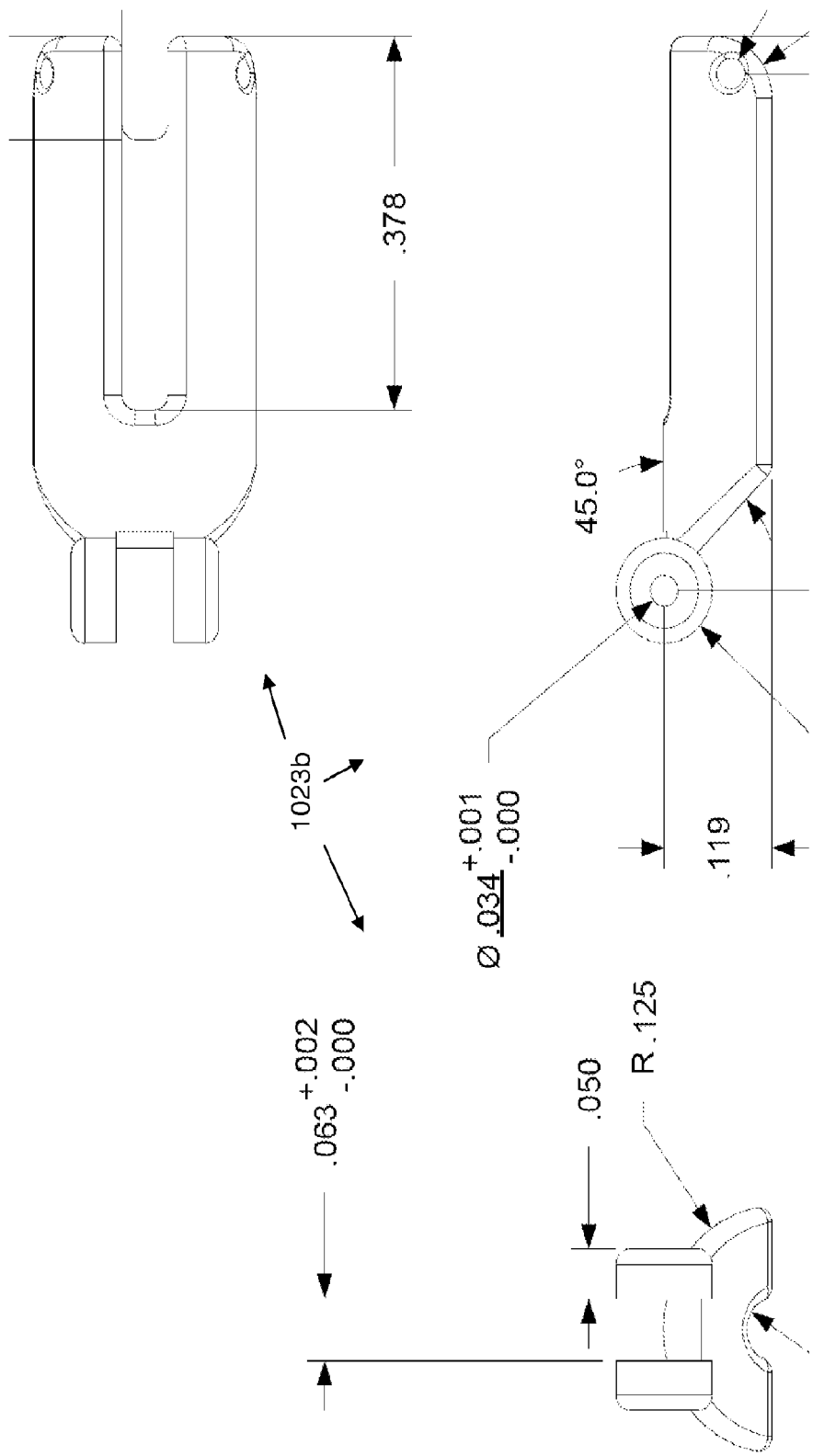
FIG. 38 shows three orthogonal views of a portion of the apparatus of FIGS. 36a and 36b.
Figure 39:
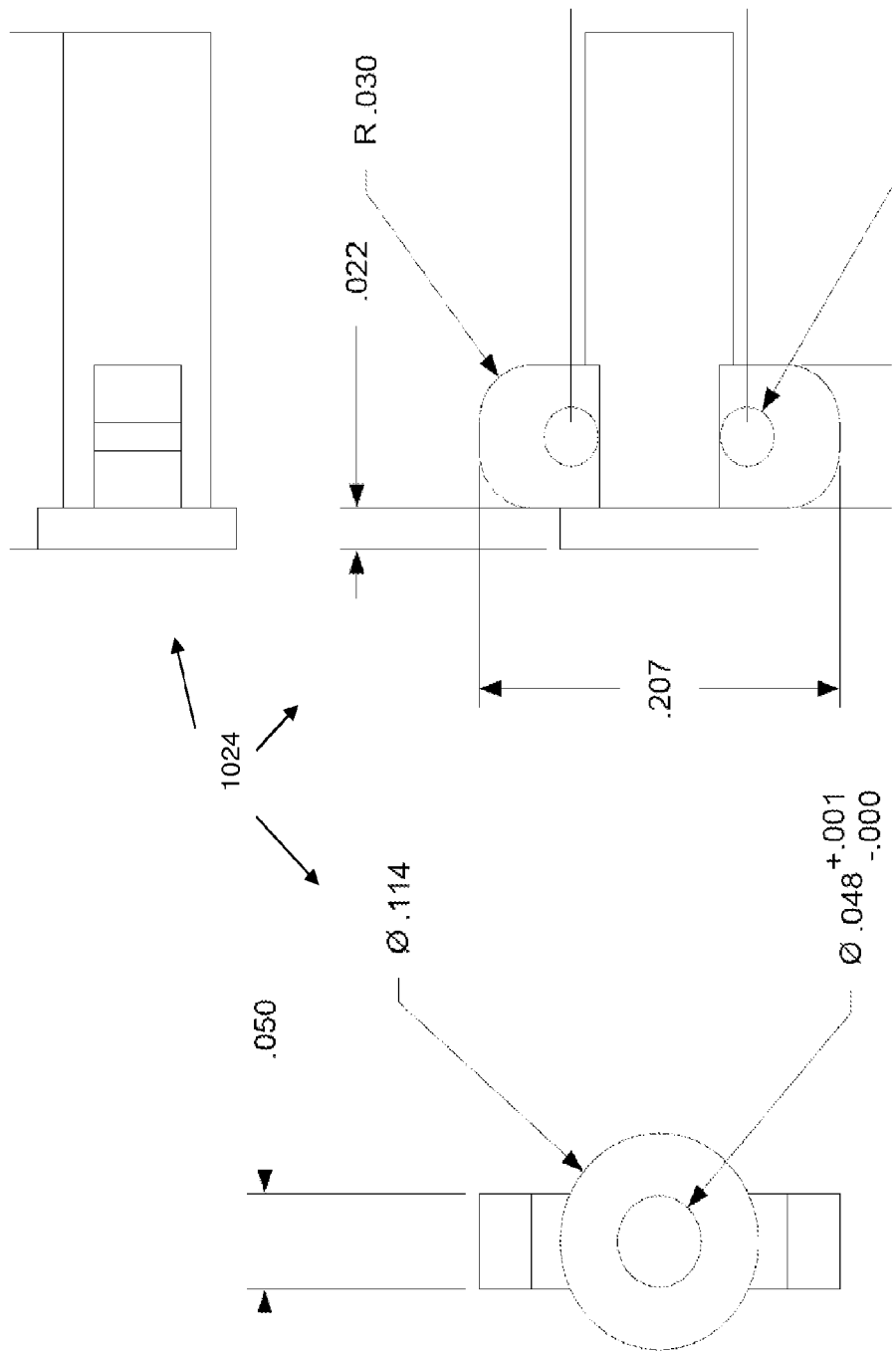
FIG. 39 shows three orthogonal views of a portion of the apparatus of FIGS. 36a and 36b.
Figure 40:
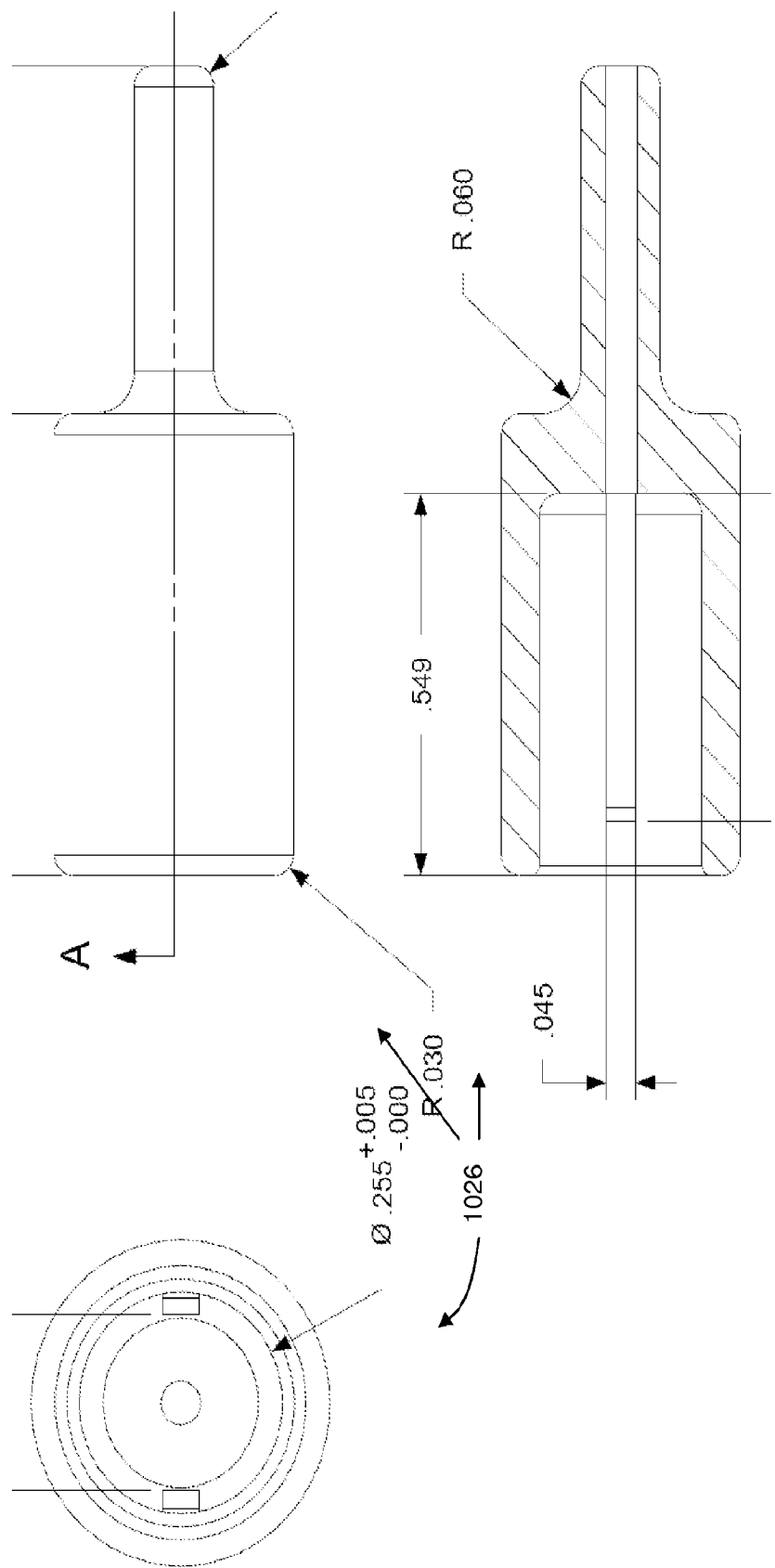
FIG. 40 shows two orthogonal views of a portion of the apparatus of FIG. 36a (along the top) and a cross sectional view of the apparatus (along the bottom).

Referring to FIGS. 27b and 36b, as tensioning arms 1023 move to the deployed (i.e. flat) configuration, collar 1036.1 pushes against two tubes that in turn each push on a different one of the outer tube and inner tube. As the tensioning devices collapse flat, their travel to the right (referring to FIGS. 27b and 36b) is limited by collar 1036.1a, which is affixed to rod 1034.2. In some embodiments, collar 1024a is further affixed to rod 1034.2, although the present invention contemplates those embodiments in which the rod is free to pass within collar 1024a, such that the tensioning devices 1023 do not rotate with the shaft.

Since the rightward movement of the collapsing tensioners is forced to the left (as viewed on the drawings), tensioner collar 1024b (through which the drive rod is free to slide) and collar 1036.1b (also through which the drive rod is free to slide) push against outer tubing 1032.1. This tubing applies an axial load to outer tube 1043, and results in the imposition of a bulging, buckled shape on that outer tube. Further, after traveling along drive rod by a free space 1032.4, the collar 1036.1b then abuts against the end of an inner tube 1032.2. This inner tube transmits compressive loading from collar 1036.1b to the inner tube 1063, likewise causing it to assume a bulging, buckled shape. Note that in the embodiments shown in FIGS. 27b and 36b, there is more axial displacement of outer tube 1032.1 (and therefore outer tube 1043) than there is of inner tube 1032.2 (and thereby of inner tube 1043), the difference being the axial empty space designated 1032.4.

Pump 1060 rotates within the cage assembly 1040, as best seen within FIG. 28. FIG. 28 shows assembly 1020 in the deployed position, an axial compressor force having been applied by displacement mechanism 1022 onto the assembly 1020. As the tensioners 1023 collapse to fit within drive collar 1026, the inner rotating assembly (including pump 1060 comprising membrane 1061 and inner tube 1063) is pulled and displaced axially relative to the static outer cage assembly 1040. This compressive load is applied between the opposing faces of collar 1036.1 and bearing 1065.1. The axial force causes both cage assembly 1040 and pump 1060 to locally buckle because of a plurality of predetermined, localized area of reduced stiffness in outer tube 1043 and inner tube 1063. Outer tube 1043 is adapted and configured to have a bulge at midsection 1043.3 that is of greater diameter than the bulge imposed at midsection 1063.3 of the inner tube. Preferably, membrane 1061 is sufficiently elastic to expand outward and generally assume a shape determined by its own elasticity and also the shape and spacing of the inner tube filaments 1063.4.

Figure 29C:
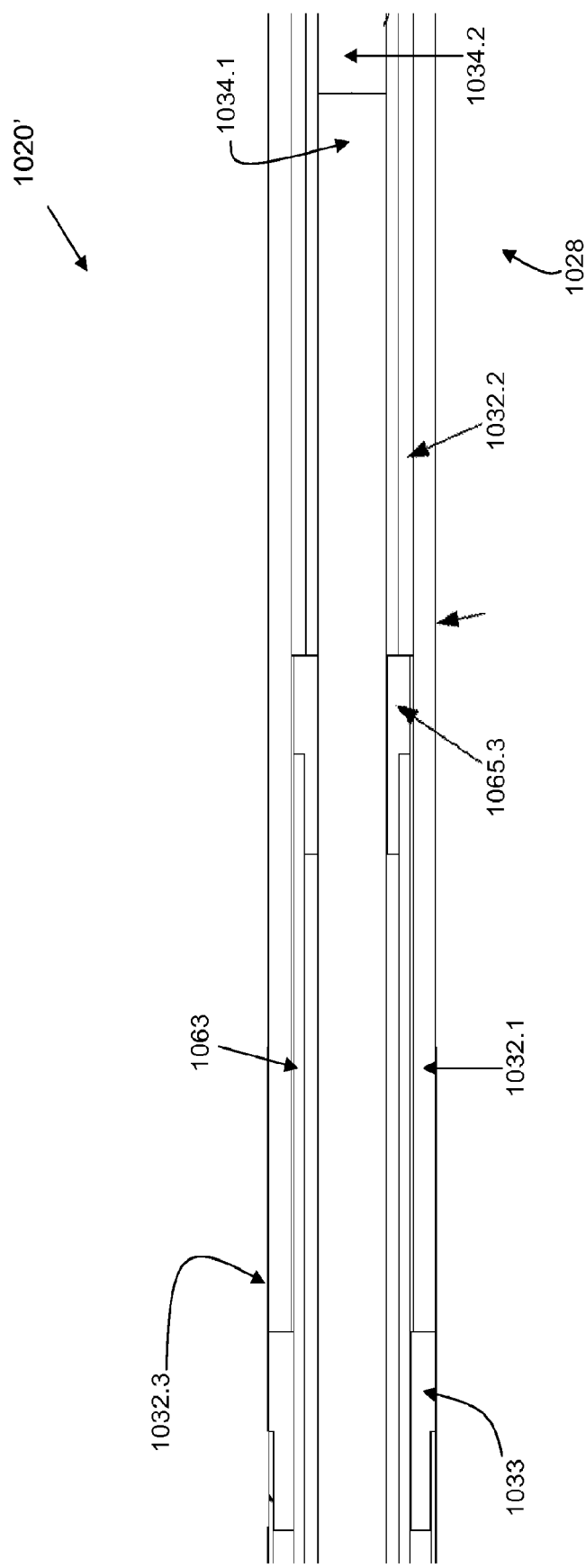
FIG. 29*c* is an enlargement of a portion of the apparatus of FIG. 27*a*.

Referring to FIG. 29c, the interface between rotating and non-rotating components within central span 1028 is shown. Flexible drive cable 1034.2 is shown coupled to rigid drive cable 1034.1 in a soldered butt joints, although various embodiments of the present invention contemplate any means of coupling the rigid and flexible drive rods. Rigid drive rod 1034.1 is radially supported by bearing 1065.3. Inner tube 1063 is coupled to a reduced diameter distal section of bearing 1065.3.

Figure 30:
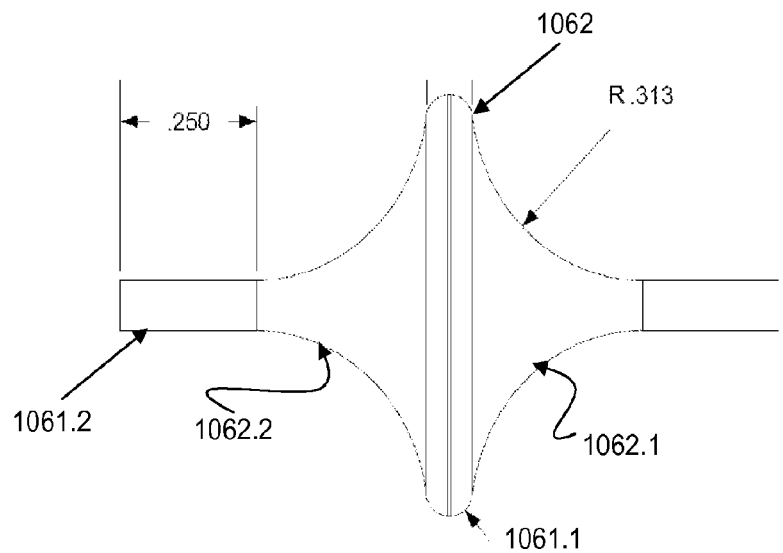
FIG. 30 is a side elevational view of a pumping membrane according to one embodiment of the present invention.
Figure 31:
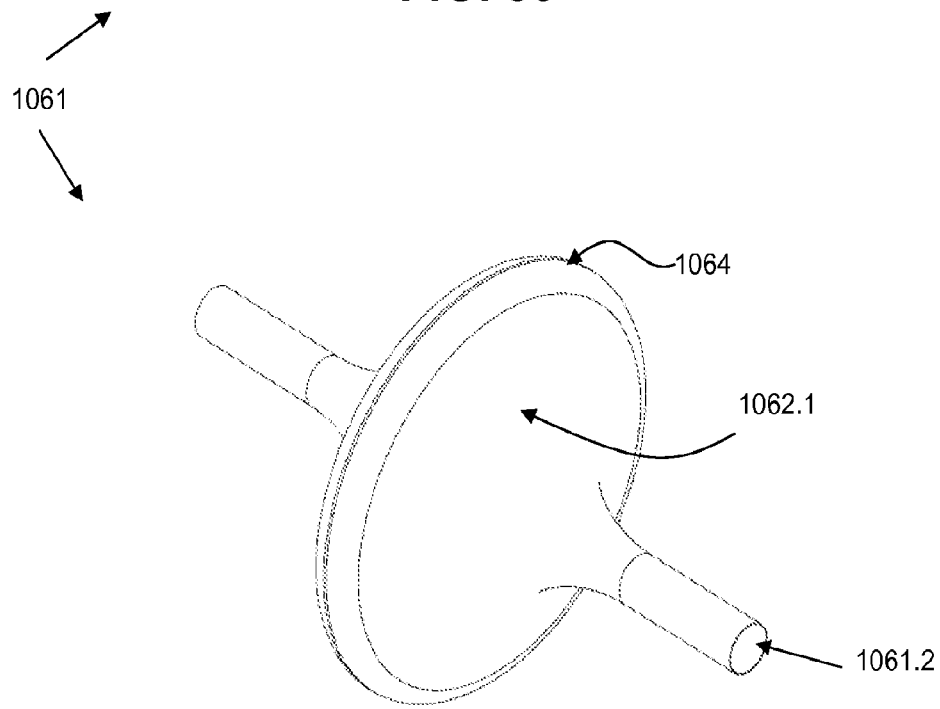

FIGS. 30 and 31 give views of pliable membrane 1061 in its molded configuration. Membrane 1061 includes in one embodiment an enlarged midsection 1061.3 that necks down in the distal and proximal directions to smaller, generally cylindrical hubs 1061.2. In one embodiment, substantially conical proximal and distal surfaces 1062.1 and 1062.2, respectively, transition from the large midsection to the hubs. Preferably, membrane 1061 is circumferentially continuous about a central axis, and thereby presents a continuous pumping surface in the deployed position.

Preferably, pliable membrane 1061 is elastic, and can transition repeatedly between the stowed and deployed positions. However, although the present invention contemplates those embodiments in which only a single use of the device is contemplated, and in such embodiments membrane 1061 can be adapted and configured such that only a few deployments are anticipated before the device is discarded. Membrane 1061 can be fabricated from any material with sufficient elasticity, or alternatively, with sufficient flexibility that it can be reduced to a small, stowed configuration. As examples, the present invention contemplates those embodiments in which pliable membrane 1061 is fabricated from an elastomeric compound; in yet other embodiments membrane 1061 can be fabricated from metal foil.

Figure 32A:
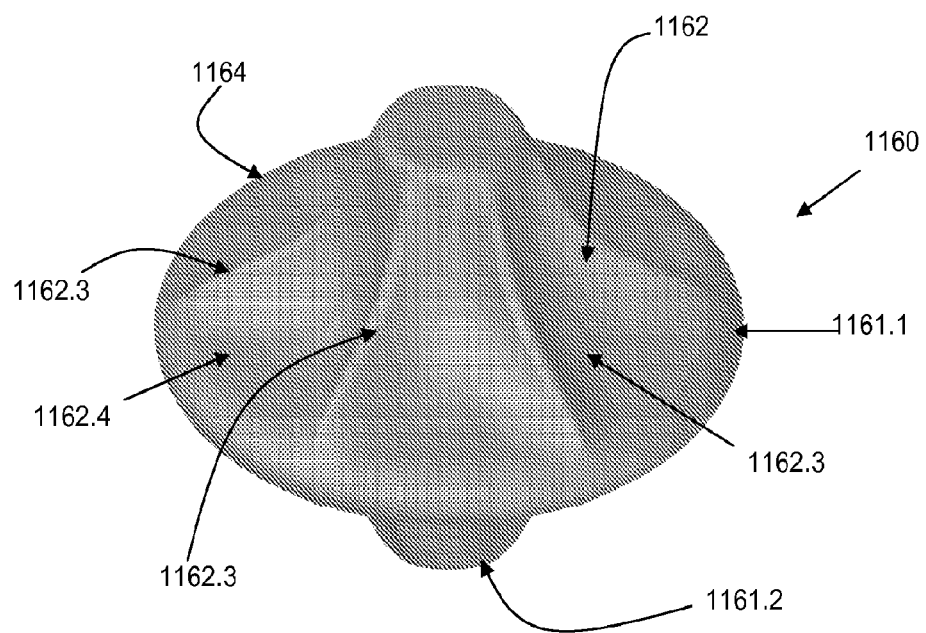
FIG. 32a is a top perspective view of a pumping element according to another embodiment of the present invention.

FIGS. 32 and 33 show impellers according to other embodiments of the present invention. FIG. 32a depicts an axial end, perspective representation of a rotor 1160. Rotor 1160 comprises an outwardly bulging midsection 1161.1 between proximal and distal hubs 1161.2 (through which the central axis of device 1120 extends). Rotor 1160 includes a membrane 1161 having a pumping surface 1162 that includes a plurality of spaced apart vanes 1162.3. In one embodiment, the vanes 1162.3 are generally established by filaments 1163.4 (not shown) of an inner tube 1163 (not shown). However, the present invention contemplates any method of creating an alternating pattern of vanes 1162.3 and depressions or troughs 1162.4, including, for example, by molding. For example, in one embodiment membrane 1161 is of generally constant thickness, but is molded into a shape during fabrication that includes a pattern of vanes and troughs. In yet another embodiment, vanes 1162.3, and in some embodiments vertex 1164 of midsection 1161.1, are created by molding a membrane of non-uniform thickness, with additional mass being added at these locations. Under centrifugal loading, these localized areas of increased mass result in additional extension of the membrane and formation of the distinctive surface features.

Figure 32B:
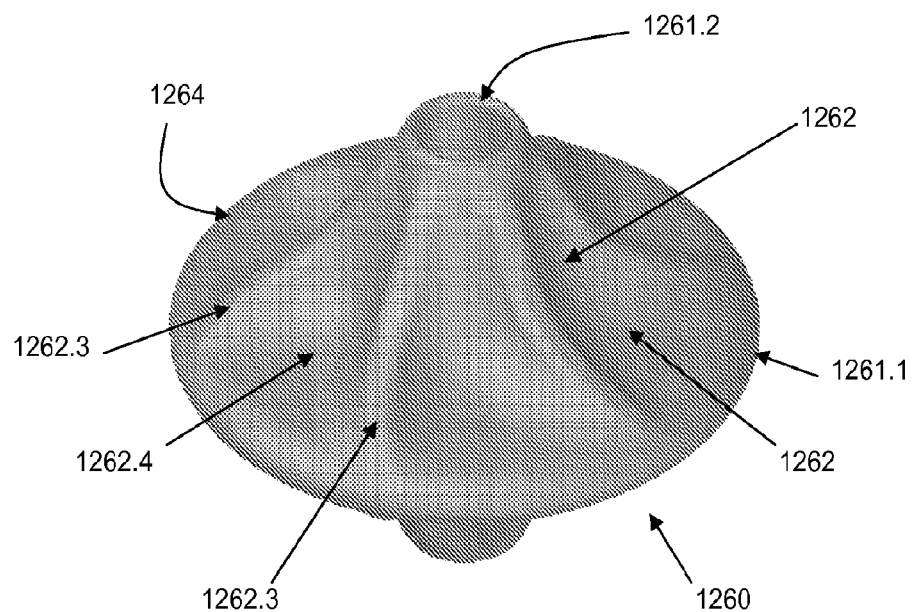
FIG. 32b is a top perspective view of a pumping element according to another embodiment of the present invention.

FIG. 32b depicts a rotor 1260 of appearance similar to that in FIG. 32a. At least one difference is that rotor 1260 includes vanes 1262.3 that include a degree of helical swirl about the central axis. The pumping surface 1262 of pump 1260 can be created in the manner as previously described for pumping surface 1162 of rotor 1160. Further, in some embodiments either of these rotor shapes can be induced by the imposition of a pressure within rotor 1260 that is less than pressure within the circulatory pathway.

FIGS. 33a and 33b depict a rotor 1360 according to another embodiment of the present invention. Rotor 1360 includes a plurality of alternating vanes 1362.3 and trough 1362.4 imposed as mirror images about a plane passing through the vertex 1364 of bulging midsection 1361.1. As indicated by arrows S1 (entrance) and S2 (exit), axial flow is induced by the pumping surface 1362 that is proximate to the proximal and distal hubs. The radially increasing profile of pumping surface 1361 proximate to hubs viscously induces flow from a circulatory pathway in with which the central axis is generally aligned. The axially induced flow continues in contact with pumping surface 1361, since the monotonically increasing radius of the pumping surface discourages separation of the viscous flow from the pumping surface. As the streamline continues along the pumping surface, it reaches the bulging midsection, and exits in a streamline S2 that includes a substantial centrifugal component. Separation of the flow at vertex 1364 is discouraged by the exiting flow S2 from the other half of rotor 1360.

Figure 34A:
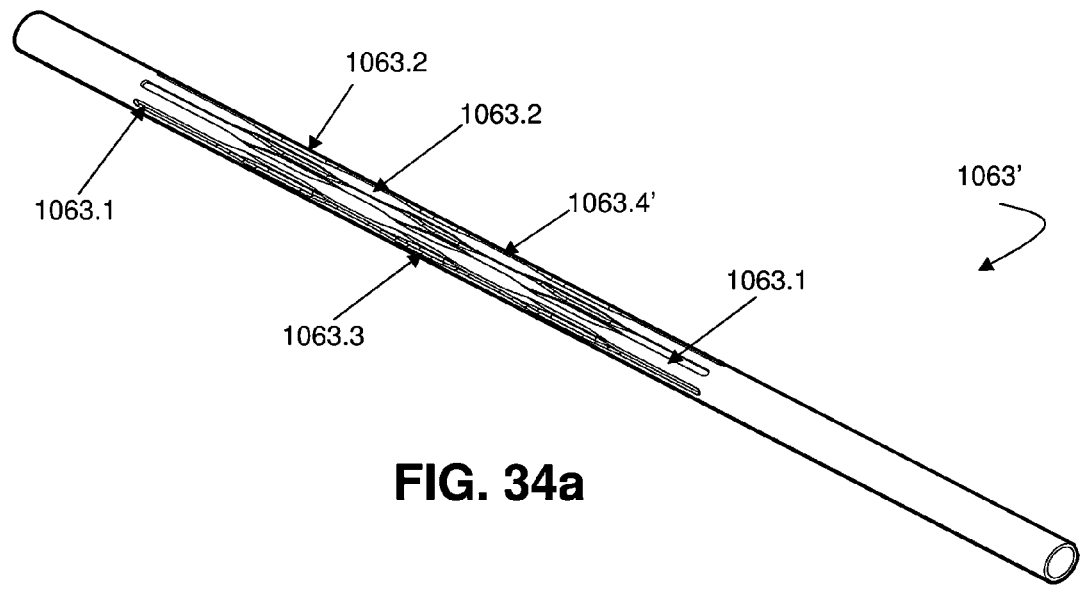
FIG. 34a is a perspective view of a portion of the apparatus of FIG. 26.
Figure 34B:
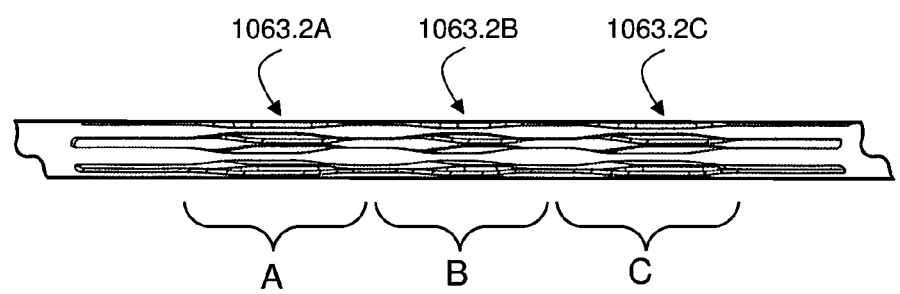

FIGS. 34 and 35 show various views of inner tube 1063 and outer tube 1043, respectively. FIGS. 34*a* and 34*b* show portions of inner tube 1063' (i.e., in the stowed position). In one embodiment, tube 1063 includes a plurality of alternating filaments 1063.4 and slots 1063.3.

FIGS. 34*a*, 34*b*, and 34*c* depict an inner tube 1063 according to one embodiment of the present invention. In apparatus 1020, the pumping surface 1062 is in part defined by an inner tube 1063 (shown in FIG. 34 in the stowed configuration). In one embodiment the tube 1063 is fabricated from a shape memory metal such as Nitinol, although other embodiments include fabrication from other bio-compatible materials, including stainless steel and titanium.

Tube 1063 includes an alternating pattern of filaments 1063.4 and slots 1063.1 spaced circumferentially about a central region of tube 1063. In some embodiments, the axial stiffness of each filament varies along the axial length of the filament. This change in stiffness alters the ability of tube 1063 to withstand compressive forces. The variable axial stiffness of the filaments creates a bulged shape during compression as the tube filaments buckle.

The change in stiffness in the axial direction can be accomplished in a variety of ways. As one example, the wall thickness of the filaments can be varied, such as with electrodischarge machining (EDM) or by localized chemical etching. Further, the shape of the filaments can be varied in their cross sectional shape by creating slots of variable width on either side of the filament. These slots can be created by any method, including EDM, laser cutting, and chemical etching. As yet another example, the filaments can include localized regions of deformation, such as by the coining of features between inner and outer dies.

Referring to FIG. 34*b*, tube 1063' includes three sections A, B, and C, each being a pattern of variable axial stiffness. In some embodiments, each pattern A, B, and C is substantially the same, although other embodiments of the present invention contemplate any type and placement of axial weakness within a pattern. For example, patterns A and C can be substantially the same, and formed by the same method, whereas pattern B can be of a different type of axial weakness.

Referring to FIGS. 34*b* and 34*c*, tube 1063 includes a pattern A in which the filaments transition in cross sectional area from a larger (and stiffer) cross sectional area 1063.4-1 to a second, smaller cross sectional area 1063.4-2. This change in cross sectional area (which can also be viewed as a change in area moment of inertia) is accomplished by increasing the width of the adjacent slots with an increase in slot width occurring starting at a radius 1063.2-1 to a second radius 1063.2-1. As can be seen along the top of the tube depicted in 34*c*, the wall thickness in this region is substantially constant. As tube 1063 is axially compressed, the -2 section of weakness between the stronger -1 sections of the filament create an area in which the tube buckles with a smaller radius.

Referring again to FIG. 34*b*, it can be seen that tube 1063' includes three lengths of reduced stiffness (1063.2*a*, 1063.2*b*, and 1063.2*c*) each within patterns A, B, and C, respectfully. As tube 1063' is compressed to its deployed shape 1063 (as best seen in FIG. 28) it can be seen that the B pattern results in the area of maximum diameter at midsection 1063.3. The centers of the A and C regions establish the concavedly inward transitional sections extending from a hub to the midsection.

Figure 35A:
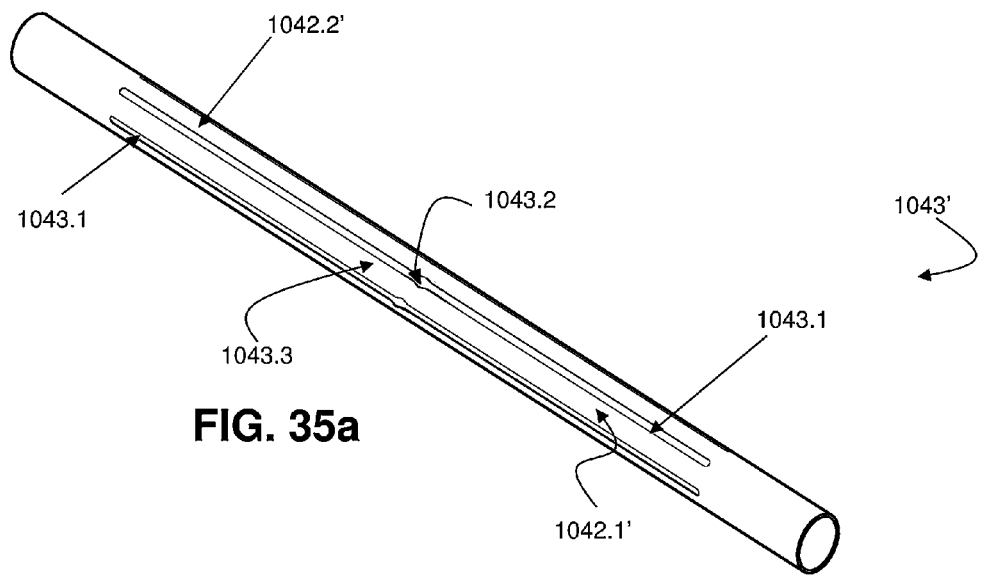
FIG. 35a is a perspective view of a portion of the apparatus of FIG. 26.
Figure 35B:
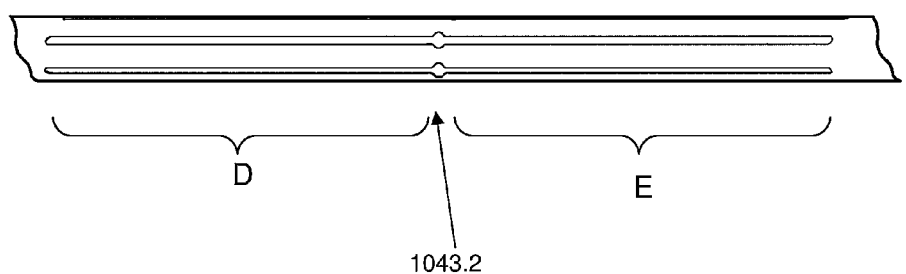

FIGS. 35*a*, 35*b*, and 35*c* depict outer tube 1043'. In one embodiment, tube 1043' includes a plurality of alternating slots 1043.1 and filaments 1043.4, preferably spaced equally about the circumference of the tube. This pattern of slots and filaments is placed within a region of tube 1043' that is intermediate of the distal and proximal ends. Referring to FIG. 34*b*, this central region of the outer tube includes distal and proximal regions D and E, respectively, separated by an area of modified stiffness 1043.2. Referring to FIG. 35*c*, the stiffness of a filament 1043.4 is modified at the center of the midsection by a pair of inwardly-cut dimples. These dimples create a localized region of reduced stiffness, such that axial compression of tube 1043 results in the bulging shape shown in FIG. 28*a*. As shown in FIG. 35, the dimples 1043.2 are placed centrally along slots 1043.1, such that the resulting bulging shape is substantially symmetrically about a vertex 1044. It is understood that reference to a "vertex" herein includes not only more sharply defined features (such as those shown in FIGS. 10 and 13 (more rounded regions) such as that shown in FIGS. 17, 18, and 19 (but also the gently curving shape shown in FIG. 28.

FIGS. 36-40 show various views and detailed components of the driving and displacement mechanism 1022. FIGS. 36*a* and 36*b* show deployed and stowed configurations 1022 and 1022', respectively. In the position showed in 36*a*, the tensioning mechanism has collapsed and thereby imparted a predetermined axial relative displacement to the distal end of apparatus 1020. Preferably, the limitation of the relative axial displacement is achieved by a hard mechanical stop, such that compression of the stowed position (FIG. 36*b*) to the deployed position (FIG. 36*a*) is limited by mechanical contact. Therefore, the maximum diameters of outer tube 1043, inner tube 1063, and membrane 1061 are limited to a safe limit that does not exceed a safe level of stress within the various materials.

Displacement and driving mechanism 1022 includes a pair of proximal tensioning arms 1023*a* pivotally coupled by pins 1025 to a corresponding pair of distal tensioning members 1023*b'*. The proximal pair of tensioning arms is pivotally coupled by pins 1025 to a proximal collar 1024*a*. Distal tensioning arms 1023*b* are likewise pivotally coupled by pins 1025 to a distal collar 1024*b*. A flexible drive rod 1034.2 passes through the inner diameter of collars 1024. The drive rod 1034.2 further passes through proximal and distal collars 1036.1*a* and 1036.1*b*, respectively. Collar 1036.1*a* is fixed to center rod 1034.2. Rod 1034.2 is free to slide within collar 1036.1*b*.

As tensioning arms 1023*a* slide within the inner cavity of drive collar 1026, the distal face of collar 1036.1*b* presses against the proximal face of tubing 1032.1. In this manner, rods 1034.1 and 1034.2 (which are fixed together) are displaced axially (to the right as shown in FIG. 36*b*) relative to outer tube 1032.1. Flexible rod 1034.1 further pulls upon outer tube 1043 and inner tube 1063, thereby creating the buckled, bulging shape shown in FIG. 28*a*.

With regards to the rotational drive of axles 1034.2, 1034.1, and pump 1060, this can be accomplished by insertion of another drive cable through the inner diameter 1026.1 of drive collar 1026. This outside driveshaft can be coupled in any manner to the proximal face of driveshaft 1034.2. Alternatively, proximal collar 1036.1a can be coupled to drive collar 1026 such that the drive collar and tensioning arms are also rotated.

Figure 41A:
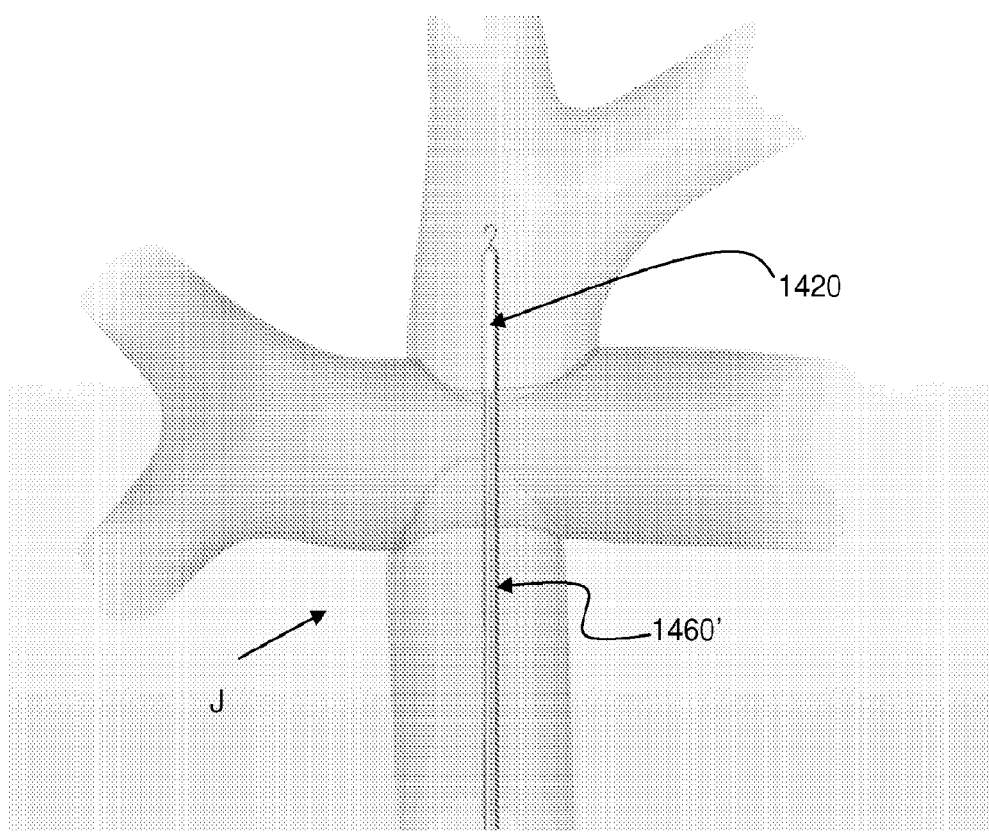
FIG. 41a is a partially transparent pictorial representation of a portion of a medical procedure according to one embodiment of the present invention.
Figure 41B:
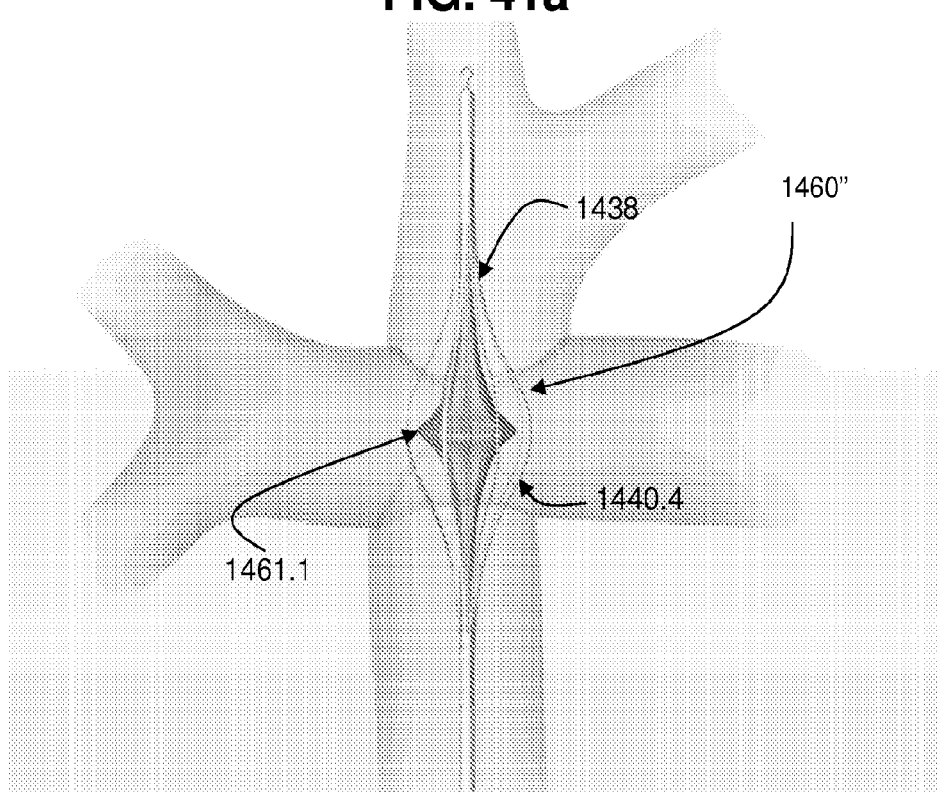
Figure 41C:
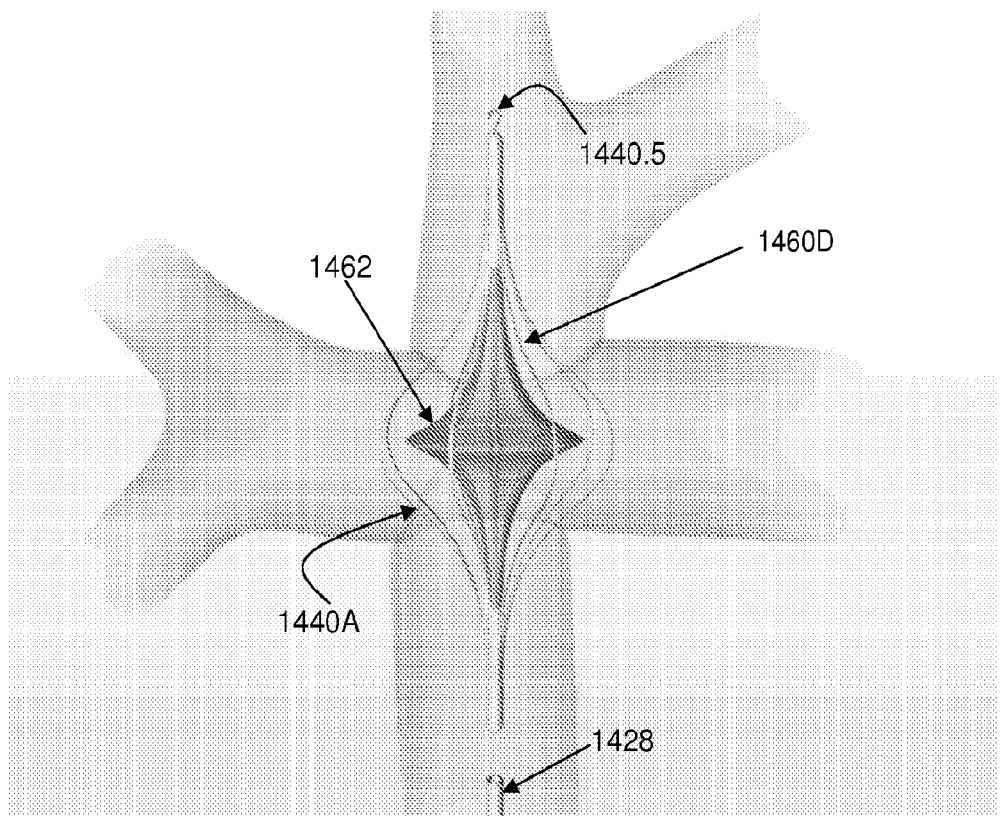
FIG. 41c is a partially transparent pictorial representation of a portion of a medical procedure subsequent to that of FIG. 41b.
Figure 41D:
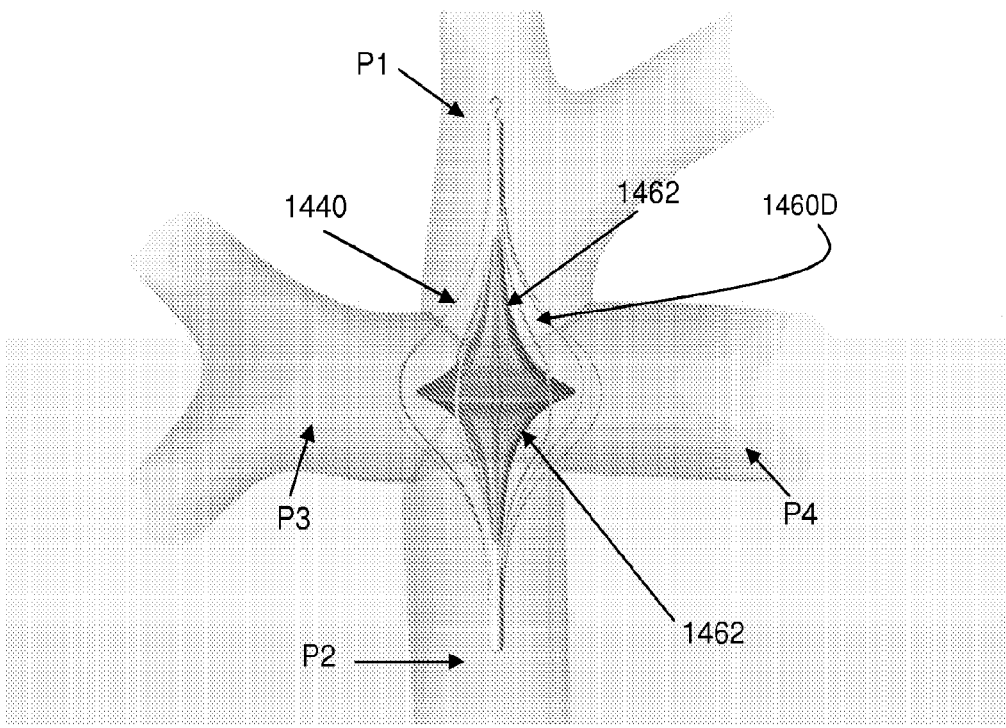
FIG. 41d is a partially transparent pictorial representation of a portion of a medical procedure subsequent to that of FIG. 41c.
Figure 42:
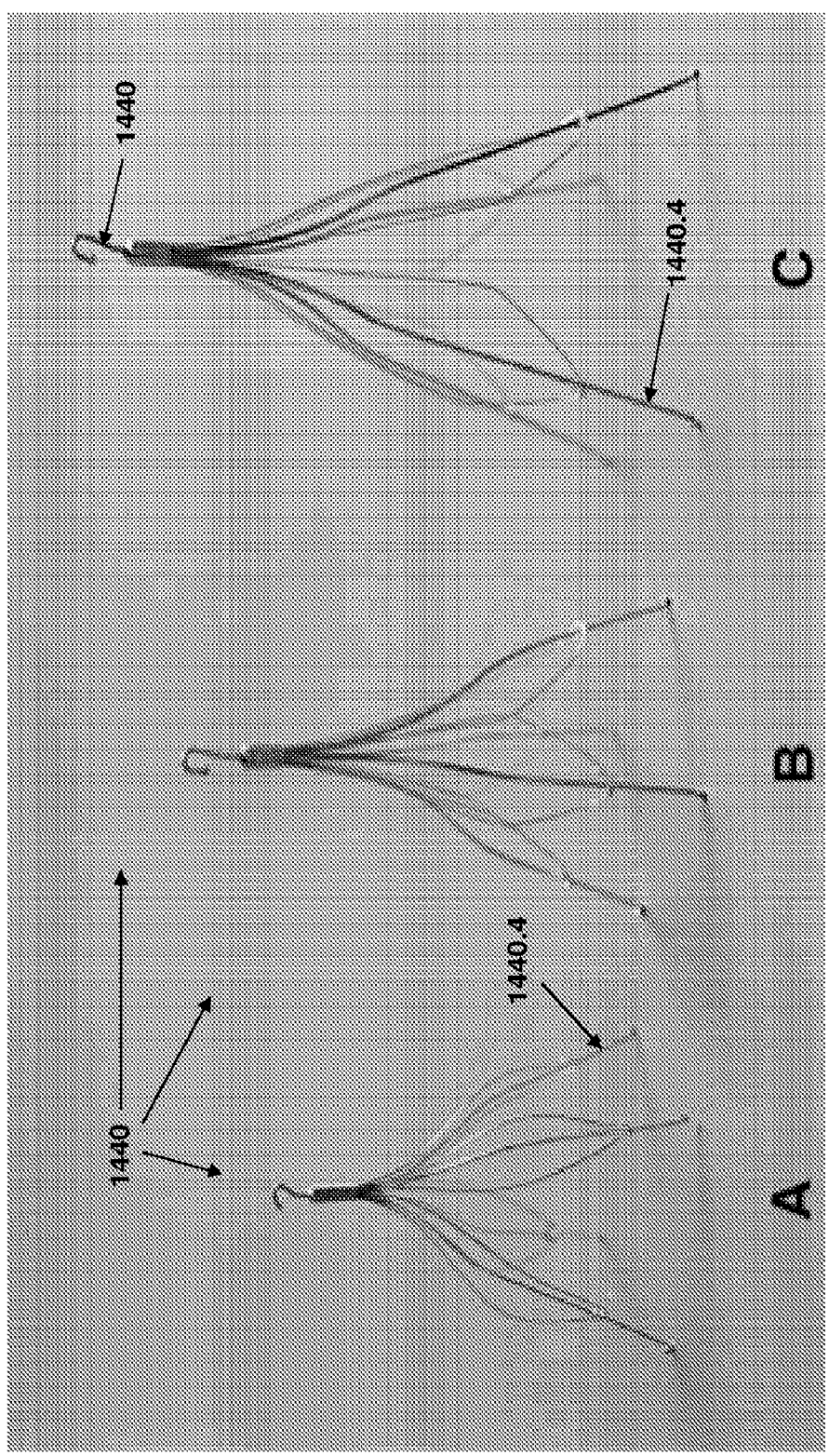
FIG. 42 shows three sizes of cages according to one embodiment of the present invention.

FIGS. 41 and 42 depict a device shown and discussed with regards to FIGS. 18-22. Assembly 1420 includes a deployable static flow device being located within a junction J in a circulatory system. Device 1420' percutaneously inserted and directed toward a junction J of circulatory pathways. In one embodiment, and as shown in these figures, device 1420 includes a flow stabilizer 1460 similar in shape to the pumps shown herein, but adapted and configured to be maintained statically at junction J in order to lessen turbulence within the junction.

In one embodiment, flow stabilizer 1460 preferentially expands (is biased to expand) to the deployed position. The stabilizer 1460 and cage 1440 are folded into a stowed position prior to percutaneous entrance. The physician advances the stowed device within a sheath, and once it is in proper position, the physician pulls the sheath back to release flow stabilizer 1460 and cage 1440 to the fully expanded and deployed position. Similar to vena caval stints, cage 1440 wedges itself against the vessel walls at the junction, which will hold flow stabilizer 1460 in place. Preferably, the central space within flow stabilizer 1460 is a closed space, such that blood is not permitted to enter it or remain present within it.

In an alternative embodiment, assembly 1420 is biased to a stowed position. The physician advances it to a desired location, unsheathes the cage and flow stabilizer from within a lumen of a catheter, and expands the cage and sheath with a degree of expansion that is tailored to the patient-specific anatomy and vessel size. Deployment of the cage and rotor can be accomplished by a screw actuator that places axial compressive loads on the ends of the cage and stabilizer in order to deploy them to an expanded position. Preferably, screw threads are internal to the device, and covered so that the threads are not exposed to blood.

As shown in FIG. 41b, the device is shown in a partially deployed state 1460" and positioned generally within the junction J. A plurality of filaments 1440.4 as shown in FIG. 41b, protective cage 1440 has expanded to a size generally the same as shown for the rotating devices previously described.

FIG. 41c shows device 1420 in its fully deployed state. Cage 1440 has continued to expand until filaments 1440.4 are at least partially in contact with walls of the pathways proximate junction J. As shown in FIG. 41c, the central span 1428 of device of 1420 is detached from the distal portion of device 1420 that includes cage 1440 and static flow divider 1460. FIG. 41d depicts the final configuration of the fully deployed devices 1440 and 1460 within junction J. As previously described surfaces 1462 are adapted and configured to provide an improved flowpath from pathways P1 and P2 into pathways P3 and P4. As shown in FIGS. 20B, 21B, and 22B, the placement of a static flow device can result in any of reduced turbulence, reduced pressure drop, and/or improved downstream flow.

Devices 1440 and 1460 can be removed in a manner similar to that of removal of vena caval filters. In one embodiment, a snare is used to engage hook 1440.5 at the end of cage 1440. A sheath defining a lumen is then advanced over the snare loop. The sheath is advanced over the remainder of the deployed cage 1440, thus forcing it and the flow stabilizer 1460 to collapse and fold into the sheath. Once the device has been pulled within the sheath, the sheath (with the device inside) is removed from the patient.

FIGS. 43-48 depict views of a pliable membrane 1561' according to another embodiment of the present invention. Membrane 1561 is adapted and configured to include troughs 1562.4 that function as recessed channels in the deployed pumping element. Trough 1562.4 is analogous in some functional aspects to the four flow channels shown and described in U.S. patent application Ser. No. 11/243,722, entitled IMPELLER FOR A ROTORY VENTRICULAR ASSIST DEVICE (by inventors Shambaugh et al.) with regards to FIGS. 2-6 of that application.

In one embodiment, membrane 1561 is molded in a shape that includes a midsection 1561.1 separating distal and proximal hubs 1561.2. Preferably, a series of troughs 1562.4 are molded into the material of the membrane. The present invention includes those embodiments in which the membrane is molded in a shape similar to that as that shown in FIG. 43, or as shown in FIGS. 30 and 31, or molded in a shape substantially the same as the deployed shape (as shown in FIG. 28a).

In one embodiment, flow channel 1562.4 is of a generally helical shape along the axis of membrane 1561, but with the helical shape being mirror-imaged at the midsection, similar to that shown in FIG. 33. Preferably, trough 1562.4 defines a channel in the pumping surface 1562. In some embodiments, trough 1562.4 includes broadened and rounded inlets 1562.5 near the hub sections. This inlet is adapted and configured for efficient induction of axial flow, and for providing that axial flow into the defined channel. FIGS. 43-48 show a membrane 1561 in which a single trough is defined within the surface of the membrane for purposes of clarity. It is understood that other embodiments include a plurality of trough circumferentially disposed about the exterior of the membrane.

FIG. 44 shows a cross sectional shape of the trough proximate to the inlet 1562.5, and in the stowed position. In some embodiments, the channel 1562.4-1 has a generally trapezoidal shape. In some embodiments, this shape is molded with a wall thickness that is thicker than the wall thickness in non-trough portions of the membrane. In this manner, the trough is more likely to retain its shape under influences of centrifugal loads, the outward urging by an inner tube with bulging filaments (not shown), or under the influence of an expansive pressure differential across the membrane. FIG. 45 shows a cross sectional view of the same trough at the midsection. This cross section shape is more closed (in some embodiments), accounting for the greater expansion of this section of membrane during deployment.

Generally, the cross sectional shape of the trough varies continuously from a cross section 44 to cross section 45. The present invention also includes those embodiments in which the depth of the defined channel either increases or decreases from inlet to midsection; those embodiments in which the wall thickness surrounding the channel either increases or decreases along the length of the channel; and also those embodiments in which the width of the channel (especially the width across the bottom of the channel) either increases or decreases along the length of the channel. All of these variations account for different pumping characteristics (pressure and flow at a particular rotational speed, and also for overall size) that can be designed into the rotor to account for different applications (industrial or medical, fluids of different viscosity, neonates or adults, etc.)

FIGS. 46-48 show the membrane of FIG. 43 in the deployed position. Membrane 1561 has a rounded, bulging midsection 1561.1 between a pair of hubs 1561.2. Bulging occurs for any of the reasons disclosed herein, including centrifugal loading, pressure differential, and stretching from expansion of an inner tube.

In one embodiment, channel 1562.4 has a width from inlet to midsection that is generally constant. However, since the radius of the channel increases, the cross sectional area of the channel at the midsection is greater than the cross sectional area closer to the inlet. Therefore, flow is generally decelerated along the length of the channel, with a commensurate increase in static pressure of fluid within the channel as it flows toward the midsection.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for pumping blood in the circulatory system of an animal, comprising:
   providing a pumping element having a pumping surface that is a body of revolution about an axis, the pumping element having distal and proximal ends along the axis, the body having a maximum diameter intermediate of the distal and proximal ends;
   positioning the pumping element at a junction of at least two pathways in the circulatory system, the axis being generally aligned with a first pathway;
   rotating the positioned pumping element;
   inducing flow of blood from the first pathway toward the pumping element by said rotating; and
   centrifuging flow of blood from the pumping element into the second pathway by said rotating.

2. The method of claim 1 wherein said providing includes a cage, and which further comprises placing the cage at the junction and wherein said positioning is within the cage.

3. The method of claim 1 wherein said positioning is percutaneous.

4. The method of claim 1 wherein said inducing is from one of the ends toward the maximum diameter, and said centrifuging is from the maximum diameter.

5. The method of claim 1 wherein the radius of the pumping surface monotonically increases along the length of the axis.

6. The method of claim 1 wherein the pumping surface includes at least one projecting vane.

7. The method of claim 1 wherein the first pathway provides flow from two generally opposite directions toward the junction.

8. A method for assisting the heart of a patient, comprising:
   providing a rotatable pump percutaneously insertable into the patient
   connecting the superior vena cava of the patient to the pulmonary artery of the patient;
   placing the pump at the junction of the SVC and PA; and
   rotating the pump to increase the energy of the blood in the PA.

9. The method of claim 8 which further comprises substantially not blocking flow from the SVC into the PA during said rotating.

10. The method of claim 9 wherein said rotating raises the total pressure of the blood by less than about 20 mm Hg.

11. The method of claim 8 wherein said rotating raises the total pressure of the blood by less than about 10 mm Hg.

12. The method of claim 8 wherein the pump is the viscous impeller type.

13. The method of claim 8 which further comprises connecting the inferior vena cava to the PA, and said placing is at the junction of the SVC, IVC, and PA.

14. An apparatus for pumping blood in an animal, comprising:
   an outer cage movable from a substantially cylindrical stowed position to a deployed position and having a midsection that is substantially open to flow of blood in the deployed position;
   a pumping element rotatable within said outer cage, said pumping element movable from a stowed position to a deployed position, said pumping element including a circumferentially-continuous flexible outer member supported by an inner cage in the deployed position, said pumping element having a distal end, a proximal end, and a deployed midsection of greatest diameter intermediate of the distal and proximal ends and
   wherein rotation of said deployed pumping element provides flow of blood radially outward from the midsection of said pumping element and through the midsection of said outer cage.

15. The apparatus of claim 14 wherein rotation of said pumping element induces flow axially from one of the distal end or the proximal end of said pumping element distal end toward the midsection of said pumping element.

16. The apparatus of claim 14 wherein said outer cage includes a midsection that does not substantially alter flow leaving said pumping element.

17. The apparatus of claim 14 wherein flow is induced by viscous drag along the surface of said outer member.

18. The apparatus of claim 14 wherein said deployed pump includes an outer surface having a pattern of projecting vanes.

19. The apparatus of claim 14 wherein said outer cage and said pumping element are biased to a stowed position.

20. The apparatus of claim 14 wherein, said outer cage, and said pumping element are aligned about an axis, and said outer cage and said pumping element are deployed by applying compression along the axis.

21. The apparatus of claim 14 wherein the stowed position of said pumping element is generally cylindrical, and said stowed pumping element is nested within said stowed outer cage.

22. The apparatus of claim 14 wherein said pumping element is rotatable about an axis, and said pumping element is symmetrical about a plane passing through the midsection of said pumping element and perpendicular to the axis.

23. An apparatus for pumping blood in an animal, comprising:
   an outer tube fabricated from a bio-compatible material and having a central axis, said outer tube having a first wall including a first region having a plurality of longitudinally-extending first slots, each pair of slots defining a first filament therebetween, the first region capable repeated movement from a generally cylindrical shape in a stowed position to a first bulging shape in a deployed position upon application of an axial load on said outer tube; and
   an inner tube fabricated from a bio-compatible material, said inner tube having a second wall and fitting within said outer tube, the second wall including a second region capable of repeated movement from a generally cylindrical shape in a stowed position to a second bulging shape in a deployed position upon application of an axial load on said inner tube, the second bulging shape having a maximum diameter smaller than the maximum diameter of the first bulging shape;
   wherein the bulged inner tube rotates within the bulged outer tube.

24. The apparatus of claim 23 wherein the filaments have a length, and one of the cross-sectional area, the thickness, or the compressive stiffness of the filaments varies along the length.

25. The apparatus of claim 23 wherein the filaments have a length and are adapted and configured to compressively buckle at a predetermined station along the length.

26. The apparatus of claim 23 wherein the second wall includes a second region of a plurality of longitudinally-extending second slots, each pair of slots defining a second filament therebetween, the second region capable of bulging to the second bulging shape upon application of a compressive axial load on said inner tube.

27. The apparatus of claim 26 wherein the second filaments have a length, and the compressive stiffness of the second filaments varies in a pattern repeated along the length.

28. The apparatus of claim 27 wherein the patterns are adapted and configured to produce a second bulging shape that is substantially symmetric about a plane transverse to the central axis at a midpoint along the length of the filaments.

29. The apparatus of claim 28 wherein the second bulging shape is inwardly concave on each side of the plane.

30. The apparatus of claim 26 which further comprises a pliable membrane covering the region of said inner tube, said membrane being expandable to cover the second bulging shape.

31. An apparatus for pumping blood in the pathways of an animal, comprising:
    means for centrifugally flowing blood toward a first pathway;
    means for axially flowing blood within a second pathway and toward said centrifugal means; and
    means for protectively containing said centrifugal means and said axial means within a junction of the first pathway and the second pathway;
    wherein blood flowing from said centrifugal means passes through said protective means into the first pathway.

32. The apparatus of claim 31 wherein said centrifugal means and said axial means are a viscous impeller pump.

33. The apparatus of claim 31 wherein said protective means is a cage within a junction of the first pathway and the second pathway.

34. A method for assisting the circulatory system of an animal, comprising:
    providing a flow stabilizing element having a continuous surface that is a body of revolution about an axis, the element having distal and proximal ends along the axis and a maximum diameter intermediate of the distal and proximal ends, the element being movable from a stowed shape suitable for percutaneous insertion and movement within the circulatory system to a deployed shape;
    positioning the stowed element at a junction of at least two pathways in the circulatory system, the axis being generally aligned to receive blood flow from a first pathway and toward one end of the element;
    deploying the element to the deployed shape and
    directing flow along the surface from the one end to the maximum diameter and toward the second pathway.

35. The apparatus of claim 31 wherein rotation of said centrifugal flow means induces flow toward said centrifugal flow means from said axial flow means in two opposing axial directions.

36. The apparatus of claim 31 wherein said centrifugal flow means and said axial flow means are repeatedly deployable from a coaxial stowed position to a deployed operational position.

37. The apparatus of claim 36 wherein the deployment is by compression of said centrifugal flow means, said axial flow means, and said protective means.

38. The apparatus of claim 31 wherein said centrifugal flow means has a first viscous impelling surface and said axial flow means has a second viscous impelling surface, and the first surface and the second surface comprise a single smoothly contouring exterior.

* * * * *